United States Patent
Pruteanu et al.

(10) Patent No.: US 11,766,427 B2
(45) Date of Patent: Sep. 26, 2023

(54) REPURPOSING COMPOUNDS FOR THE TREATMENT OF INFECTIONS AND FOR MODULATING THE COMPOSITION OF THE GUT MICROBIOME

(71) Applicant: EUROPEAN MOLECULAR BIOLOGY LABORATORY, Heidelberg (DE)

(72) Inventors: Mihaela Pruteanu, Berlin (DE); Lisa Maier, Tübingen (DE); Michael Kuhn, Heidelberg (DE); Peer Bork, Heidelberg (DE); Athanasios Typas, Heidelberg (DE); Kiran Raosaheb Patil, Cambridge (GB); Georg Zeller, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 166 days.

(21) Appl. No.: 16/966,307

(22) PCT Filed: Feb. 13, 2019

(86) PCT No.: PCT/EP2019/053500
§ 371 (c)(1),
(2) Date: Jul. 30, 2020

(87) PCT Pub. No.: WO2019/158559
PCT Pub. Date: Aug. 22, 2019

(65) Prior Publication Data
US 2020/0368218 A1     Nov. 26, 2020

(30) Foreign Application Priority Data
Feb. 13, 2018   (EP) .................... 18156520

(51) Int. Cl.
*A61K 31/4422* (2006.01)
*A61K 31/137* (2006.01)
*A61P 31/04* (2006.01)

(52) U.S. Cl.
CPC ........ *A61K 31/4422* (2013.01); *A61K 31/137* (2013.01)

(58) Field of Classification Search
CPC ............. A61K 31/4422; A61K 31/137; C07D 211/90; A61P 31/04
See application file for complete search history.

(56) References Cited

FOREIGN PATENT DOCUMENTS

| CN | 102068437 A | 5/2011 |
| WO | 2010026602 A2 | 3/2010 |
| WO | 2015017402 A1 | 2/2015 |

OTHER PUBLICATIONS

McCormack et al. Drugs 2003, 63 (21), 2327-2356.*
Mathew et al. The Pharma Innovation Journal 2017, 6 (8), 165-170.*
Khoshneviszadeh et al. Bioorganic Medicinal Chemistry 2009, 17, 1579-1586.*
Mair et al. Journal of Infectious Diseases 2011, 204 (5), 685-694.*
Dasgupta, Asish et al. "Studies on the Antimicrobial Potential of the Cardiovascular Drug Lacidipine", In Vivo, vol. 21, pp. 847-850, 2007.
Mazumdar, K. et al. "Potential role of the cardiovascular non-antibiotic (helper compound) amlodipine in the treatment of microbial infections: scope and hope for the future" International Journal of Antimicrobial Agents, Elsevier, Amsterdam, NL, vol. 36, No. 4, pp. 295-302, Oct. 1, 2010.

* cited by examiner

*Primary Examiner* — Irina Neagu
(74) *Attorney, Agent, or Firm* — SALIWANCHIK, LLOYD & EISENSCHENK

(57) ABSTRACT

The present invention relates to agents and compositions for the modification of the growth of bacterial cells. Thus, the compounds of the present invention are useful for the prevention and/or treatment of a disease in a subject. In particular, the present invention relates to the field of repurposing pharmaceutical compounds for treatment strategies of infectious diseases, gastrointestinal disorders, inflammatory diseases, proliferative diseases, metabolic disorders, cardiovascular diseases, and immunological diseases. Some of the compounds of the present invention demonstrate high specificity in inhibiting the growth of single bacterial species. Such compounds enable narrow-spectrum antibacterial therapies, constituting a major effort of current and future drug development strategies in order to reduce side effects of antibacterial treatment plans. Particularly interesting compounds of this invention are effective against pathobiological species such as *Clostridium difficile, Clostridium perfingens, Fusobacterium nucleatum*, and an enterotoxigenic strain of *Bacteroides fragilis*. Other compounds of the present invention reveal a strong inhibitory effect on a broad spectrum of bacterial species. Such compounds are useful for broad-spectrum antibiotic therapies of infections with unknown causative infecting bacterial species. Both types of compounds, especially the ones with narrow-spectrum antibacterialactivity, can further be used for modulating the microbiome composition and targeting species associated with dysbiosis and disease.

Figure 1:
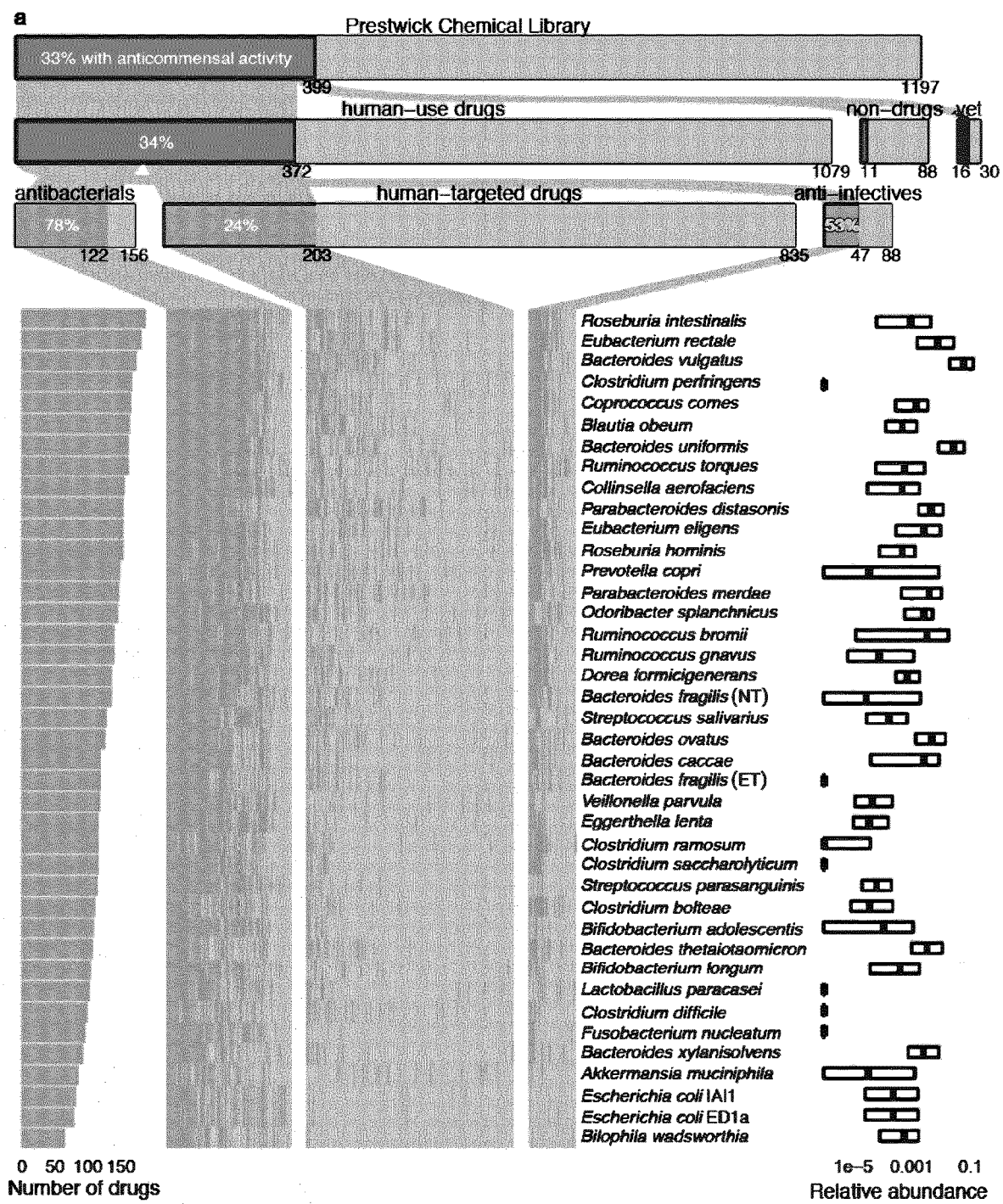
Figure 1:
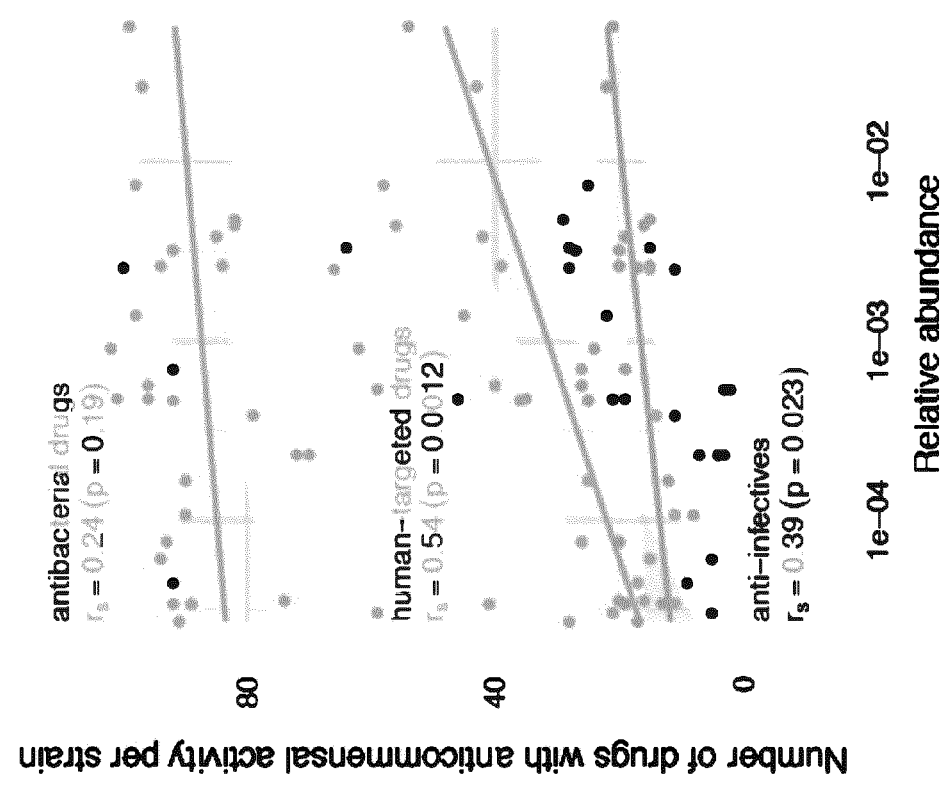
Figure 1:
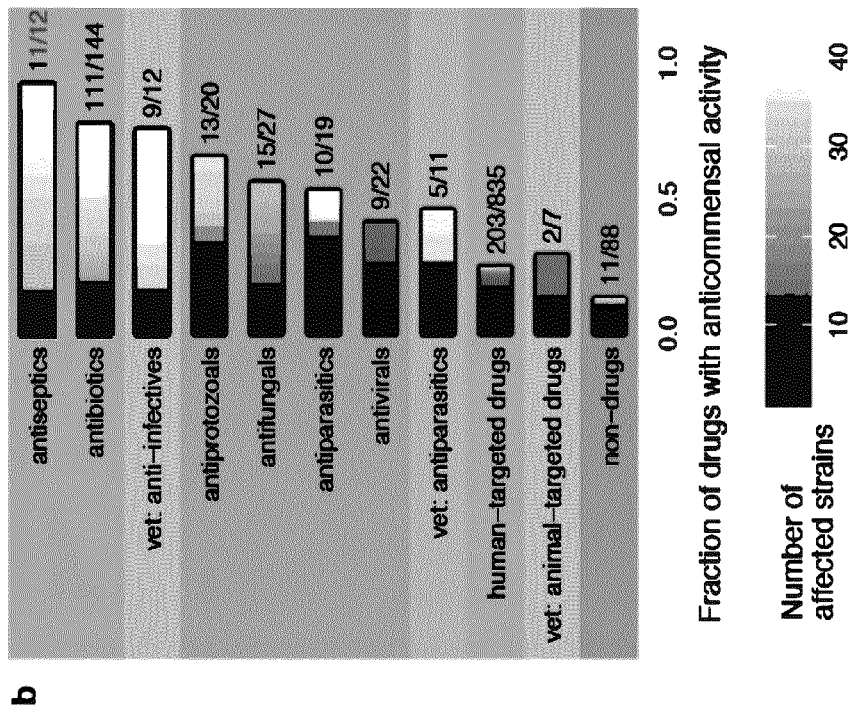

7 Claims, 15 Drawing Sheets b Flemish cohort study

REPURPOSING COMPOUNDS FOR THE TREATMENT OF INFECTIONS AND FOR MODULATING THE COMPOSITION OF THE GUT MICROBIOME

CROSS REFERENCE TO RELATED APPLICATIONS

This application is a National Stage Application of International Application Number PCT/EP2019/053500, filed Feb. 13, 2019; which claims priority to European Application No. 18156520.1, filed Feb. 13, 2018.

The present invention relates to agents and compositions for the modification of the growth of bacterial cells. Thus, the compounds of the present invention are useful for the prevention and/or treatment of a disease in a subject. In particular, the present invention relates to the field of repurposing pharmaceutical compounds for treatment strategies of infectious diseases, gastrointestinal disorders, inflammatory diseases, proliferative diseases, metabolic disorders, cardiovascular diseases, and immunological diseases. Some of the compounds of the present invention demonstrate high specificity in inhibiting the growth of single bacterial species. Such compounds enable narrow-spectrum antibacterial therapies, constituting a major effort of current and future drug development strategies in order to reduce side effects of antibacterial treatment plans. Particularly interesting compounds of this invention are effective against pathobiological species such as *Clostridium difficile, Clostridium perfringens, Fusobacterium nucleatum*, and an enterotoxigenic strain of *Bacteroides fragilis*. Other compounds of the present invention reveal a strong inhibitory effect on a broad spectrum of bacterial species. Such compounds are useful for broad-spectrum antibiotic therapies of infections with unknown causative infecting bacterial species. Both types of compounds, especially the ones with narrow-spectrum antibacterial activity, can further be used for modulating the microbiome composition and targeting species associated with dysbiosis and disease.

BACKGROUND OF THE INVENTION

The spread of antimicrobial resistance has become a serious public health concern, making once treatable diseases deadly again and undermining breakthrough achievements of modern medicine. Discovery of new antibacterial therapies is imperative, but developing novel drugs takes years and, unfortunately, antibiotic development has stalemated in the last three decades.

To identify effective antibacterial compounds, drug repurposing can act as a first line of defense, as promising candidates can be moved quickly to clinical applications, when individual compounds are already approved and/or in use. Therefore, the inventors systematically profiled interactions between commonly used drugs and a large number of bacterial species. Such knowledge can be used to improve current therapies and facilitate drug design by opening new paths for controlling side effects and for drug repurposing: new MoAs, tools to modulate bacterial communities or scaffolds for new antimicrobials. A better understanding of the collateral damage compounds have on bacteria may lead to more targeted treatments with reduced risks for antibiotic resistance.

As a first step towards uncovering the complex interactions between microbes and marketed drugs, the inventors established a large-scale in vitro compound screen and tested >1000 drugs for their direct impact on the growth of 40 of the most representative members of the human gut microbiome community, including a number of pathobionts (such as *Clostridium difficile, Clostridium perfringens, Fusobacterium nucleatum* and an enterotoxigenic strain of *Bacteroides fragilis*). The term 'microbiome' refers to a remarkable variety of bacteria, archaea, fungi, and viruses which colonize the gut, vagina, and skin.

The inventors found that many compounds, whose mechanism of action is known to affect human cells (referred to as human-targeted drugs), also have a broad impact on microbes. This antimicrobial activity is visible in their side effect patterns in humans, illustrating the in vivo relevance of the screen. The inventors also uncovered patterns at the species and drug levels, identifying drug classes with consistent effects on microbes. The inventors further demonstrated an overlap between microbial resistance mechanisms to antibiotics and to human-targeted drugs, suggesting that the later may also enhance selection pressure towards antibiotic resistance.

In general, there are two large classes of compounds with antibiotic activity: Narrow-spectrum and broad-spectrum antibiotic compounds. Narrow-spectrum compounds demonstrate high specificity in inhibiting the growth of a single bacterial species and/or bacterial strain. Such compounds enable antibacterial therapies against selected bacterial species and/or strains, in some cases even single species or strains, constituting a major effort of current and future drug development strategies in order to prevent adverse effects of antibacterial treatment plans, such as the negative impact of compounds on healthy microorganisms residing in the patients' body, such as the gut microbiota.

Broad-spectrum antibiotic compounds bear the risk of harming the normal and healthy intestinal flora. This disturbance facilitates bacterial overgrowth and can be the cause of the development of antibiotic resistance in microorganisms. Antibiotic resistant bacteria themselves can cause serious infections. As a consequence, a further serious problem governs the possible transfer of resistance factors to other bacteria. Thus, compared to broad spectrum antibacterial therapies, selective pharmaceutical compositions are far less likely to select for antimicrobial resistance and are less harmful for the patients' intestinal flora.

A particular subset of bacterial pathogens is those classified as spore-forming bacteria. Bacterial spores are formed in response to environmental stress. Upon more favorable environmental conditions, the spores germinate and the bacteria proliferate. Importantly, germination of spores formed by pathogenic bacteria in a human host can be the cause of multiple diseases. Bacterial spores are exceptionally tolerant to multiple agents and environmental conditions including radiation, desiccation, temperature, starvation and most chemical agents.

This natural tolerance to chemical agents allows spores to persist for many months in environments such as hospitals and food production facilities, where standard cleaning agents, germicides and sterilization processes do not eradicate the bacteria. The presence of spores in food production facilities can have significant consequences, such as food poisoning and the spread of foodborne pathogens.

Important spore-forming bacteria are the Gram-positive endospore-forming bacteria of the genus *Clostridium*. Of particular concern is the commensal enteric bacterium *C. difficile*, the levels of which are normally kept in balance by the enteric gut flora. However, *C. difficile* is the causative agent of *C. difficile*-associated diseases (CDAD), a severe worldwide health threat. CDAD are associated with multiple diverse symptoms ranging from mild diarrhoea to pseudomembraneous colitis, toxic megacolon and death. The main risk factor for the development of CDAD is the use of antibiotics, specifically broad-spectrum antibiotics, which disrupt the normal enteric bacterial gut flora and cause an overgrowth of C. difficile. CDAD are associated with nearly all antibiotic classes including members of the fluoroquinolone, cephalosporin, macrolide, β-lactam and many others classes.

Within the last 10 years, there has been a ten-fold increase in the number of CDAD cases, with hyper-virulent and drug resistant strains now becoming endemic. Only in the U.S., 453,000 CDAD cases were reported in 2011. Importantly, mortality rates associated with CDAD in the U.S. have risen from 5.7 per million of population in 1999 to 90 per million in 2011, according to CDC. Methods to treat CDAD are very limited, while the recurrence rate for CDAD is as high as 25%. The increased incidence and severity of the disease coupled with a decreased response to current therapies, high recurrence rates, and the emergence of numerous antibiotic resistant bacterial strains has created a significant public health threat and an urgent need for new treatment strategies.

Broad-spectrum antibiotic compounds, on the other hand, are characterized by having a strong antibacterial effect on an extensive spectrum of bacterial species and strains. Such compounds are vital for treatment of bacterial infections, when the causative species is unknown. Broad-spectrum antibiotic compounds can quickly suppress the origin of an infection without the need of identifying the infecting pathogen with real certainty before commencing the treatment. This is specifically necessary in the treatment of serious diseases, where patients can become fatally ill within hours if an antibiotic effect is not initiated quickly, such as meningitis. Moreover, in complex diseases it is often difficult to identify the infecting pathogen within the wide range of possible illnesses. Broad-spectrum antibiotic compounds are also necessary to combat superinfections, where multiple types of bacteria are causing the illness. Importantly, broad-spectrum antibiotic compounds are also useful as prophylaxis shortly before an incision, e.g. for an operation, in order to prevent the occurrence of bacterial infections.

Under most circumstances, gut microbes help digest food as well as maintain immune functions in the host. Recent improvements of high-throughput environmental shotgun sequencing techniques enabled an efficient and cost-effective tool for investigating the members of the microbiome. Subsequently, many links between dysfunctions of the human microbiota and diseases such as gastrointestinal disorders, proliferative diseases, metabolic disorders, cardiovascular diseases, immunological diseases, and infectious diseases have been established. Recent progress in the field suggests the use of the microbiome as an early detection biomarker for diseases and makes the human microbiome a target for therapeutic intervention.

The term "dysbiosis" (also called dysbacteriosis) refers to an imbalance of the microbiome. As such, species that are normally underrepresented in the microbiome become overrepresented, whereas normally dominated species become underrepresented. Most often, dysbiosis is a condition in the gastrointestinal tract, particularly during small intestinal bacterial overgrowth (SIBO) or small intestinal fungal overgrowth (SIFO). It has been reported to be associated with illnesses, such as periodontal disease, inflammatory bowel disease, chronic fatigue syndrome, obesity, cancer, bacterial vaginosis, and colitis.

The present invention is based on the surprising finding that many compounds, whose mechanism of action is known to affect human cells (referred to as human-targeted drugs) are also effective against bacteria.

For example, the inventors surprisingly identified Ca-channel blockers such as Dihydropyridine and its derivatives (such as Lacidipine) to selectively inhibit the growth of the pathobiont C. difficile. Dihydropyridines are Calcium Channel Blockers primarily used for treatment of hypertension and cardiovascular diseases. They are commonly used to reduce systemic vascular resistance and arterial pressure and are thought to act as allosteric modulators of voltage-dependent $Ca^{2+}$ channel activation.

WO 2005025507 A2 discloses the use of Dihydropyridine compounds for treating or preventing metabolic disorders. The treatment of bacterial infections is not mentioned.

Younis et al. (in Younis et al.: In Vitro Screening of an FDA-Approved Library Against ESKAPE Pathogens. *Current Pharmaceutical Design*, 2017, 23, 1-11) previously performed a screening of the antibacterial activity of an FDA-Approved Library against each of the so-called "ESKAPE" pathogens (*Enterococcus faecium, Staphylococcus aureus, Klebsiella pneumoniae, Acinetobacter baumannii, Pseudomonas aeruginosa,* and *Enterobacter* species). Their screen revealed several compounds the inventors' screen replicated. Some of these include examples such as Floxuridine, Terfenadine, Benzbromarone, Tamoxifen citrate, Daunorubicin, and Methotrexate. However, an antibacterial activity of the compounds of this invention, in particular Lacidipine, Cilnidipine, Amlodipine, Fendiline hydrochloride, Tribenoside, Telmisartan, Azathioprine, Mercaptopurine, Mifepristone, Montelukast, Fentiazac, Meclozine dihydrochloride, Carbenoxolone, Gliquidone, Alfacalcidol, Acarbose, Ethacrynic acid, Chlorpromazine hydrochloride, Cyclosporin A, Flufenamic acid, Aripiprazole, Idebenone, Thioguanosine, Thyroxine (L), Gemcitabine, Folic acid, Etretinate, Paclitaxel, Phenindione, Mometasone furoate, Azacytidine-5, Luteolin, Metixene hydrochloride, Protriptyline hydrochloride, Toltrazuril, Tolnaftate, Meclofenamic acid, Prenylamine lactate, Diacerein, Dicumarol, Clemizole hydrochloride, Loratadine, Troglitazone, Tiratricol, Bepridil hydrochloride, Estradiol Valerate, Anthralin, Aprepitant, Amiodarone hydrochloride, Ethopropazine hydrochloride, Astemizole, and Methiothepin maleate was not mentioned.

US20170065540A1 screened the antibacterial activity of the Prestwick library against *E. coli* and each of the "ESKAPE" pathogens (1,120 compounds in total; 50 µM final drug concentration). Their high-throughput screening assay was based on the detection of the release of intracellular adenylate kinase into culture medium as a reporter of bacterial cell death. The inventors defined a compound as having antibacterial activity if it exhibited a significant increase in the detected adenylate kinase signal (≥3-fold over that for vehicle-treated cells). This screening method verified some of the hits also identified by the present inventors' screen. These include examples such as, but not limited to, Terfenadine, Tamoxifen citrate, Hexestrol, Dienestrol, Felodipine, and Perhexiline maleate. However, this screening method did not detect an antibiotic activity of the compounds of this invention, in particular Lacidipine, Cilnidipine, Amlodipine, Fendiline hydrochloride, Tribenoside, Telmisartan, Azathioprine, Mercaptopurine, Mifepristone, Montelukast, Fentiazac, Meclozine dihydrochloride, Carbenoxolone, Gliquidone, Alfacalcidol, Acarbose, Ethacrynic acid, Chlorpromazine hydrochloride, Cyclosporin A, Flufenamic acid, Aripiprazole, Idebenone, Thioguanosine, Thyroxine (L), Gemcitabine, Folic acid, Etretinate, Paclitaxel, Phenindione, Mometasone furoate, Azacytidine-5, Luteolin, Metixene hydrochloride, Protriptyline hydrochloride, Toltrazuril, Tolnaftate, Meclofenamic acid, Prenylamine lactate, Diacerein, Dicumarol, Clemizole hydrochloride, Loratadine, Troglitazone, Tiratricol, Bepridil hydrochloride, Estradiol Valerate, Anthralin, Aprepitant, Amiodarone hydrochloride, Ethopropazine hydrochloride, Astemizole, and Methiothepin maleate.

So far, no screening experiment against a large number of representative members of the human gut microbiome using the Prestwick library compounds has been performed. Thus, previous studies missed the broad antibacterial activity of compounds such as Lacidipine, Cilnidipine, Amlodipine, Fendiline hydrochloride, Tribenoside, Telmisartan, Azathioprine, Mercaptopurine, Mifepristone, Montelukast, Fentiazac, Meclozine dihydrochloride, Carbenoxolone, Gliquidone, Alfacalcidol, Acarbose, Ethacrynic acid, Chlorpromazine hydrochloride, Cyclosporin A, Flufenamic acid, Aripiprazole, Idebenone, Thioguanosine, Thyroxine (L), Gemcitabine, Folic acid, Etretinate, Paclitaxel, Phenindione, Mometasone furoate, Azacytidine-5, Luteolin, Metixene hydrochloride, Protriptyline hydrochloride, Toltrazuril, Tolnaftate, Meclofenamic acid, Prenylamine lactate, Diacerein, Dicumarol, Clemizole hydrochloride, Loratadine, Troglitazone, Tiratricol, Bepridil hydrochloride, Estradiol Valerate, Anthralin, Aprepitant, Amiodarone hydrochloride, Ethopropazine hydrochloride, Astemizole, and Methiothepin maleate.

Interestingly, many of the compounds of this invention are effective in inhibiting the growth of a narrow spectrum of bacterial species. Importantly Lacidipine, Cilnidipine, Amlodipine, Fendiline hydrochloride, Tribenoside, Telmisartan, Azathioprine, Mercaptopurine, Mifepristone, Montelukast, Fentiazac, Meclozine dihydrochloride, Carbenoxolone, and Gliquidone are effective in inhibiting the growth of *C. difficile* bacteria, which are the cause of many serious bacterial infections.

Moreover, Alfacalcidol, Acarbose, Ethacrynic acid, Chlorpromazine hydrochloride, Cyclosporin A, Idebenone, Thioguanosine, Gemcitabine, Etretinate, Paclitaxel, Phenindione, Azacytidine-5 are selectively inhibiting the growth of *C. perfringens* bacteria, which are a further cause of multiple bacterial infections, and thus an important target of current therapeutic strategies.

Luteolin is a compound that is selectively inhibiting the growth of *Fusobacterium nucleatum*, which has been identified as a causative agent of colorectal cancer. Thus, Luteolin is a promising strategy to prevent colorectal cancer.

Moreover, some of the compounds of the present invention are selectively inhibiting the growth of an enterotoxigenic strain of *Bacteroides fragilis*. Specifically, those compounds are Metixene hydrochloride, Protriptyline hydrochloride, Toltrazuril, Acarbose, Ethacrynic acid, Tolnaftate, Cilnidipine, Meclofenamic acid, and Prenylamine lactate.

The development and spread of antibacterial resistance governs one of the most serious threats to public health, generating bacterial strains against which no known compound is having an antibacterial effect. Thus, there is an urgent need to offer novel antibacterial pharmaceutical compositions that can overcome bacterial antibiotic resistance. It is therefore an object of the present invention to repurpose pharmaceutical compounds to effectively prevent and treat infections.

The problem of the present invention is solved by providing multiple narrow-spectrum as well as broad-spectrum compounds with antibiotic activity. Other objects of the present invention will become apparent to the person of skill when studying the specification of the present invention.

In a first aspect thereof, the object of the present invention is solved by providing a compound for use in the modification of the growth of bacterial cells, wherein said compound is selected from a Ca-channel inhibitor, Tribenoside, Telmisartan, Azathioprine, Mercaptopurine, Mifepristone, Montelukast, Fentiazac, Meclozine dihydrochloride, Carbenoxolone, Gliquidone, Alfacalcidol, Acarbose, Ethacrynic acid, Chlorpromazine hydrochloride, Cyclosporin A, Flufenamic acid, Aripiprazole, Idebenone, Thioguanosine, Thyroxine (L), Gemcitabine, Folic acid, Etretinate, Paclitaxel, Phenindione, Mometasone furoate, Azacytidine-5, Luteolin, Metixene hydrochloride, Protriptyline hydrochloride, Toltrazuril, Tolnaftate, Meclofenamic acid, Prenylamine lactate, Diacerein, Dicumarol, Clemizole hydrochloride, Loratadine, Troglitazone, Tiratricol, Bepridil hydrochloride, Estradiol Valerate, Anthralin, Aprepitant, Amiodarone hydrochloride, Ethopropazine hydrochloride, Astemizole, Methiothepin maleate, pharmaceutically acceptable salts thereof, and derivatives thereof, preferably wherein said modification is an inhibition or an enhancement of the growth of said bacterial cells.

The aforementioned compound for use can generally be used for modifying the growth of a wide variety of bacterial cells. Without intending to be restricted to the following examples, the compound for use can be used to modify the growth of bacterial cells selected from cells of Gram-positive bacteria, Gram-negative bacteria, *Enterobacter, Staphylococcus, Streptococcus, Pseudomonas, Escherichia, Salmonella, Helicobacter, Neisseria, Campylobacter, Chlamydia, Clostridia, Citrobacter, Vibrio, Treponema, Mycobacterium, Klebsiella, Actinomyces, Bacteroides, Bordetella, Borrelia, Brucella, Corynebacteria, Diplococcus, Fusobacterium, Leptospira, Listeria, Pasteurella, Proteus, Rickettsia, Shigella, Yersinia, Parabacteroides, Odoribacter, Faecalibacteria, Collinsella, Eggerthella, Lactonifactor, Pediococcus, Leuconostoc, Lactococcus, Roseburia, Coliform, Bacillus, Franscicella, Acinetobacter, Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella, Enterococcus*, and combinations thereof, optionally wherein said bacteria are antibiotic-resistant bacteria and/or multi-drug resistant bacteria.

In a preferred aspect, the compound of the present invention is administered to a subject, thereby modifying the growth of bacterial cells in said subject, wherein said modifying results in the prevention and/or treatment of a disease in said subject and/or in the modification of the composition of the microbiome of said subject, preferably wherein said subject is a mammal, such as a mouse, rat, guinea pig, rabbit, cat, dog, monkey, or preferably a human, such as a human patient, optionally wherein said compound is administered to said subject in a therapeutically effective amount, thereby preventing and/or treating a disease in said subject and/or modifying the composition of the microbiome of said subject.

The aforementioned compound for use can generally be used in the prevention and/or treatment of a wide variety of diseases. Without intending to be restricted to the following examples, the compound can be used in the prevention and/or treatment of a disease selected from an infectious disease, a gastrointestinal disorder, an inflammatory disease, a proliferative disease, a metabolic disorder, a cardiovascular disease, and an immunological disease, preferably wherein said infectious disease is selected from an infection of the gastrointestinal tract, an infection of the urogenital tract, an infection of the upper lower respiratory tract, an infection of the lower respiratory tract, rhinitis, tonsillitis, pharyngitis, dysbiosis, bronchitis, pneumonia, an infection of the inner organs, nephritis, hepatitis, peritonitis, endocarditis, meningitis, osteomyelitis, an infection of the eyes, an infection of the ears, a cutaneous infection, a subcutaneous infection, an infection after burn, diarrhea, colitis, pseudomembranous colitis, a skin disorder, toxic shock syndrome, bacteremia, sepsis, pelvic inflammatory disease, vaginosis, an infection of the central nervous system, wound infection, intra-abdominal infection, intravascular infection, bone infection, joint infection, acute bacterial otitis media, pyelonephritis, deep-seated abscess, and tuberculosis, and/ or wherein said gastrointestinal disorder is preferably selected from a gastrointestinal motility disorder, irritable bowel syndrome, constipation, a functional gastrointestinal disorder, gastroesophageal reflux disease, functional heartburn, dysbiosis, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten intolerance and/or lactose intolerance, obesity, stomach rumble, small intestinal bacterial overgrowth (SIBO), small intestinal fungal overgrowth (SIFO), meteorism, and flatulence, and/or wherein said inflammatory disease is preferably an intestinal inflammatory disease selected from Crohn's disease, inflammatory bowel disease, ulcerative colitis, collagenous-, lymphocytic-, ischemic-, diversion- and/or indeterminate colitis, periodontal disease, chronic fatigue syndrome, myalgic encephalomyelitis, and Behçet's disease, and/or wherein said proliferative disease is preferably selected from atherosclerosis, rheumatoid arthritis, and a cancer disease, more preferably wherein said proliferative disease is a cancer disease, such as gastric cancer and/or colorectal cancer.

Another embodiment of the invention pertains to the afore-described compound, wherein said compound is in liquid, dry or semi-solid form, such as, for example, in the form of a tablet, coated tablet, effervescent tablet, capsule, powder, granulate, sugar-coated tablet, lozenge, pill, ampoule, drop, suppository, emulsion, ointment, gel, tincture, paste, cream, moist compress, gargling solution, plant juice, nasal agent, inhalation mixture, aerosol, mouthwash, mouth spray, nose spray or room spray, optionally wherein said compound is administered to said subject by oral, intranasal, topical, rectal, bronchial, vaginal, or parenteral administration, or by any clinically/medically accepted method.

Yet another preferred embodiment of the present invention relates to the compound for use, wherein said compound is for use in the modification of the growth of bacterial cells of a spectrum of bacterial species selected from Gram-positive bacteria, Gram-negative bacteria, *Enterobacter, Staphylococcus, Streptococcus, Pseudomonas, Escherichia, Salmonella, Helicobacter, Neisseria, Campylobacter, Chlamydia, Clostridia, Citrobacter, Vibrio, Treponema, Mycobacterium, Klebsiella, Actinomyces, Bacteroides, Bordetella, Borrelia, Brucella, Corynebacteria, Diplococcus, Fusobacterium, Leptospira, Listeria, Pasteurella, Proteus, Rickettsia, Shigella, Yersinia, Parabacteroides, Odoribacter, Faecalibacteria, Collinsella, Eggerthella, Lactonifactor, Pediococcus, Leuconostoc, Lactococcus, Roseburia, Coliform, Bacillus, Franscicella, Acinetobacter, Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella*, and *Enterococcus*, preferably wherein said spectrum consists of less than 20 bacterial species, more preferably of less than 15 bacterial species, more preferably of less than 10 bacterial species, more preferably of less than 5 bacterial species, and most preferably of 1 bacterial species, optionally wherein said compound is selected from a Ca-channel inhibitor, Tribenoside, Telmisartan, Azathioprine, Mercaptopurine, Mifepristone, Montelukast, Fentiazac, Meclozine dihydrochloride, Carbenoxolone, Gliquidone, Alfacalcidol, Acarbose, Ethacrynic acid, Chlorpromazine hydrochloride, Cyclosporin A, Flufenamic acid, Aripiprazole, Idebenone, Thioguanosine, Thyroxine (L), Gemcitabine, Folic acid, Etretinate, Paclitaxel, Phenindione, Mometasone furoate, Azacytidine-5, Luteolin, Metixene hydrochloride, Protriptyline hydrochloride, Toltrazuril, Tolnaftate, Meclofenamic acid, Prenylamine lactate, pharmaceutically acceptable salts thereof, and derivatives thereof.

In the context of the present invention, compounds are defined as having a "broad activity" if they inhibit the growth of ≥10 out of 40 species tested. A compound is defined as having activity against a "narrow-spectrum" of species, if it targets <9 out of 40 species tested.

Further preferred is the afore-mentioned narrow-spectrum compound for use, wherein said bacterial species is selected from the genus *Clostridia*, preferably wherein said *Clostridia* are selected from the group consisting of *C. difficile, C. butyricum, C. perfringens, C. novyi, C. septicum, C. botulinum, C. tetani, C. haemolyticum, C. carnis, C. histolyticum, C. sordellii, C. septicum, C. tertium, C. sporogenes, C. ramosum, C. inocuum, C. paraputrificum, C. cadaveris, C. bifermentans, C. fallax*, and *C. clostridioforme*, or combinations thereof, preferably wherein said bacterial species is *C. difficile*.

Another preferred embodiment of the present invention then relates to the compound for use, wherein said compound is a Ca-channel inhibitor, preferably wherein said Ca-channel inhibitor is selected from a dihyropyridine, Fendiline hydrochloride, pharmaceutically acceptable salts thereof, and derivatives thereof, optionally wherein said dihyropyridine or said derivative thereof is selected from Lacidipine, Cilnidipine, Amlodipine, and pharmaceutically acceptable salts thereof.

Further preferred is a compound for use in the inhibition of the growth of a bacterial species, wherein said bacterial species is *C. perfringens*, preferably wherein said compound is selected from Alfacalcidol, Acarbose, Ethacrynic acid, Chlorpromazine hydrochloride, Cyclosporin A, Idebenone, Thioguanosine, Gemcitabine, Etretinate, Paclitaxel, Phenindione, Azacytidine-5, pharmaceutically acceptable salts thereof, and derivatives thereof.

Another preferred compound for use is a compound for use in the modification of the growth of bacterial cells of a bacterial species, wherein said bacterial species is *Fusobacterium nucleatum*, preferably wherein said compound is Luteolin, pharmaceutically acceptable salts thereof, or derivatives thereof.

A further preferred embodiment of the present invention then relates to a compound for use in the modification of the growth of bacterial cells of an enterotoxigenic strain of *Bacteroides fragilis*, preferably wherein said compound is selected from Metixene hydrochloride, Protriptyline hydrochloride, Toltrazuril, Acarbose, Ethacrynic acid, Tolnaftate, Cilnidipine, Meclofenamic acid, Prenylamine lactate, pharmaceutically acceptable salts thereof, and derivatives thereof.

Yet another aspect of the present invention relates to a compound for use, wherein said compound is for use in the modification of the growth of bacterial cells of a spectrum of bacterial species selected from Gram-positive bacteria, Gram-negative bacteria, *Enterobacter, Staphylococcus, Streptococcus, Pseudomonas, Escherichia, Salmonella, Helicobacter, Neisseria, Campylobacter, Chlamydia, Clostridia, Citrobacter, Vibrio, Treponema, Mycobacterium, Klebsiella, Actinomyces, Bacteroides, Bordetella, Borrelia, Brucella, Corynebacteria, Diplococcus, Fusobacterium, Leptospira, Listeria, Pasteurella, Proteus, Rickettsia, Shigella, Yersinia, Parabacteroides, Odoribacter, Faecalibacteria, Collinsella, Eggerthella, Lactonifactor, Roseburia, Coliform, Bacillus, Franscicella, Acinetobacter, Legionella, Actinobacillus, Coxiella, Kingella kingae, Haemophilus, Bifidobacteria, Mobiluncus, Prevotella, Akkermansia, Bilophila, Blautia, Coprococcus, Dorea, Eubacteria, Lactobacillus, Ruminococcus, Veillonella, Enterococcus,* wherein said spectrum comprises at least 5 bacterial species, preferably at least 10 bacterial species, more preferably at least 20 bacterial species, more preferably at least 40 bacterial species, most preferably at least 50 bacterial species.

A preferred compound for use according to the present invention is the aforementioned compound for use, wherein said spectrum of bacterial species comprises at least *Bacteroides caccae, Bacteroides fragilis enterotoxigenic, Bacteroides fragilis nontoxigenic, Bacteroides ovatus, Bacteroides thetaiotaomicron, Bacteroides uniformis, Bacteroides vulgatus, Bacteroides xylanisolvens, Blautia obeum, Clostridium bolteae, Clostridium difficile, Clostridium perfringens, Clostridium ramosum, Clostridium saccharolyticum, Collinsella aerofaciens, Coprococcus comes, Dorea formicigenerans, Eggerthella lenta, Eubacterium eligens, Eubacterium rectale, Fusobacterium nucleatum, Odoribacter splanchnicus, Parabacteroides distasonis, Parabacteroides merdae, Prevotella copri, Roseburia hominis, Roseburia intestinalis, Ruminococcus bromii, Ruminococcus gnavus, Ruminococcus torques, Streptococcus parasanguinis, Streptococcus salivarius,* and *Veillonella parvula,* preferably wherein said compound is Diacerin, pharmaceutically acceptable salts thereof, and derivatives thereof.

Another preferred compound for use according to the present invention is a compound for use in the modification of the growth of bacterial cells of a spectrum of bacterial species, wherein said spectrum of bacterial species comprises at least *Bacteroides fragilis nontoxigenic, Bacteroides ovatus, Bacteroides uniformis, Clostridium difficile, Clostridium perfringens, Odoribacter splanchnicus, Parabacteroides distasonis, Parabacteroides merdae, Streptococcus parasanguinis,* and *Streptococcus salivarius,* preferably wherein said compound is Dicumarol, pharmaceutically acceptable salts thereof, and derivatives thereof.

Further preferred is a compound for use in the modification of the growth of bacterial cells of a spectrum of bacterial species, wherein said spectrum of bacterial species comprises at least *Blautia obeum, Clostridium perfringens, Clostridium ramosum, Clostridium saccharolyticum, Collinsella aerofaciens, Coprococcus comes, Dorea formicigenerans, Eubacterium eligens, Eubacterium rectale, Lactobacillus paracasei, Roseburia hominis, Roseburia intestinalis, Ruminococcus bromii, Ruminococcus gnavus,* and *Ruminococcus torques,* preferably wherein said compound is Clemizole hydrochloride, pharmaceutically acceptable salts thereof, and derivatives thereof.

Additionally, another preferred compound for use according to the present invention is a compound for use in the modification of the growth of bacterial cells of a spectrum of bacterial species, wherein said spectrum of bacterial species comprises at least *Bacteroides fragilis enterotoxigenic, Bacteroides ovatus, Bifidobacterium adolescentis, Bifidobacterium longum, Blautia obeum, Clostridium perfringens, Collinsella aerofaciens, Coprococcus comes, Dorea formicigenerans, Eubacterium eligens, Eubacterium rectale, Lactobacillus paracasei, Roseburia intestinalis, Ruminococcus bromii,* and *Ruminococcus torques,* preferably wherein said compound is Loratadine, pharmaceutically acceptable salts thereof, and derivatives thereof.

Another preferred compound for use according to the present invention is a compound for use in the modification of the growth of bacterial cells of a spectrum of bacterial species, wherein said spectrum of bacterial species comprises at least *Bacteroides fragilis nontoxigenic, Blautia obeum, Clostridium difficile, Clostridium perfringens, Clostridium ramosum, Coprococcus comes, Eubacterium rectale, Prevotella copri, Roseburia intestinalis, Ruminococcus bromii, Ruminococcus gnavus, Ruminococcus torques,* and *Streptococcus salivarius,* preferably wherein said compound is Troglitazone, pharmaceutically acceptable salts thereof, and derivatives thereof.

Further preferred is a compound for use in the modification of the growth of bacterial cells of a spectrum of bacterial species, wherein said spectrum of bacterial species comprises at least *Bacteroides ovatus, Bifidobacterium adolescentis, Blautia obeum, Clostridium difficile, Clostridium perfringens, Clostridium ramosum, Clostridium saccharolyticum, Coprococcus comes, Eggerthella lenta, Odoribacter splanchnicus, Parabacteroides distasonis, Parabacteroides merdae, Roseburia intestinalis,* and *Streptococcus salivarius,* preferably wherein said compound is Tiratricol, pharmaceutically acceptable salts thereof, and derivatives thereof.

Additionally, another preferred compound for use is a compound for use in the modification of the growth of bacterial cells of a spectrum of bacterial species, wherein said spectrum of bacterial species comprises at least *Bacteroides thetaiotaomicron, Bacteroides vulgatus, Blautia obeum, Clostridium bolteae, Clostridium perfringens, Collinsella aerofaciens, Dorea formicigenerans, Eubacterium eligens, Eubacterium rectale, Parabacteroides distasonis, Parabacteroides merdae, Roseburia intestinalis, Ruminococcus gnavus,* and *Streptococcus salivarius,* preferably wherein said compound is Bepridil hydrochloride, pharmaceutically acceptable salts thereof, and derivatives thereof.

Further preferred is a compound for use in the modification of the growth of bacterial cells of a spectrum of bacterial species, wherein said spectrum of bacterial species comprises at least *Bacteroides caccae, Bacteroides fragilis enterotoxigenic, Bacteroides fragilis nontoxigenic, Bacteroides vulgatus, Clostridium perfringens, Coprococcus comes, Eubacterium rectale, Parabacteroides merdae, Prevotella copri, Ruminococcus bromii,* and *Ruminococcus torques,* preferably wherein said compound is Estradiol Valerate, pharmaceutically acceptable salts thereof, and derivatives thereof.

Additionally, another preferred compound for use is a compound for use in the modification of the growth of bacterial cells of a spectrum of bacterial species, wherein said spectrum of bacterial species comprises at least *Bacteroides fragilis nontoxigenic, Bacteroides vulgatus, Blautia obeum, Clostridium bolteae, Clostridium difficile, Clostridium perfringens, Coprococcus comes, Eggerthella lenta, Odoribacter splanchnicus, Parabacteroides merdae,* and *Veillonella parvula*, preferably wherein said compound is Anthralin, pharmaceutically acceptable salts thereof, and derivatives thereof.

Further preferred is a compound for use in the modification of the growth of bacterial cells of a spectrum of bacterial species, wherein said spectrum of bacterial species comprises at least *Bacteroides caccae, Bacteroides fragilis* enterotoxigenic, *Bacteroides fragilis* nontoxigenic, *Bacteroides vulgatus, Bifidobacterium longum, Blautia obeum, Parabacteroides distasonis, Roseburia hominis, Roseburia intestinalis*, and *Veillonella parvula*, preferably wherein said compound is Aprepitant, pharmaceutically acceptable salts thereof, and derivatives thereof.

Another preferred compound for use is a compound for use in the modification of the growth of bacterial cell of a spectrum of bacterial species, wherein said spectrum of bacterial species comprises at least *Bacteroides vulgatus, Bifidobacterium longum, Blautia obeum, Collinsella aerofaciens, Coprococcus comes, Eubacterium eligens, Eubacterium rectale, Prevotella copri, Roseburia hominis*, and *Roseburia intestinalis*, preferably wherein said compound is Amiodarone hydrochloride, pharmaceutically acceptable salts thereof, and derivatives thereof.

Additionally, another preferred compound for use is a compound for use in the modification of the growth of bacterial cells of a spectrum of bacterial species, wherein said spectrum of bacterial species comprises at least *Bacteroides caccae, Bacteroides fragilis* enterotoxigenic, *Bacteroides fragilis* nontoxigenic, *Bacteroides ovatus, Bacteroides thetaiotaomicron, Bacteroides uniformis, Bacteroides vulgatus, Bacteroides xylanisolvens, Odoribacter splanchnicus, Parabacteroides distasonis*, and *Parabacteroides merdae*, preferably wherein said compound is Ethopropazine hydrochloride, pharmaceutically acceptable salts thereof, and derivatives thereof.

Further preferred is a compound for use in the modification of the growth of bacterial cells of a spectrum of bacterial species, wherein said spectrum of bacterial species comprises at least *Akkermansia muciniphila, Blautia obeum, Coprococcus comes, Dorea formicigenerans, Eubacterium eligens, Eubacterium rectale, Prevotella copri, Roseburia intestinalis, Ruminococcus gnavus*, and *Ruminococcus torques*, preferably wherein said compound is Astemizole, pharmaceutically acceptable salts thereof, and derivatives thereof.

Another preferred compound for use is a compound for use in the modification of the growth of bacterial cells of a spectrum of bacterial species, wherein said spectrum of bacterial species comprises at least *Bifidobacterium longum, Blautia obeum, Collinsella aerofaciens, Eubacterium eligens, Eubacterium rectale, Odoribacter splanchnicus, Parabacteroides distasonis, Prevotella copri, Roseburia hominis*, and *Roseburia intestinalis*, preferably wherein said compound is Methiothepin maleate, pharmaceutically acceptable salts thereof, and derivatives thereof.

A further embodiment then relates to the compound for use of the present invention, wherein said compound is enhancing the growth of bacterial cells of bacterial species selected from *Lactobacillus, Bifidobacterium, Enterococcus, Streptococcus, Pediococcus, Leuconostoc, Bacillus, Eschericha, Lactococcus*, or combinations thereof.

It is a further aspect of this invention to provide a pharmaceutical composition for use in the prevention and/or treatment of a disease in a subject and/or in the modification of the composition of the microbiome of a subject, comprising i) At least one compound according to the present invention; and
ii) A pharmaceutically acceptable additive, carrier, diluent, solvent, filter, lubricant, excipient, binder, and/or stabilizer.

The object of this invention is also solved by providing a method for modifying the growth of bacterial cells, the method comprising administering to a subject an effective amount of the afore-described compound for use, or the afore-described pharmaceutical composition, thereby modifying the growth of bacterial cells, wherein said modifying is preferably an inhibition or an enhancement of the growth of said bacterial cells, optionally wherein said method prevents and/or treats a disease in a subject and/or modifies the composition of the microbiome of said subject, preferably wherein said method modifies the composition of the microbiome of said subject, thereby preventing a disease in said subject.

The invention will now be described further in the following examples with reference to the accompanying figures, nevertheless, without being limited thereto. For the purposes of the present invention, all references as cited are incorporated by reference in their entireties.

FIG. 1 shows the systematic profiling of the effects of marketed drugs on a representative panel of human gut microbial species. a. Broad impact of pharmaceuticals on the human gut microbiota. Compounds of the Prestwick Chemical Library are divided into drugs used in humans, exclusively in animals (veterinary) and compounds not primarily used for medical/veterinary purposes (non-drugs). Human-use drugs are further categorized according to their target organism into "bacteria" (antibacterial drugs—green), "other pathogens" (viruses, fungi and protozoan/metazoan parasites, summarized as other anti-infective drugs—blue) and "human" (human-targeted drugs—orange). When a drug significantly reduced the growth of a specific strain within a set of 40 representative gut microbiome strains, the strain-drug pair in the matrix is highlighted with a vertical colored bar. Bacterial strains are sorted on the y-axis according to their drug sensitivity, increasing from bottom to top. Relative abundances of each strain in four cohort studies of healthy individuals are displayed on the right (boxes correspond to interquartile range and vertical line to median relative abundance). b. Fraction of drugs with anticommensal activity. The four main drug categories from a (same color code) are further subdivided according to human and veterinary use, and the anti-infectives further according to target or use. Grey scale within bars denotes inhibition spectrum, that is the number of affected strains per drug; each bar is subdivided in as many parts as drugs with anticommensal activity within that group. c. Correlation between species abundance in the human microbiome and species sensitivity to drugs. For each strain, the number of drugs from each of the three medically relevant categories impacting its growth is plotted against its median relative abundance in the human gut microbiome (colors as in a & b). Lines depict the best linear fit, rS the Spearman correlation and grey shade the 95% confidence interval of the linear fit. All drugs, and in particular human-targeted drugs inhibit the growth of abundant species more.

Figure 2:
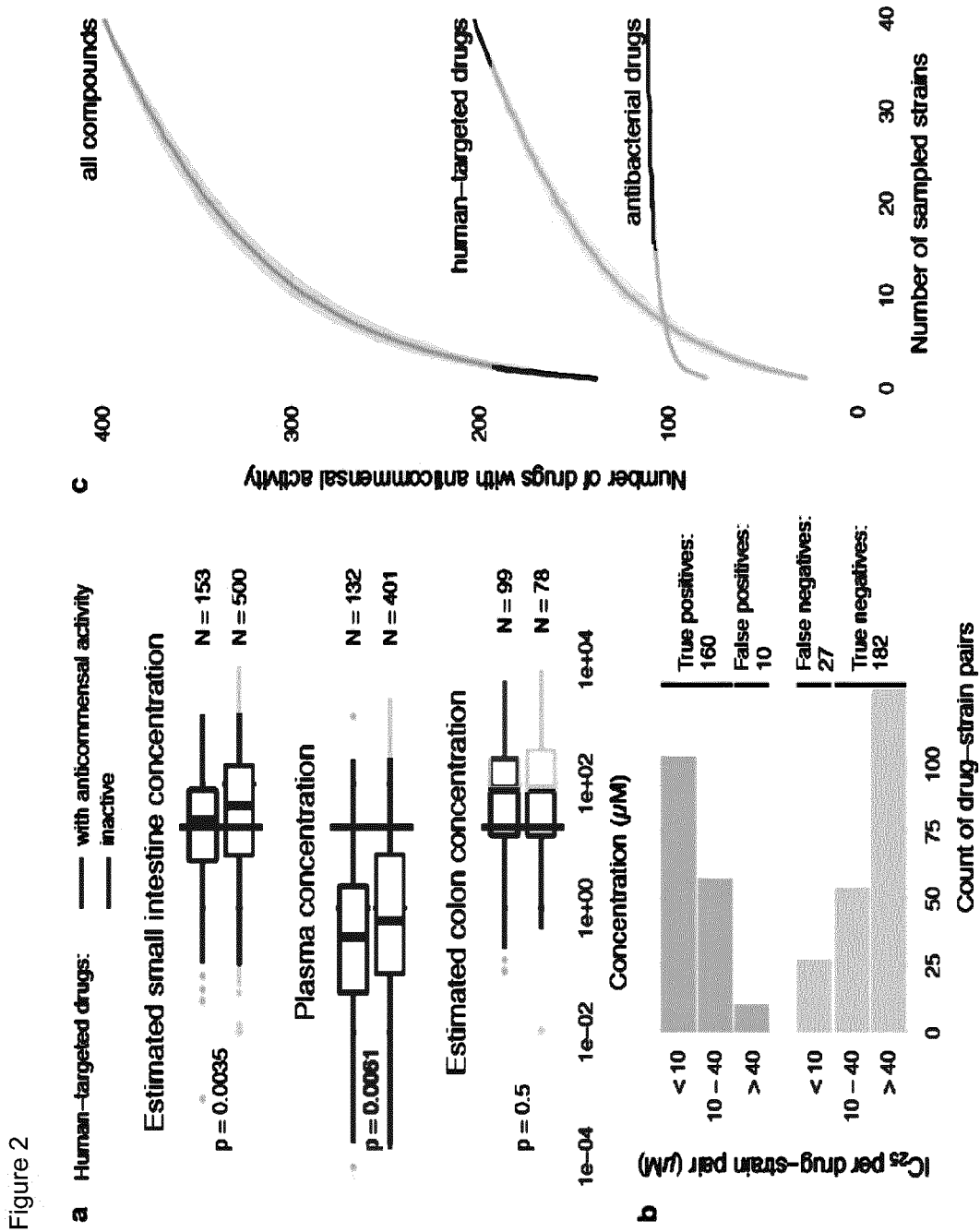

FIG. 2 shows the evaluation of human-targeted drugs with anticommensal activity. a. Estimated small intestine and colon concentrations, as well as measured plasma concentrations for human-targeted drugs with (orange) and without (grey) anticommensal activity in the inventor's screen. For both active and inactive compounds, the median estimated small intestine and colon concentrations are higher than the 20 μM used in the screen (black vertical lines), whereas plasma concentrations are lower. Non-hits in the inventor's screen generally reach higher plasma and small intestine concentrations (Wilcoxon rank sum test). b. IC25 determination for 25 selected drugs (color code as in a), purchased from independent vendors, in a subset of up to 27 strains validates the quality of the screen: precision (94%) and recall (85%). The inventors considered IC25 as the lowest concentration that reduces growth by >25%. Since inhibitory concentration calculations are known to have a two-fold error margin 85 and hit-calling in screen and 1025 validation are slightly different, the inventors considered an 1025 of 10-40 μM as being in agreement with the screening result. A higher number of false negatives implies that likely more human-targeted drugs have anticommensal activity. c. Rarefaction analysis indicates that anticommensal activity would be discovered for more human-targeted drugs if the inventors screened additional strains to the 40 probed here. In contrast, all antibiotics with anticommensal activity in the Prestwick Chemical Library have likely been identified.

Figure 3:
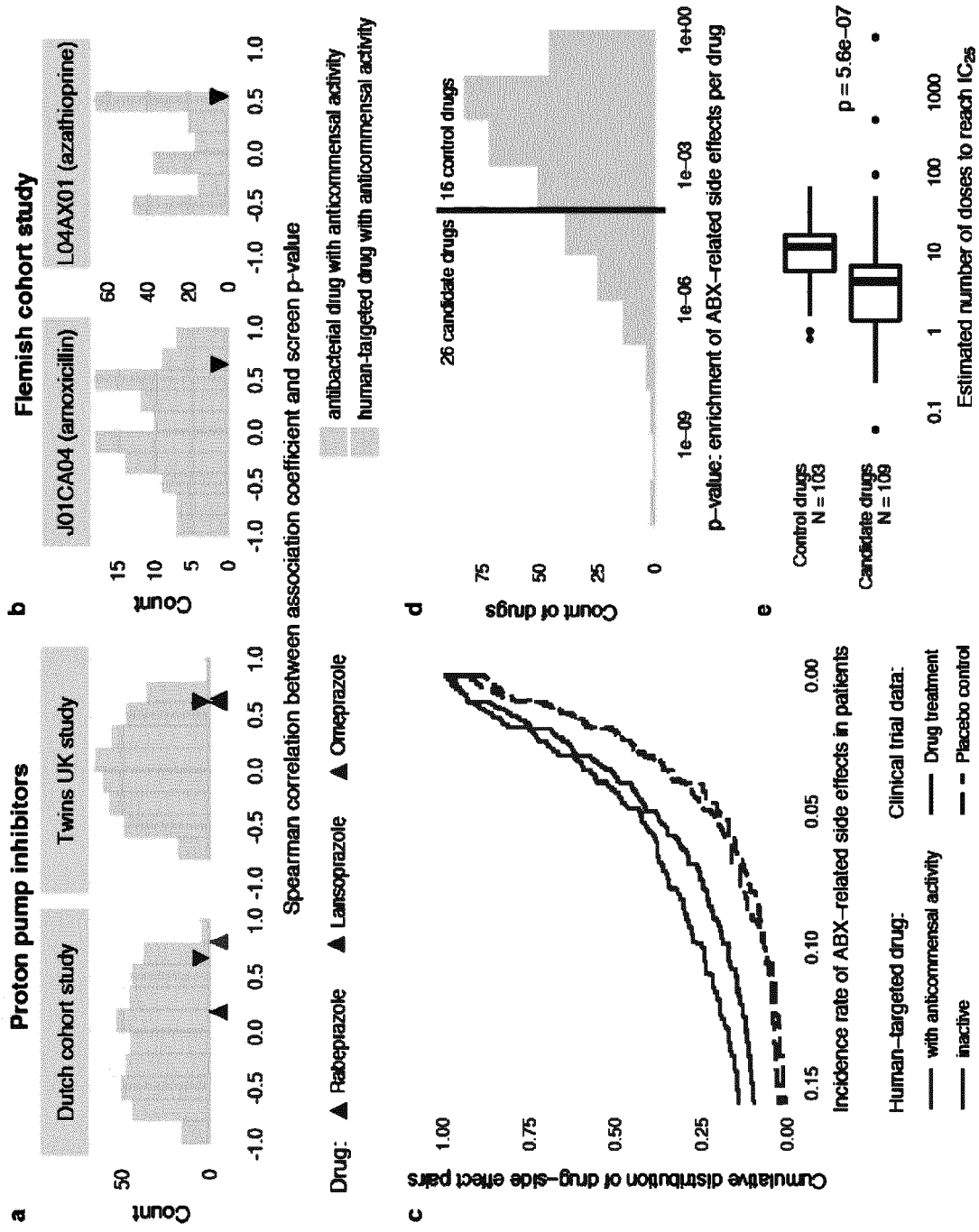

FIG. 3 shows that the anticommensal activity of human-targeted drugs in vitro reflects patient data. a. Changes in microbiome composition of patients taking proton pump inhibitors (PPIs) are in agreement with effects of PPIs in the inventor's screen. Displayed are Spearman correlation coefficients between in vitro growth inhibition p-values and changes in taxonomic relative abundances after consumption of PPIs for corresponding taxa from two cohort studies (Twins UK cohort, 229/1827 individuals had taken PPIs; and 3 independent cohorts from the Netherlands, 211/1815 individuals had taken PPIs). The histogram represents the background distribution of all correlations between the in vitro data for human-targeted drugs and the in vivo response to PPIs. For both studies, the three PPIs screened (omeprazole, lansoprazole and rabeprazole; highlighted by triangles) are among the top correlated human-targeted drugs. b. Spearman correlation coefficients between association coefficients of fecal microbiome composition after consumption of amoxicillin or azathioprine as reported in the Flemish cohort study and the screen p-values. Correlations are very high for amoxicillin or azathioprine (black triangles) compared to correlations for other antibacterial or human-targeted drugs, respectively. c. Human-targeted drugs with anticommensal activity in the inventor's screen had a significantly higher incidence of antibiotic-related side effects (orange trace shows cumulative distribution, N=285 drug-side effect pairs) in clinical trials compared to drugs without activity (grey trace, N=767; p=0.002, Wilcoxon rank sum test). Thus, anticommensal activity captured by the inventor's screen manifests as microbiota-related side effects in humans. Dashed lines indicate the incidence of the same side effects upon placebo treatment, for which there is no significant difference between active (N=138) and inactive drugs (N=474). d. Based on similarity to antibiotic-related side effects (vertical black line depicts prediction threshold), the inventors selected 26 candidate and 16 control drugs for testing for anticommensal activity at higher concentrations. e. Although both candidate and control drugs inhibited bacterial growth at higher concentrations, candidate drugs had anticommensal activity at significantly lower doses than control drugs (p=5.6e-7, two-sided Wilcoxon rank sum test). This demonstrates that anticommensal activity can be predicted from side effects.

Figure 4:
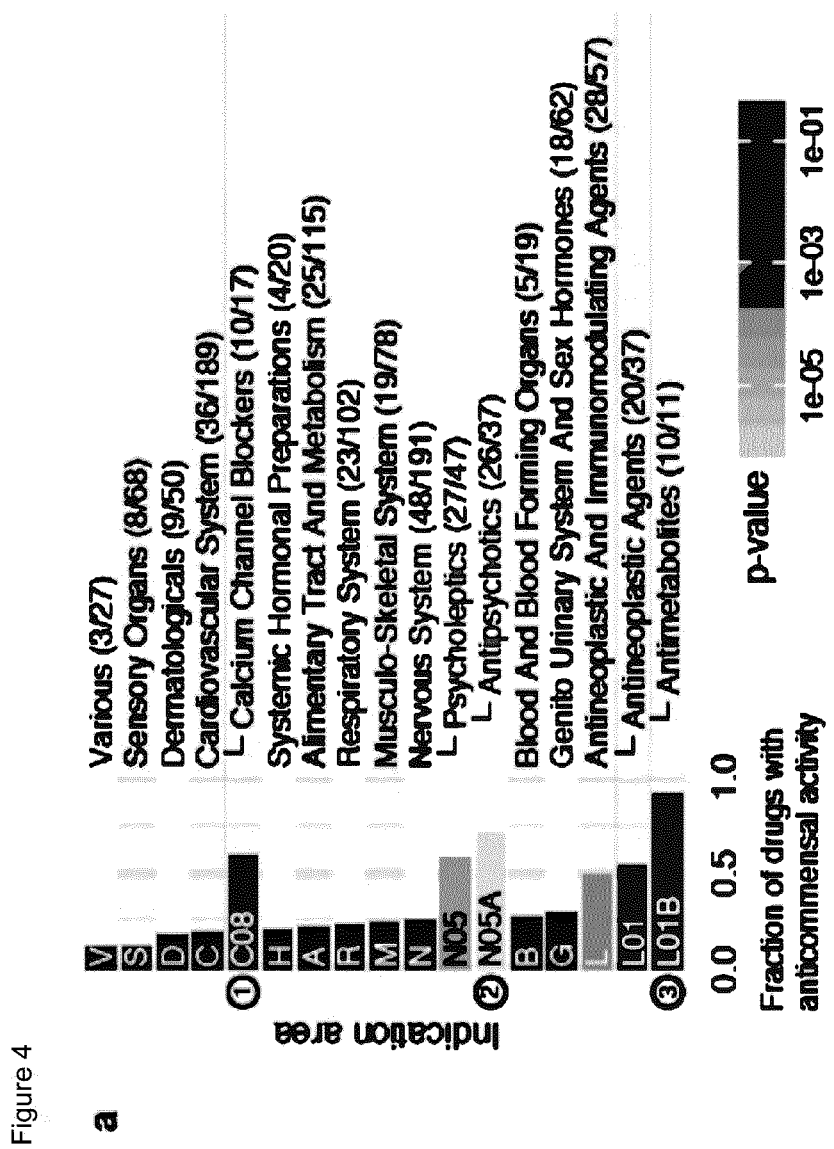
Figure 4:
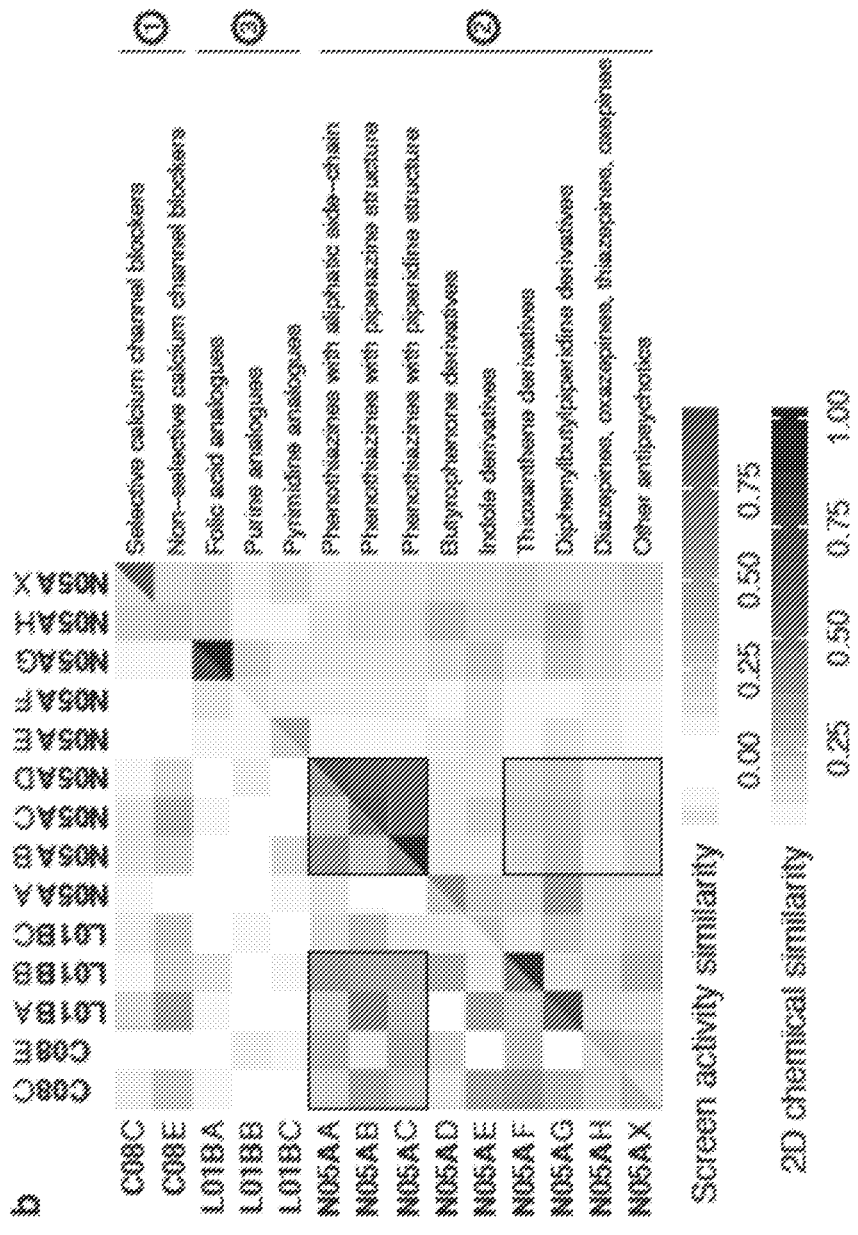
Figure 4:
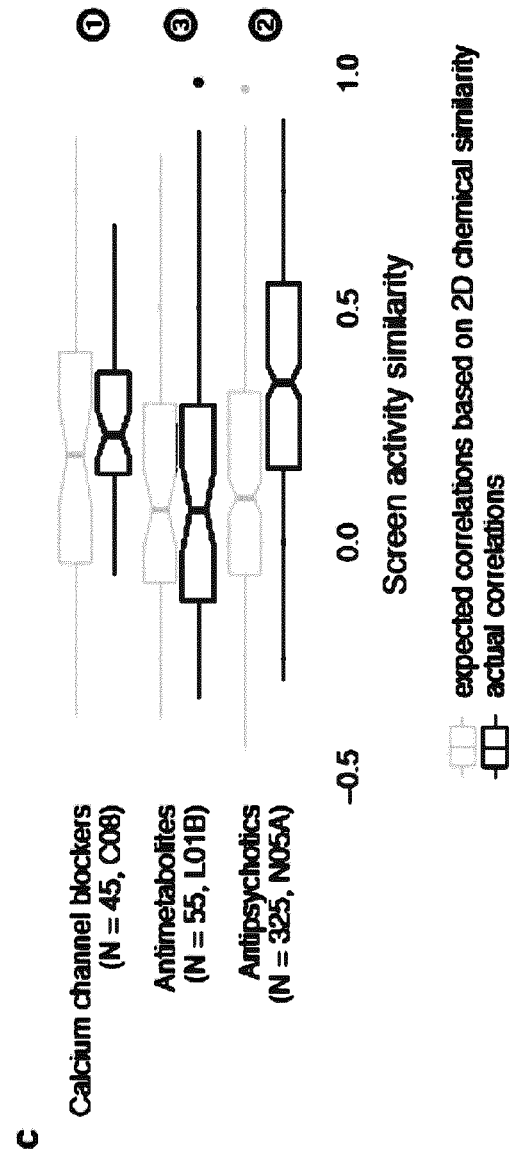

FIG. 4 shows drug therapeutic class and chemical properties influence anticommensal activity. a. Fraction of drugs with anticommensal activity by indication area according to the ATC classification scheme (bars). All first-level indication areas and significantly enriched lower levels are shown. Significance (p-value, Fischer's exact test) is indicated by the bar color and controlled for multiple hypothesis testing (Benjamini-Hochberg) independently at each hierarchy level of the ATC. b. Heat map of anticommensal activity and chemical similarities of human-targeted drugs within the three significantly ATC indication levels from a. Colors represent the median of drug pairwise Spearman correlations within and between subgroups depicted, calculated from the growth profiles of the 40 strains in each drug (p-values) or their Tanimoto scores. Examples of structurally similar (phenothiazines; N05AA-AC) and diverse (N05AF-AX) antipsychotics that all elicit similar responses in the inventors' screen are marked. c. Antipsychotics exhibit higher similarity in gut microbes they target than that expected based on their structural similarity (p-value=2e-19; other classes depicted show no significance difference).

Figure 5:
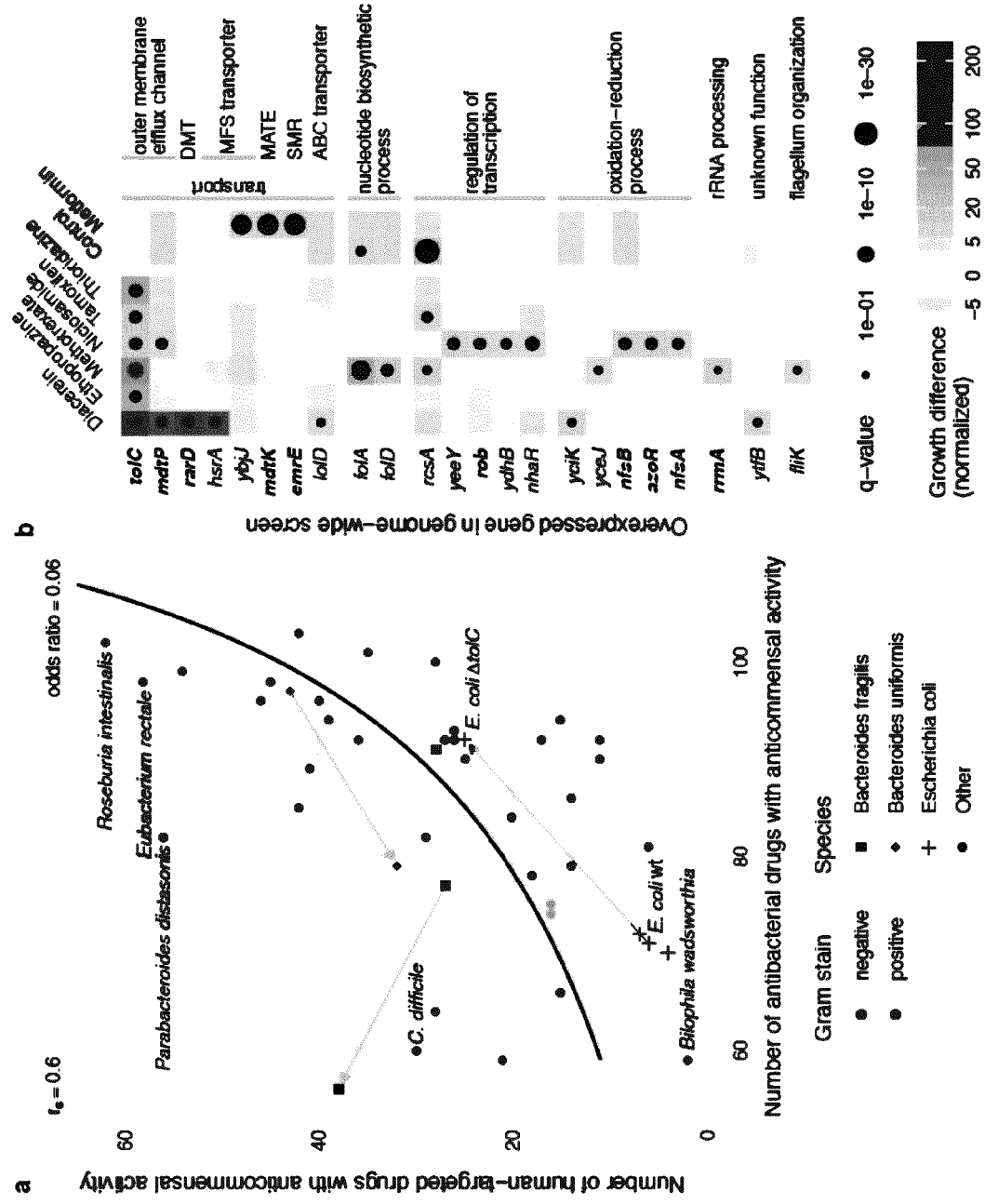

FIG. 5 shows antibiotic resistance mechanisms protect against human-targeted drugs. a. For each of the 40 strains tested, colored here according to Gram-staining, number of human-targeted drugs that inhibit its growth are plotted against the number of antibiotics the strain is sensitive to. Susceptibility to antibacterials and human-targeted drugs correlates across species (Spearman correlation, rS=0.6 and a line depicting the nonlinear least-squares estimate of the odds ratio, OR=0.06), suggesting common resistance mechanisms against both types of drugs. Black dots denote the lab E. coli strain, BW25113 (behaving similar with the other 2 commensal E. coli strains, which are part of the screen), and its ΔtolC derivative. Knocking out this major antibiotic efflux pump, tolC, makes E. coli equally more sensitive to both antibacterials and human-targeted drugs. b. Chemical genomics of an E. coli genome-wide overexpression library in 6 human-targeted drugs and the antiparasitic niclosamide; all screens except for metformin were performed in ΔtolC background to sensitize E. coli to these drugs. Genes that when overexpressed, improve significantly the growth of E. coli to at least one of the drugs are shown here. Genes previously associated with antibiotic resistance are shown in bold. Among them, genes encoding for transporters from different families are illustrated—abbreviations for families are as following: DMT (drug metabolite transporter), MFS (major facilitator superfamily), MATE (multidrug and toxin extrusion), SMR (small multidrug resistance) and ABC (ATP-binding cassette). Growth is measured by colony size, color depicts the normalized size difference from the median growth of all strains in the drug, and dot size the significance of effect (FDR-corrected p values). Control denotes the growth of the library without drug.

Figure 6:
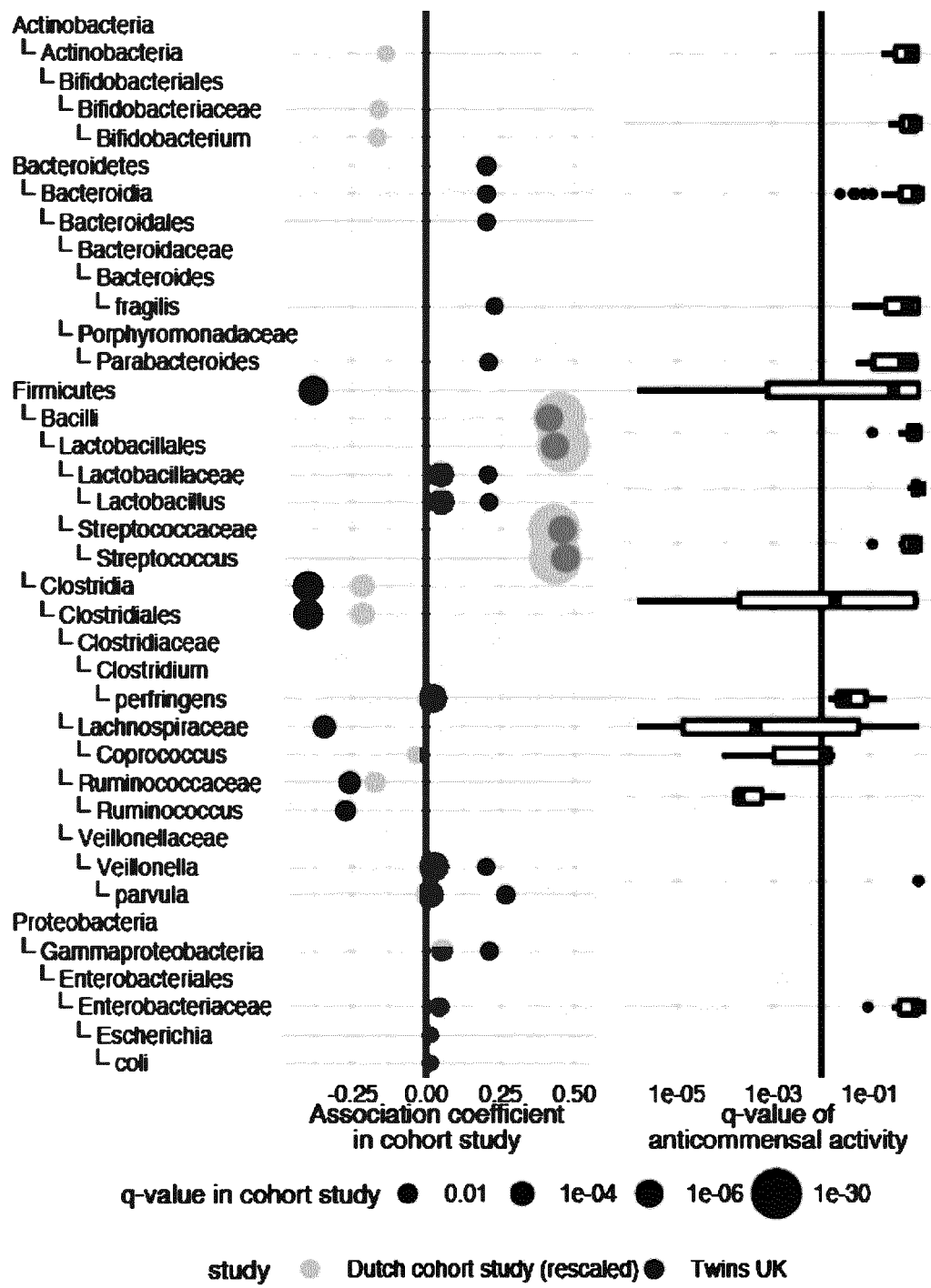
Figure 6:
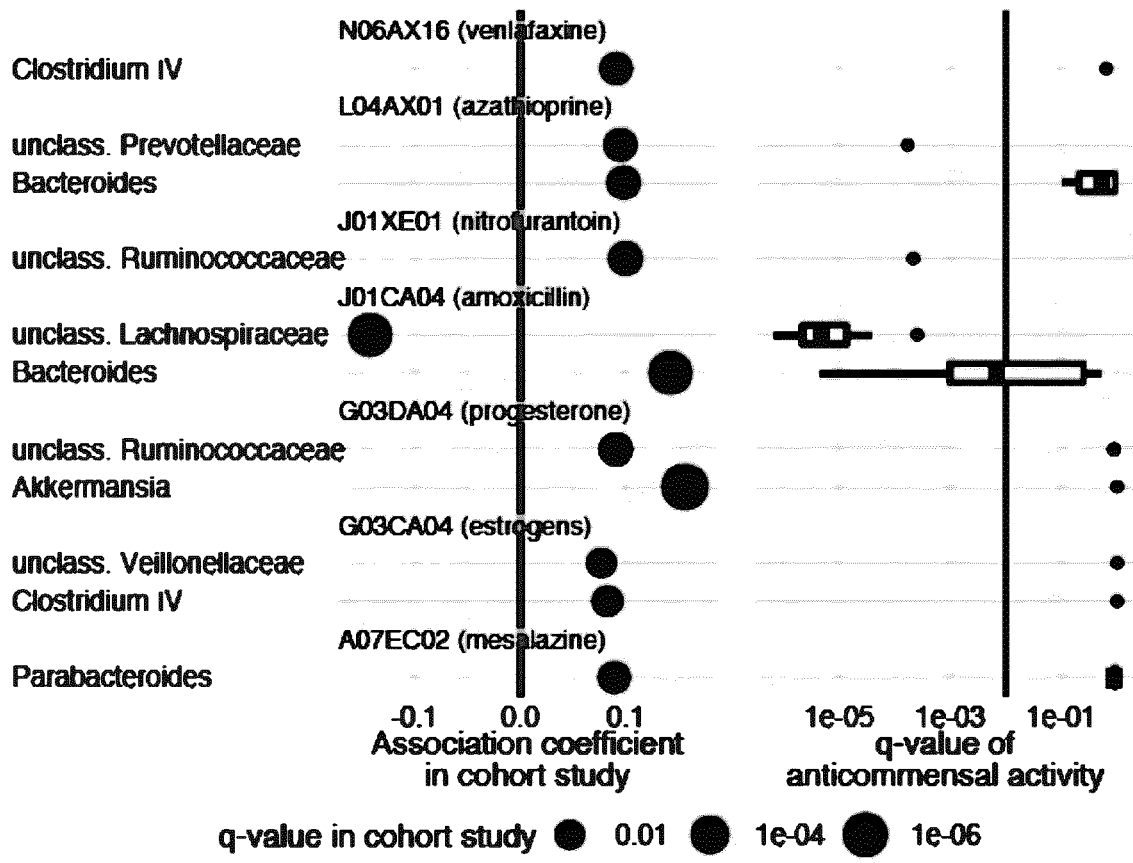
Figure 6:
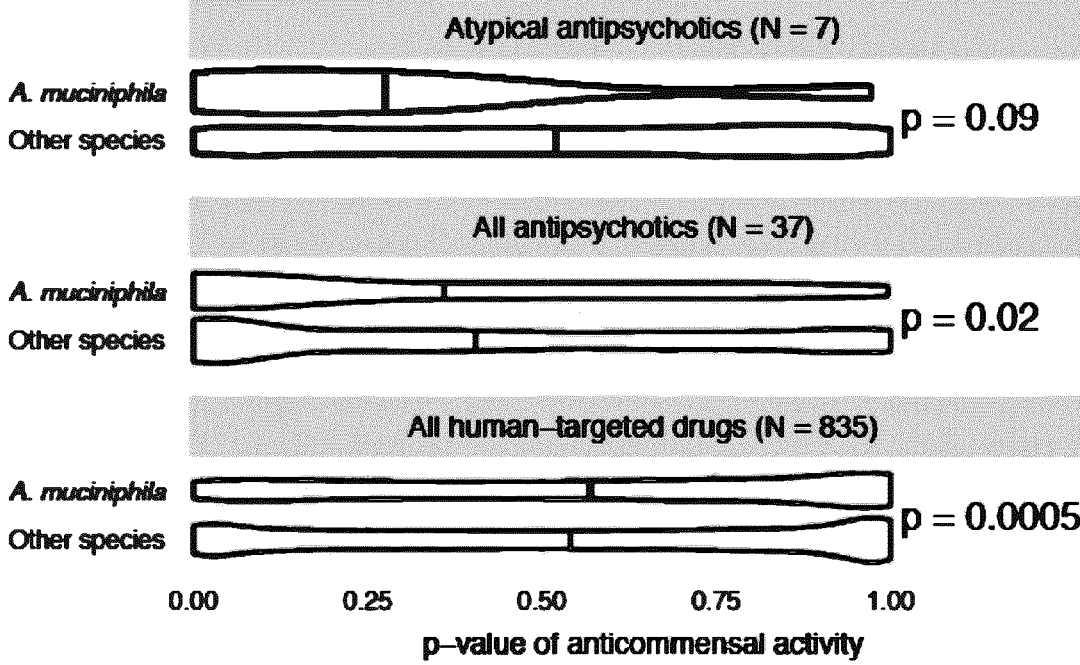

FIG. 6 shows the concordance of drug in vitro species susceptibilities and drug-mediated shifts in microbiome composition of patients. a. Association coefficients between PPI usage and relative taxonomical abundance in fecal microbiomes of PPI users from two studies (twins, UK cohort—green; and 3 independent cohorts from the Netherlands—blue) (left) are compared to in vitro growth inhibition of isolates with same taxonomic rank in the presence of PPIs (omeprazole, lansoprazole and rabeprazole) as accessed by FDR adjusted p-values (q-values) in the inventor's screen (right). Reduced taxa in patients (negative association coefficient, left to vertical black line) were mostly inhibited by PPIs in the inventor's screen (q-value below 0.01, left to vertical black line), while enriched taxa were insensitive to PPIs. b. Comparisons between association coefficients and drugs from different therapeutic classes as assessed by Falony et al. and the inventor's in vitro data.

c. A bipolar disease cohort study 6 reported a significantly decrease in abundance of *Akkermansia* upon atypical antipsychotics (AAP) treatment. Comparing distributions of adjusted p-values from the inventor's screen for different strains, *Akkermansia muciniphila* was significantly more sensitive than all other strains to antipsychotics in general and AAP in particular (p=0.02 and p=0.09, one-sided Wilcoxon rank sum test). In contrast, *A. muciniphila* is relatively more resistant than other strains across all human-targeted drugs (p=0.0005, one-sided Wilcoxon rank sum test).

Figure 7:
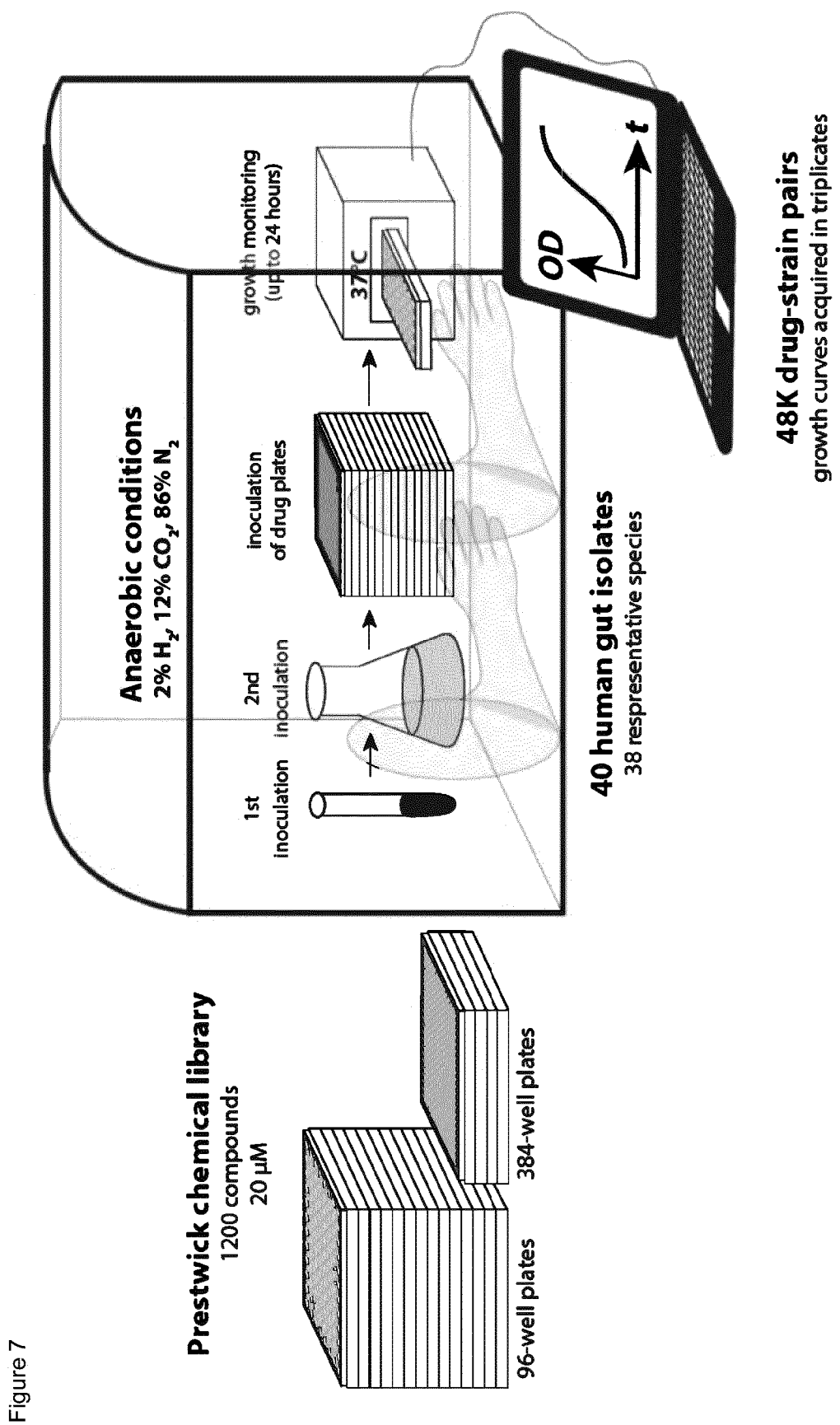

FIG. 7 shows a schematic overview of the experimental set-up of the screen. Drugs from the Prestwick Chemical Library (arranged in either 96- or 384-well format) were diluted in growth media (for most part mGAM) and pre-reduced in a Coy anaerobic chamber before inoculation with one out of 40 different human gut microbes. Bacterial growth was monitored for 16-24 hours at 37° C. Growth curves were acquired at least in triplicates for each drug-microbe interaction.

Figure 8:
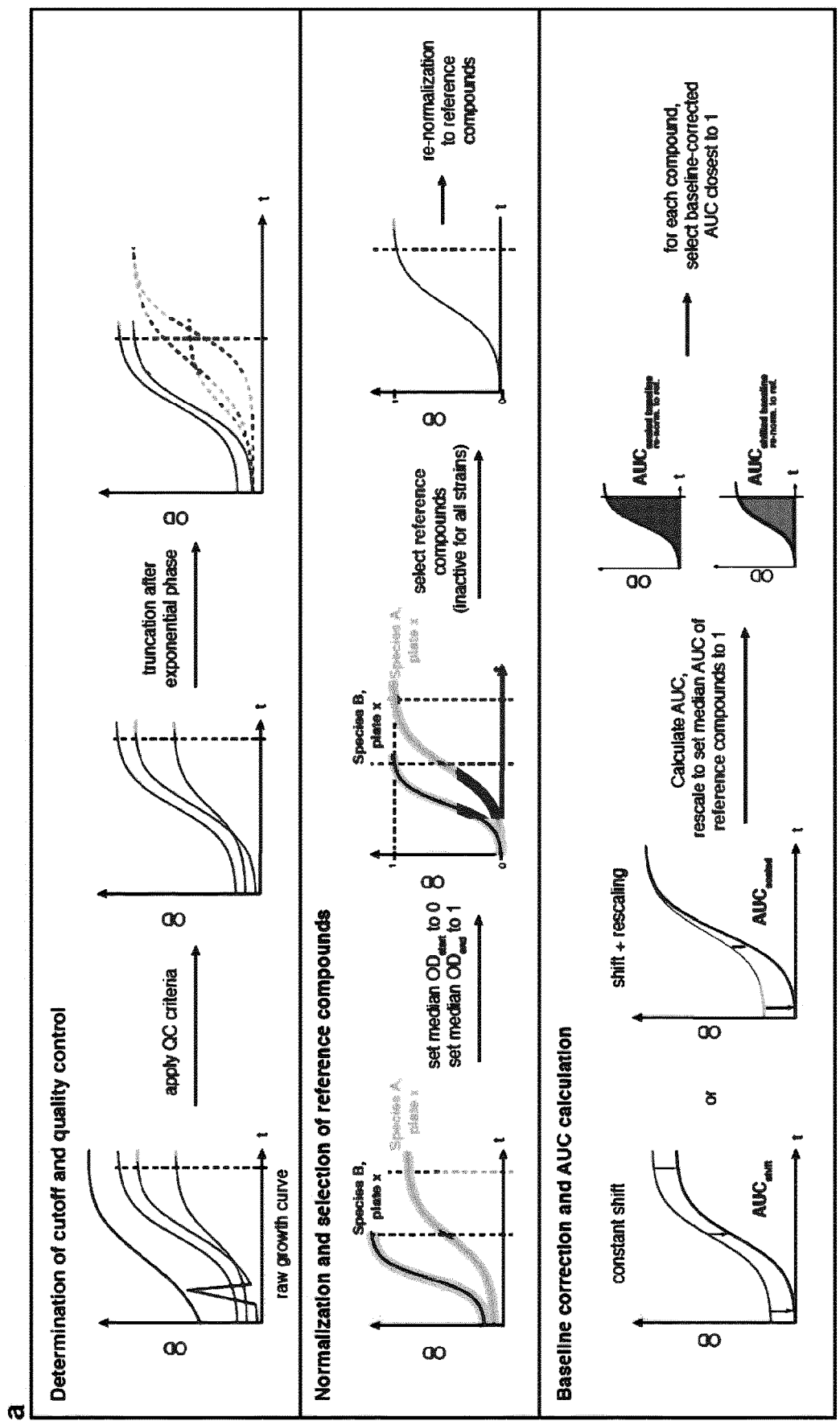
Figure 8:
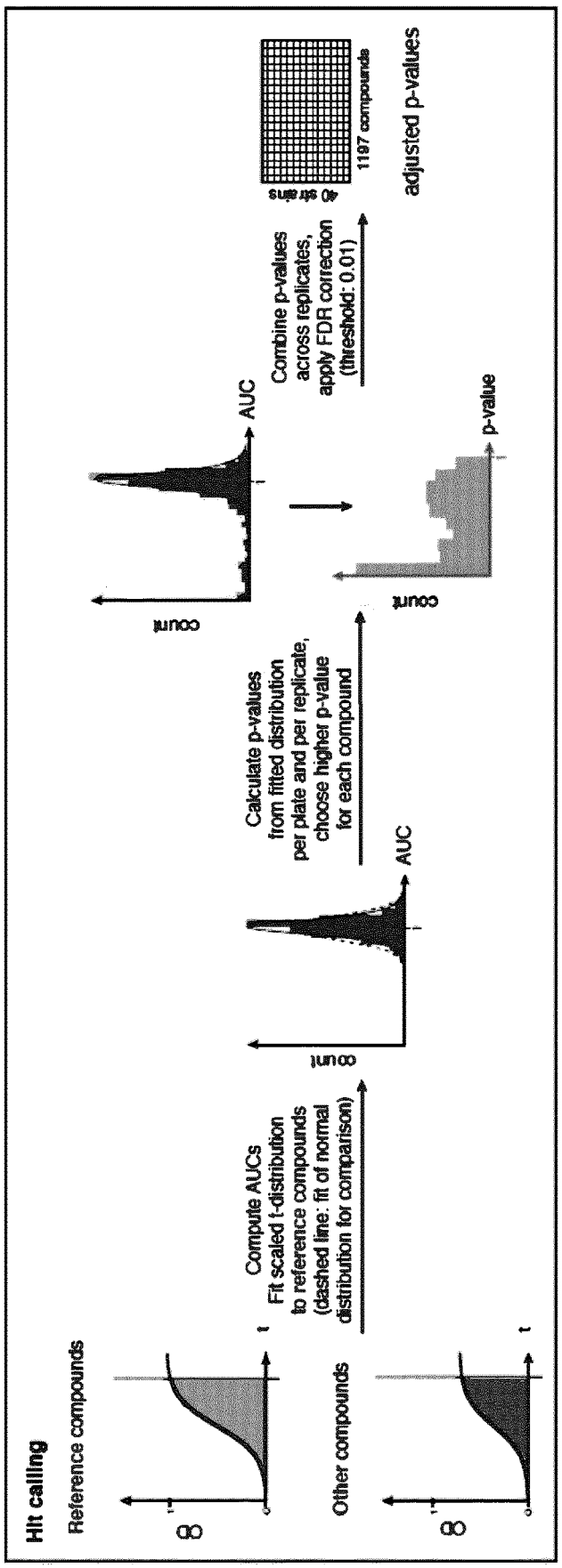
Figure 8:
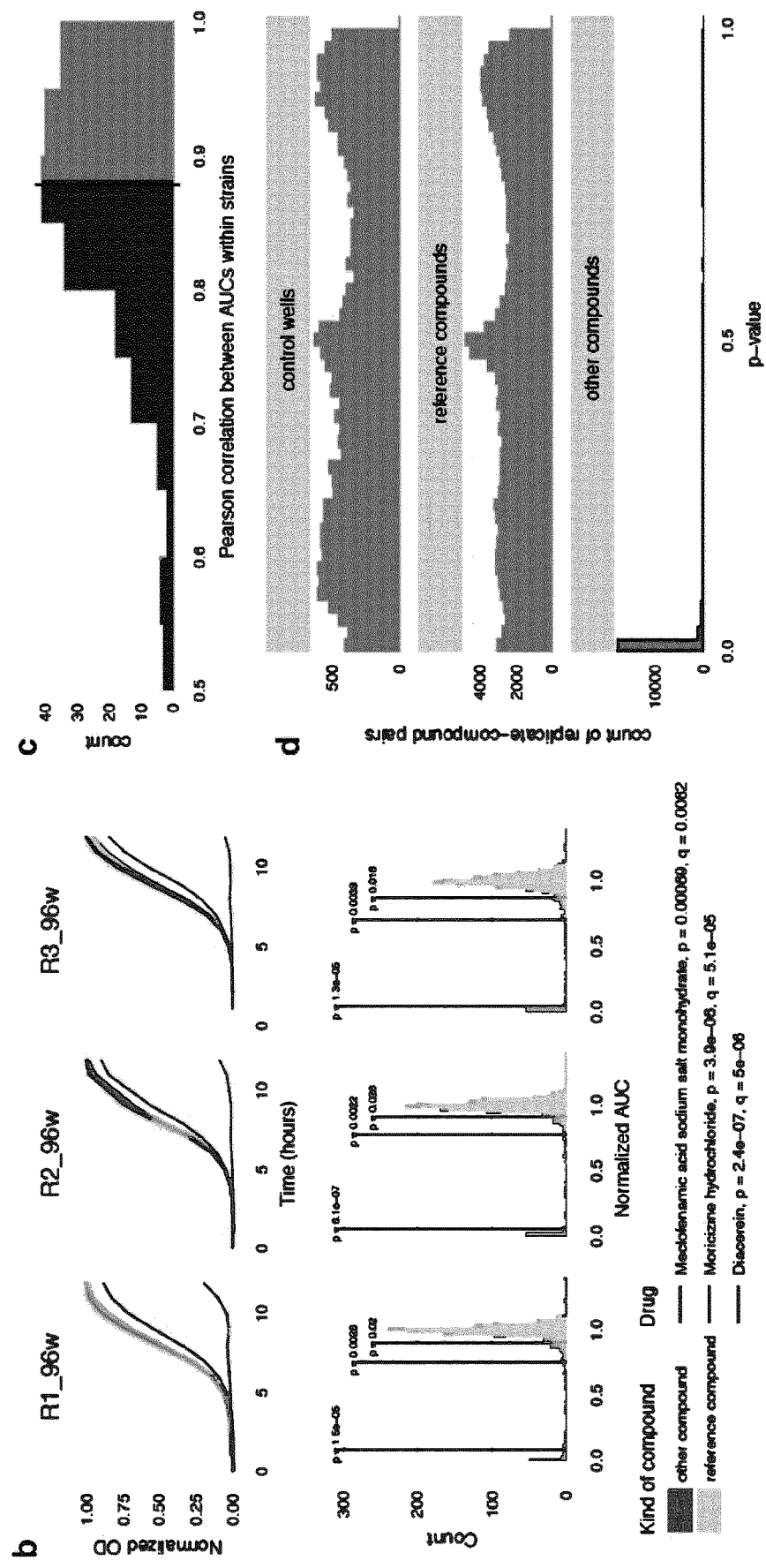

FIG. 8 shows data analysis pipeline for identifying compounds with anticommensal activity. a. Schematic overview of the data analysis pipeline. All steps (determination of time cutoff and removal of noisy points; normalization and selection of reference compounds; baseline correction, AUC calculation and hit calling) are explained in detail below. On first panel dashed lines on plot on the right depict the three possible effects that a drug can have on the growth of a microbe: increase the lag phase, decrease the growth rate or the stationary phase plateau. All effects are captured by cutting off the growth curves upon transition to stationary phase for most compounds (most drugs do not affect growth). On second panel, median growth rates for two drugs on same plate are depicted and normalized, whereas baseline correction (third panel) is applied at the individual wells. b. Growth curves (normalized OD) of *Bacteroides ovatus* in three exemplary drug cases for the three biological replicates (upper panel)—meclofenamic acid (red), moricizine (green) and diacerein (blue). Light and dark grey shades represent the 50% and 90% confidence intervals for normal growth. Normalized AUC histograms for all drugs in the three biological replicates for the case of *B. ovatus*. Meclofenamic acid is just below the hit threshold, moricizine is a hit with partial but strong growth inhibition, and diacerein almost completely inhibits the growth of *B. ovatus*. c. For most species, correlation between replicates is very high (median: 0.89). d. For both controls and reference compounds, p-values were approximately uniformly distributed. Determining the background distribution of uninhibited growth using reference compounds is validated by their very similar behavior with control wells. Other drugs (i.e. drugs not used as reference compounds) show a clear enrichment of low p-values.

Figure 9:
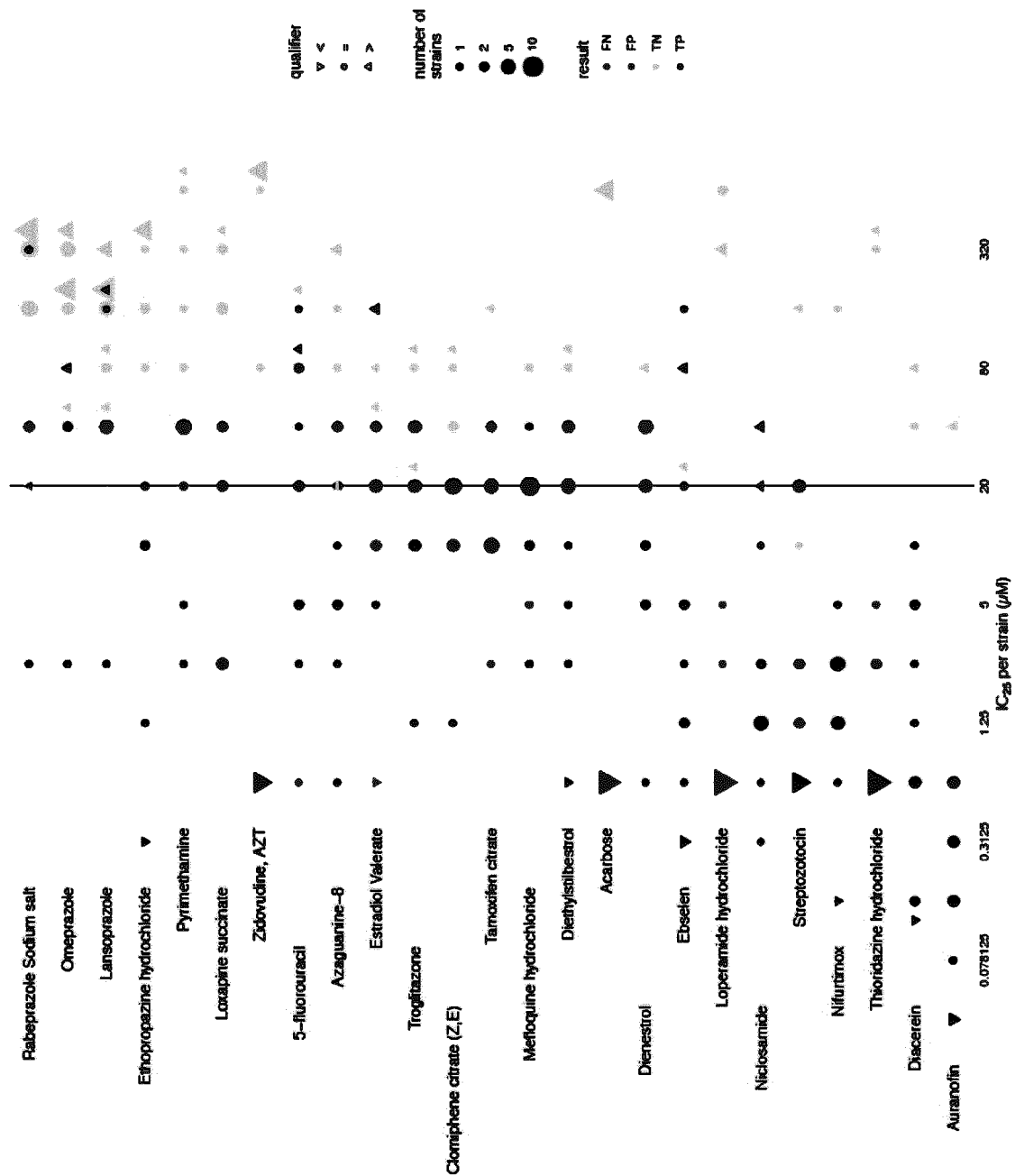

FIG. 9 shows IC25's for the validation screen. IC25's of 25 drugs were determined in up to 27 individual strains to validate the inventor's screen. The white area indicates the drug concentration ranges tested for each drug. Symbol sizes depict number of strains with a particular IC25, symbol colors indicate categorization into false negatives (FN), false positives (FP), true negatives (TN) or true positives (TP) and symbol shapes qualify whether actual IC25s were determined or 1025 was deemed to be higher or lower from the highest and lowest concentration tested, respectively. Vertical line indicates the drug concentration used in the inventor's screen (20 μM). Particular drugs were responsible for FNs in the inventor's screen (acarbose, loperamide, thioridazine), presumably due to drug decay.

The term "microbiota" refers, collectively, to the entirety of microbes found in association with a higher organism, such as a human. Organisms belonging to a human's microbiota may generally be categorized as bacteria, archaea, yeasts, and single-celled eukaryotes, as wells as viruses and various parasites.

The term "microbiome" refers, collectively, to the entirety of microbes, their genetic elements (genomes), and environmental interactions, found in association with a higher organism, such as a human.

The microbiome comprises many probiotic bacterial strains. The term "probiotic" as used herein means living microorganisms, which when administered in adequate amounts, confer a health benefit on the host. Probiotics may be available in foods and dietary supplements (for example, but not limited to capsules, tablets, and powders). Example of food containing probiotics are yogurt, fermented and unfermented milk, miso, tempeh, and some juices and soy beverages. Some bacterial strains of the microbiome are known to have a probiotic function, such as *Lactobacillus, Bifidobacterium, Enterococcus, Streptococcus, Pediococcus, Leuconostoc, Bacillus, Escherichia*, and *Lactococcus*.

The term "commensal" refers to organisms that are normally harmless to a host, and can also establish mutualistic relations with the host. The human body contains about 100 trillion commensal organisms, which have been suggested to outnumber human cells by a factor of 10.

The term "compound" as used herein is used to describe any specific compound or bioactive agent disclosed herein, including any and all stereoisomers (including diasteromers) if applicable, individual optical isomers (enantiomers) or racemic mixtures, pharmaceutically acceptable salts, prodrug forms, including hydrates and solvates of these compounds. The term compound herein refers to stable compounds. Within its use in context, the term compound may refer to a single compound or a mixture of compounds as otherwise described herein.

The term "disease" in the context of the present invention shall refer to any disease or condition indicated as negatively affecting, in any kind of way, a human being. In a specific embodiment, said disease is selected from an infectious disease, a gastrointestinal disorder, an inflammatory disease, a proliferative disease, a metabolic disorder, a cardiovascular disease, and an immunological disease.

The term "infection", as used herein, relates to the presence of bacteria, viruses, fungi, protozoa or other microorganisms, in or on a subject as well as the invasion by bacteria, viruses, fungi, protozoa or other microorganisms. The invasion includes undesired proliferation of pathogenic microbes in a host organism. More generally, a microbial infection can be any situation in which the presence of a microbial population(s) is damaging to a host animal. Thus, a microbial infection exists when excessive microorganisms are present in or on a mammal's body, or when the effects of the presence of a microbial population(s) is damaging the cells or other tissues of a mammal. Thus, the inhibition of the growth of such invading microorganisms results in a benefit to the subject that is infected by the microbial population(s). Examples of bacterial infections are, without being limited thereto, gastrointestinal infections, urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, *Chlamydia*, skin infections, and bacteremia.

Two types of bacteria can be differentiated based on structural differences in their cell walls, Gram-positive and Gram-negative bacteria. In the method developed by Hans Christian Gram, some bacteria retain a crystal violet dye due to a thick layer of peptidoglycan in their cell walls. These bacteria are referred to as Gram-positive bacteria. In contrast, Gram-negative bacteria do not retain the crystal violet dye and are colored red or pink in the test developed by Gram.

*Acinetobacter* is a genus of aerobic, Gram-negative bacteria belonging to the wider class of *Gammaproteobacteria*. *Acinetobacter* species are not motile, oxidase-negative, and occur in pairs. *Acinetobacter* species are a key source of infection in debilitated patients in the hospital, in particular the species *Acinetobacter baumannii*.

*Actinomyces* is a genus of Gram-positive actinobacteri, which are facultatively anaerobic (except *A. meyeri*, a strict anaerobe). Individual bacteria are rod-shaped, while *Actinomyces* colonies form fungus-like branched networks of hyphae. *Actinomyces* species are normally present in the gums and are the most common cause of infection in dental procedures and oral abscesses. Many *Actinomyces* species are opportunistic pathogens of humans and other mammals, particularly in the oral cavity. In rare cases, these bacteria can cause *actinomycosis*, a disease characterized by the formation of abscesses in the mouth, lungs, or the gastrointestinal tract. *Actinomycosis* is most frequently caused by *Actinomyces israelii*.

*Bacteroides* is a genus of Gram-negative, obligate anaerobic bacteria. *Bacteroide* species are non-endospore-forming bacilli, and may be either motile or non-motile, depending on the species. Some species, such as *B. fragilis*, are opportunistic human pathogens. *B. fragilis* is the main cause of infections of the peritoneal cavity, infections that occur after gastrointestinal surgery, and appendicitis via abscess formation. Although *Bacteroide* species are anaerobic, they are transiently aerotolerant and thus can survive in areas such as the abdominal cavity.

*Neisseria* are Gram-negative bacteria, belonging to proteobacteria. They colonize the mucosal surfaces of many animals. The main pathogenic *Neisseria* species are *N. meningitidis* and *N. gonorrhoeae*.

*Chlamydia* is a genus of pathogenic bacteria that are obligate intracellular parasites. *Chlamydia* infections are the most common bacterial sexually transmitted diseases in humans and are the leading cause of infectious blindness worldwide.

*Vibrio* is a genus of Gram-negative bacteria, possessing a curved-rod shape. Multiple *Vibrio* species can cause foodborne infections, usually associated with eating undercooked seafood.

*Treponema* is a genus of spiral-shaped bacteria. The major pathogenic *Treponema* species is *Treponema pallidum*, causing diseases such as syphilis, bejel, and yaws.

*Mycobacterium* is a genus of *Actinobacteria*, given its own family, the Mycobacteriaceae. They are aerobic and non-motile bacteria (except for the species *Mycobacterium marinum*, which has been shown to be motile within macrophages). Mycobacteria have an outer membrane, possess capsules, and most do not form endospores.

*Bordetella* is a genus of small (0.2-0.7 µm), Gram-negative coccobacilli of the phylum Proteobacteria.

*Alistipes* is a genus in the phylum *Bacteroidetes*.

*Borrelia* is a genus of bacteria of the spirochete phylum. *Borrelia* cause borreliosis, a zoonotic, vector-borne disease transmitted primarily by ticks and lice.

*Brucella* is a genus of Gram-negative bacteria. They are small, non-encapsulated, non-motile and facultatively intracellular coccobacilli.

*Diplococci* are round bacteria (forming a coccus) that typically occur in the form of two joined cells. *Diplococci* can be Gram-negative and Gram-positive.

*Leptospira* is a genus of spirochaete bacteria, including a small number of pathogenic and saprophytic species.

*Alistipes* is a genus in the phylum *Bacteroidetes*.

*Desulfovibrio* is a genus of Gram-negative sulfate-reducing bacteria. *Desulfovibrio* species are commonly found in aquatic environments with high levels of organic material, as well as in water-logged soils. They are major community members of extreme oligotrophic habitats such as deep granitic fractured rock aquifers.

*Listeria* are gram-positive, rod-shaped, and facultatively anaerobic bacteria, which do not produce endospores.

*Pasteurella* is a genus of Gram-negative, facultatively anaerobic bacteria. *Pasteurella* are non-motile and pleomorphic, and often exhibit bipolar staining.

*Rickettsia* is a genus of non-motile, Gram-negative, non-spore-forming, highly pleomorphic bacteria that can be present as cocci (0.1 µm in diameter), rods (1-4 µm long), or thread-like forms (10 µm long).

*Shigella* is a genus of Gram-negative, facultative anaerobic, non-spore-forming, non-motile, rod-shaped bacteria genetically closely related to *E. coli*.

*Parabacteroides* is a Gram-negative, anaerobic, non-spore-forming genus from the family of Porphyromonadaceae.

The genus *Odoribacter* derives its name from its rod shape and foul odor it produces in the mouth of dogs. Bacteria within this genus are atypical opportunistic pathogens, anaerobic, Gram-negative, non-spore-forming, and non-motile.

*Faecalibacterium* is a genus of bacteria. Its sole known species, *Faecalibacterium prausnitzii* is one of the most abundant and important commensal bacterium of the human gut microbiota.

*Collinsella* is a genus of *Actinobacteria*, belonging in the family of Coriobacteriaceae.

*Eggerthella* is a bacterial genus of *Actinobacteria*, in the family Coriobacteriaceae. Members of this genus are anaerobic, non-sporulating, non-motile, Gram-positive bacilli that grow singly, as pairs, or in short chains.

*Roseburia* is a genus of butyrate-producing, Gram-positive anaerobic bacteria that inhabit the human colon. They are members of the phylum firmicutes.

*Coliform* bacteria are defined as rod-shaped Gram-negative non-spore forming bacteria, which can ferment lactose with the production of acid and gas when incubated at 35-37° C.

*Bacillus* is a genus of gram-positive, rod-shaped bacteria and a member of the phylum Firmicutes. *Bacillus* species can be obligate aerobes, or facultative anaerobes.

*Desulfovibrio* is a genus of Gram-negative sulfate-reducing bacteria. *Desulfovibrio* species are commonly found in aquatic environments with high levels of organic material, as well as in water-logged soils. They are major community members of extreme oligotrophic habitats such as deep granitic fractured rock aquifers.

*Butyrivibrio* is a genus of bacteria in the class of *Clostridia*. Bacteria of this genus are common in the gastrointestinal systems of many animals.

*Akkermansia* is a genus in the phylum Verrucomicrobia. *Akkermansia* are oval-shaped, non-motile and Gram-negative bacteria, which are strictly anaerobic and chemo-organotrophic.

*Bilophila* are Gram-negative anaerobic rod-forming bacteria. These bacteria carry out fermentation within the gut using taurine as the final electron acceptor. They are urease-positive, bile resistant, catalase-positive, and are largely found in patients that have appendicitis.

*Blautia obeum* is a species of Gram-positive bacteria found in the gut. *B. obeum* is an anaerobe.

*Coprococcus* is a genus of anaerobic cocci, which are part of the human faecal flora.

*Dorea* is a genus of Clostridiaceae.

*Eubacterium* is a genus of Gram-positive bacteria in the family of Eubacteriaceae. These bacteria are characterized by a rigid cell wall.

*Lactobacillus* is a genus of Gram-positive, facultative anaerobic or microaerophilic, rod-shaped, non-spore-forming bacteria. Many *Lactobacilli* are known to be very effective probiotic bacterial species. *Lactobacillus acidophilus* is the most well-known probiotic and one of the most important for the health of the small intestine. Besides the lining of the intestine, *Lactobacillus acidophilus* can also take up residence in the vagina, cervix or urethra. Acidophilus inhibits pathogens, and produces natural antibiotics such as lactocidin and acidophilin, which enhance immunity. *Lactobacillus acidophilus* has anti-microbial effects against *Staphylococcus aureus, salmonella, E. coli* and *Candida albicans*.

*Lactobacillus brevis* is a lactic acid producing probiotic that is helpful in synthesizing Vitamins D and K.

*Lactobacillus bulgaricus*, used in yogurt fermentation, plays a protective role by producing lactic acid, which creates a friendly environment for other species.

*Lactobacillus plantarum* makes lactolin, another natural antibiotic. *Lactobacillus plantarum* can also synthesize L-lysine, an anti-viral amino acid. This organism eliminates nitrate, promoting nitric oxide levels and decreases pathogens.

*Lactobacillus rhamnosus* has a high tolerance to bile salts, surviving in less than favorable environments. This species has shown to be beneficial to the elderly and infants alike. *Lactobacillus rhamnosus* lowers the symptoms of lactose intolerance, protects the small intestine, and produces lactic acid in the large intestine. Other strains of *Lactobacilli* include *Lactobacillus fermentum, Lactobacillus caucasicus, Lactobacillus helveticus, Lactobacillus lactis, Lactobacillus reuteri* and *Lactobacillus casei*.

*Ruminococcus* is a genus of bacteria in the class of *Clostridia*. They are anaerobic, Gram-positive gut microbes. *Ruminococci* are found in significant numbers in the intestines of humans.

*Veillonella* are Gram-negative anaerobic cocci. These bacteria are well known for their lactate fermenting abilities. They are common bacteria in the intestines and oral mucosa of mammals.

*Francisella tularensis* is a pathogenic species of Gram-negative, rod-shaped coccobacillus, an aerobe bacterium. It is non-spore forming, non-motile and the causative agent of tularemia, the pneumonic form of which is often lethal without treatment.

The genus *Legionella* is a pathogenic group of Gram-negative bacteria. The species *L. pneumophila* causes legionellosis including a pneumonia-type illness called Legionnaires' disease and a mild flu-like illness called Pontiac fever.

*Actinobacillus* is a genus of Gram-negative, non-motile and non-spore-forming, oval- to rod-shaped bacteria occurring as parasites or pathogens in mammals, birds, and reptiles. They are members of the Pasteurellaceae family.

*Coxiella* refers to a genus of Gram-negative bacteria in the family Coxiellaceae.

*Kingella kingae* is a species of Gram-negative aerobic coccobacilli. They cause infections such as septic arthritis, osteomyelitis, spondylodiscitis, bacteraemia, and endocarditis, and less frequently lower respiratory tract infections and meningitis.

*Haemophilus* is a genus of Gram-negative, pleomorphic, coccobacilli bacteria belonging to the Pasteurellaceae family.

*Bifidobacterium* is a genus of Gram-positive, non-motile, often branched anaerobic bacteria. They are ubiquitous, endosymbiotic inhabitants of the gastrointestinal tract, vagina and mouth of mammals, including humans. *Bifidobacteria* are one of the major genera of bacteria that make up the colon flora in mammals. Some *Bifidobacteria* are also known to be probiotic. Of these, *Bifidobacterium bifidum* is the most recognized of this category. Living within the mucus lining of the large intestine and/or vaginal tract, *Bifidobacterium bifidum* prevents pathogenic bacteria and yeast from invading. *Bifidobacterium bifidum* creates favorable changes in pH levels by producing lactic and acetic acids. In addition, this species increases absorption of iron, calcium, magnesium and zinc. *Bifidobacterium infantis* simulates the production of cytokines that affect the immune system, and can kill off pathogens such as clostrida, *salmonella* and *shigella*. *Bifidobacterium longum* colonizes the large intestine and prevents unfriendly bacteria and yeast from taking residence. Accordingly, this can result in a reduction of the frequency of gastrointestinal problems, such as diarrhea, and nausea during antibiotic use.

*Campylobacter* is a genus of microaerophilic Gram-negative bacteria. *Campylobacter* are a significant cause of food poisoning due to handling of raw meat or undercooking meat. *Campylobacter* are motile, with either unipolar or bipolar flagella. The organisms have a characteristic spiral/corkscrew appearance and are oxidase-positive. *Campylobacter jejuni* is one of the main causes of bacterial foodborne disease in many developed countries. At least a dozen species of *Campylobacter* have been implicated in human diseases.

*Clostridium* is a genus of Gram-positive bacteria, which are obligate anaerobes capable of producing endospores. Individual bacterial cells are rod-shaped. The five main species responsible for diseases in humans are *C. botulinum* (it produces botulinum toxin in food/wound and can cause botulism), *C. difficile* (it can flourish when other bacteria in the gut are killed during antibiotic therapy, leading to pseudomembranous colitis, a cause of antibiotic-associated diarrhea), *C. perfringens* (also known as *C. welchii*, it causes a wide range of symptoms, from food poisoning to gas gangrene, and is also responsible for enterotoxemia), *C. tetani* (it is the causative organism of tetanus) and *C. sordellii* (it may cause a fatal infection in exceptionally rare cases after medical abortions).

*Corynebacterium* is a genus of Gram-positive, rod-shaped bacteria, widely distributed in nature and mostly innocuous.

*Enterococcus* is a genus of Gram-positive, lactic acid bacteria of the phylum Firmicutes. Important clinical infections caused by *Enterococcus* include urinary tract infections, bacteremia, bacterial endocarditis, diverticulitis, and meningitis. Of note, *Enterococcus faecium* has shown to have a probiotic effect. This organism can be advantageous for diarrhea, particularly by shortening the duration of symptoms. It has further been shown to kill pathogenic microbes, such as rotavirus.

*Fusobacterium* is a genus of anaerobic, Gram-negative bacteria, wherein individual cells are rod-shaped bacilli with pointed ends. *F. nucleatum* has been strongly associated with colorectal cancer, and there is evidence that antibiotic treatment in animal models for colorectal cancer reduces its load and delays disease onset.

*Helicobacter* is a genus of Gram-negative bacteria having a characteristic helix shape. *Helicobacter pylori* is a causative agent of gastric cancer.

*Mobiluncus* is a genus of gram-positive, anaerobic, rod-shaped bacteria. They are found in the human vagina, particularly in association with *Gardnerella vaginalis* in cases of bacterial vaginosis.

*Prevotella* is a genus of Gram-negative bacteria. *Prevotella* bacteria are members of the oral and vaginal flora and are recovered from anaerobic infections of the respiratory tract.

*Pseudomonas* is a genus of Gram-negative aerobic gammaproteobacteria.

*Staphylococcus* is a genus of Gram-positive bacteria, with round appearance, so-called cocci. *Staphylococcus* bacteria form in grape-like clusters.

*Streptococcus* is a genus of spherical Gram-positive bacteria belonging to the phylum Firmicutes and the lactic acid bacterial group. Some *Streptococci* are probiotic. For example, *Streptococcus thermophilus* is a probiotic used to make yogurt. Breaking down lactose to create lactase, the enzyme that digests milk sugars, this species can help with lactose intolerance. Other important *Streptococcus* strains include *cremoris, faecium* and *infantis*.

*Citrobacter* is a genus of Gram-negative *Coliform* bacteria in the Enterobacteriaceae family. The species *C. amalonaticus, C. koseri*, and *C. freundii* can use citrate as a sole carbon source.

*Enterobacter* is a genus of common Gram-negative, facultatively anaerobic, rod-shaped, non-spore-forming bacteria of the family Enterobacteriaceae. Examples of *Enterobacter* are *Escherichia coli, Salmonella typhimurium, Pseudomonas aeruginosa, Acinetobacter baumannii, Klebsiella pneumonia*, and *Stenotrophomonas maltophilia*.

*Escherichia* is a genus of Gram-negative, non-spore forming, facultatively anaerobic, rod-shaped bacteria from the family Enterobacteriaceae.

*Klebsiella* is a genus of non-motile, Gram-negative, oxidase-negative, rod-shaped bacteria with a prominent polysaccharide-based capsule, from the family Enterobacteriaceae.

*Proteus* is a genus of Gram-negative Proteobacteria, from the family Enterobacteriaceae.

*Salmonella* is a genus of rod-shaped, Gram-negative bacteria, from the family Enterobacteriaceae. There are only two species of *Salmonella, Salmonella bongori* and *Salmonella enterica*, of which there are around six subspecies. *Salmonella* cause illnesses such as typhoid fever, paratyphoid fever, and food poisoning. *Salmonella* species are facultative intracellular pathogens.

*Yersinia* is a genus of Gram-negative rod shaped bacteria from the family Enterobacteriaceae, which are facultative anaerobes. Some members of *Yersinia* are pathogenic in humans. In particular, *Y. pestis* is the causative agent of the plague. Rodents are the natural reservoirs of *Yersinia* and, less frequently, other mammals serve as the host. Infection may occur through blood, or via consumption of food products contaminated with infected urine or feces.

The term "MDR", as used in accordance with the present invention, refers to a multi drug resistant bacterial strain.

The term "dysbiosis" (also called dysbacteriosis) shall refer to any kind of imbalance of the microbiome. For example, species that are normally underrepresented in the microbiome of a healthy human being become overrepresented during the condition of dysbiosis, whereas normally dominated species of a healthy human being become underrepresented during the condition of dysbiosis. Most often, dysbiosis is a condition in the gastrointestinal tract, particularly during small intestinal bacterial overgrowth (SIBO) or small intestinal fungal overgrowth (SIFO). Dysbiosis has been reported to be associated with illnesses, such as inflammatory bowel disease, bacterial vaginosis, and colitis.

The term "gastrointestinal disorder" shall include any disturbance of the gastrointestinal tract. Examples of gastrointestinal disorders are, without being limited thereto, gastrointestinal motility disorder, irritable bowel syndrome, constipation, a functional gastrointestinal disorder, gastroesophageal reflux disease, functional heartburn, dysbiosis, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten and/or lactose intolerance, obesity, stomach rumble, small intestinal bacterial overgrowth (SIBO), small intestinal fungal overgrowth (SIFO), meteorism, and flatulence.

A "proliferative disease" in the context of the present invention shall preferably refer to a disease such as a cancer or a tumor disease. Cancer diseases that can be treated by the compound of the present invention include, but are not limited to, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma, pleomorphic adenoma, hepatocellular carcinoma, and/or adenocarcinoma. Of note, there is a correlation between antibacterial infections and certain cancers. As such, evidence suggests that gastric cancer can be caused by *Helicobacter pylori*. Above that, *Fusobacteria* (and presumably also other bacterial species) are contributing to colorectal cancer.

A medical "use" of the compounds of the invention shall preferably refer to a method for preventing or treating a disease in a subject, wherein the method comprises a step of administering to the subject a therapeutically effective amount of the compound.

Treatment is meant to include, e.g., treating, delaying or alleviating disease progression, reducing the symptoms of, or curing the disease or condition. An "effective amount" is an amount of the compound(s) or the pharmaceutical composition as described herein that alleviates symptoms as found for the disease to be treated, such as a cancer disease. Alleviating is meant to include, e.g., preventing, treating, reducing the symptoms of, or curing the disease or condition. The invention also includes a method for treating a subject at risk for a development and/or progression of a disease, wherein a therapeutically effective amount of a compound as described above is provided. Being at risk for the disease can result from, e.g., a family history of the disease, a genotype, which predisposes to the disease, or phenotypic symptoms, which predispose to the disease. In one embodiment, as used herein, the term "prevention" or "preventing" when used in the context of a subject refers to stopping, hindering, and/or slowing down the development or onset of a proliferative disease and in in particular the symptoms associated with the proliferative disease.

The term "antibiotic", as used herein, relates to a chemical substance which at low concentrations kills or prevents the growth of certain microorganisms, generally bacteria, although some antibiotics are also used for the treatment of infections by fungi or protozoa. Antibiotics are used in human, animal or horticultural medicine to treat infections caused by microorganisms. Antibiotics included in the present invention are, without being limited thereto, aminoglycoside antibiotics, ansamycins, carbacefems, carbapenems, cephalosporins, glycopeptides, glycylcyclines, macrolides, monobactams, penicillins, polypeptides, quinolones, fluoroquinolones, sulphonamides, beta-lactams, tetracyclines and others such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide antibiotics, polymixins, quinupristin/dalfopristin, rifampin, rifampicin, tinidazole, viomycin and capreomycin.

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled artisan, the route and/or mode of administration will vary depending upon the desired results. To administer a compound according to the invention by certain routes of administration, it may be necessary to co-administer a material to prevent inactivation or activation of the compount. For example, the compound may be administered to a subject in an appropriate carrier, or a diluent. Pharmaceutically acceptable diluents include saline and aqueous buffer solutions. A "pharmaceutically acceptable carrier" refers to an ingredient in a pharmaceutical formulation, other than an active ingredient, which is nontoxic to a subject. Pharmaceutically acceptable carriers includes any and all solvents, dispersion media, coatings, antibacterial and antifungal agents, isotonic and absorption delaying agents, and the like that are physiologically compatible.

The pharmaceutical compositions according to the invention may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient, which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and the like factors well known in the medical arts.

The composition must be sterile and fluid to the extent that the composition is deliverable by syringe. In addition to water, the carrier can be an isotonic buffered saline solution. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. The compositions of the invention may be administered locally or systemically. Administration will generally be parenterally, e.g., intravenously; the pharmaceutical composition may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

In the context of the present invention the term "subject", as used in certain embodiments, preferably refers to a mammal, such as a mouse, rat, guinea pig, rabbit, horse, cattle, cow, cat, dog, monkey, or preferably a human. The term "patient" preferably refers to a mammal, such as a mouse, rat, guinea pig, rabbit, horse, cattle, cow, cat, dog, monkey, or preferably a human, for example a human patient, for whom diagnosis, prognosis, or therapy is desired. The subject of the invention may be at danger of suffering from a disease, such as a bacterial infection, a viral infection, a fungal infection, and a parasitic infection. A more detailed description of medical indications relevant in context of the invention is provided herein elsewhere.

The term "treating" as used herein means stabilizing or reducing an adverse symptom associated with a condition; reducing the severity of a disease symptom; slowing the rate of the progression of a disease; inhibiting or stabilizing the progression of a disease condition; or changing a metric that is associated with the disease state in a desirable way.

The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, the term "salt" shall mean a pharmaceutically acceptable salt, solvate or polymorph consistent with the use of the compounds as pharmaceutical agents.

The term "pharmaceutically acceptable derivative" or "derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "effective" is used herein, unless otherwise indicated, to describe an amount of a compound or component which, when used within the context of its use, produces or effects an intended result, whether that result relates to the prophylaxis and/or therapy of a disease state, a secondary disease state or condition thereof or as otherwise described herein. The term effective subsumes all other effective amount or effective concentration terms (including the term "therapeutically effective") which are otherwise described or used in the present application.

The verb "to comprise" and its conjugations is used in its non-limiting sense to mean that items following the word are included, but combinations and/or items not specifically mentioned are not excluded. In addition, the verb "to consist" may be replaced by "to consist essentially of" meaning that a part (e.g. a compound, a part of a compound, a bacterial strain, a spectrum of bacterial strains) as defined herein may comprise additional component(s) than the ones specifically identified, said additional component(s) not altering the unique characteristic of the invention.

EXAMPLES

Bacterial Strains and Growth Conditions

Bacterial isolates used in this study were purchased from DSMZ, BEI Resources, ATCC and Dupont Health & Nutrition, or were gifts from the Denamur Lab (INSERM). All strains were recovered in their recommended rich media (resource and literature). The screen and validation experiments were performed in modified Gifu Anaerobic Medium broth (mGAM) (HyServe GmbH & Co.KG, Germany, produced by Nissui Pharmaceuticals), since almost all species could grow robustly in this medium in a manner that is reflective of their gut abundance. Only one strain was grown in Todd-Hewitt Broth (Sigma-Aldrich), one in a 1:1 mixture of mGAM and Gut Microbiota Medium and for one strain, mGAM was supplemented with 60 mM sodium formate and 10 mM taurine. All media were pre-reduced at least 1 day before use under anoxic conditions in an anaerobic chamber (Coy Laboratory Products Inc) (2% $H_2$, 12% $CO_2$, rest $N_2$) and all experiments were performed under anaerobic conditions at 37° C. unless specified otherwise.

To select a representative core of species in the human gut microbiome, the inventors analyzed 364 fecal metagenomes of asymptomatic individuals from 3 continents. Species were defined and their abundance quantified as previously described. A core set of 60 microbiome species was defined, and from this core, 31 species were selected for the screen of this invention. 7 additional species were selected which are of great interest.

Preparation of Screening Plates

The Prestwick Chemical Library was purchased from Prestwick Chemical Inc. (Illkirch, France) with compounds coming dissolved in dimethyl sulfoxide (DMSO) at a concentration of 10 mM. Compounds were re-arrayed to redistribute the DMSO control wells in each plate and to minimize the total number of 96- and 384-well plates (4×384-well plates or 14×96-well plates). At the same time, drugs were diluted to a concentration of 2 mM to facilitate further aliquoting, and these plates were stored at −30° C. For each experimental batch (10 replicates in 96-well plates; 20 replicates in 384-well plates) the inventors prepared drug plates in the respective growth medium (2× for 96-well plates, 1× for 384-well plates), and stored at −30° C. until use (max 2 months). Before inoculation, plates were thawed and pre-reduced in the anaerobic chamber overnight. The Biomek FXP (Beckman Coulter) liquid handling system was used for all rearranging and aliquoting of the library compounds.

Inoculation

Strains were grown twice overnight to make sure the inventors had a robustly and uniformly growing culture before inoculating the screening plates. For 96-well plates, the second overnight culture was diluted to fresh medium in order to reach a 2× of the aimed starting optical density (OD) at 578 nm. Next, 50 µL of this diluted inoculum was added to wells containing already 50 µl of 2× concentrated drug in the respective culture medium using a multichannel pipettor. Final drug concentration was 20 µM and each well contained 1% DMSO. For 384-well plates, the inventors inoculated with a 384 floating pin replicator VP384FP6S (V&P Scientific, Inc.), transferring 1 µl of appropriately diluted overnight culture to wells containing 50 µl of growth media, 1% DMSO and 20 µM drug. For bacterial species that reached lower OD in overnight cultures the inventors transferred twice 1 µl of appropriately adjusted OD culture. Both for 96- and 384-well plates, the starting OD was 0.01 or 0.05 depending on the growth preference of the species.

Screening conditions for the screen of the Prestwick Chemical Library

After inoculation, plates were sealed with breathable membranes (Breathe-Easy®) to prevent evaporation and cross-contamination between wells, and incubated at 37° C. without shaking. Growth curves were acquired by tracking OD at 578 nm with a microplate spectrophotometer (EON, Biotek). Measurements were taken every 1-3 hrs after 30-60 seconds of linear shaking, initially manually but later automatically using a microplate stacker (Biostack 4, Biotek), fitted inside a custom-made incubator (EMBL Mechanical Workshop). The inventors collected measurements for 16-24 hrs. Each strain was screened in at least three biological replicates.

Normalization of Growth Curves and Quantification of Growth

Growth curves were analyzed by plate. All growth curves within a plate were truncated at the time of transition from exponential to stationary. The end of exponential phase was determined automatically by finding the peak OD (using the median across all compounds and control wells, and accounting for a small increase during stationary phase) and verified by inspection. Using this timepoint allowed the inventors to capture effects of drugs on lag phase, growth rate and stationary phase plateau. Timepoints with sudden spikes in OD (e.g. caused by condensation) were removed, and a growth curve was discarded completely if there were too many missing timepoints. Similarly, growth curves were discarded if the OD fell too far outside the normal range (e.g. caused by compounds that are strongly absorbing). Three compounds had to be completely excluded from the analysis, as they mostly caused aberrant growth curves: Chicago sky blue 6B, mitoxantrone, and verteporfin. Growth curves were processed by plate to set the median OD at the start and end timepoints to 0 and 1, respectively. Then, the inventors determined reference compounds across all replicates that did not reduce growth significantly for most drugs: those were compounds for which measurements were available for >95% of replicates, and for which final OD was >0.5 for more than 122 out of 132 replicates. The inventors used these reference compounds as representatives of uninhibited growth. Since wells containing reference compounds outnumbered control wells within a plate, the inventors used control wells only later to verify the p691 value calculation. After determining reference compounds, the inventors rescaled growth curves such that the median growth of reference compounds at the end point is 1.

While growth curves in control wells and most wells with reference compounds followed the expected logistic growth pattern, a variety of deviations were observed for drugs that influenced growth. To quantify growth without relying on assumptions about the shape of the growth curve, the inventors calculated the area under the curve (AUC) using the trapezoidal rule. While the inventors set the median starting OD to 0, the OD of individual wells deviated from this. The inventors used two different methods to correct for this and determine the baseline for each growth curve. First, a constant shift was assumed, subtracting the same shift to all timepoints of the growth curve such that the minimum is zero. Second, an initial perturbation was assumed that affects initial timepoints more than later timepoints (e.g. condensation). To correct this, the inventors first subtracted a constant shift as above, and then rescaled the curve such that a timepoint with an uncorrected OD of 1 also has an OD of 1 after correction. AUCs were calculated for both scenarios, rescaled such that the AUC of reference compounds is 1, and then for each compound the baseline correction that yielded an AUC closest to 1 (i.e. normal growth) was selected. AUCs are highly correlated to final ODs, with a Pearson correlation of 0.95 across all compounds and replicates. Nonetheless, the inventors preferred to use AUCs to decrease the influence of the final timepoint, which will contain more noise than a measurement based on all timepoints.

Identification of Drugs with Anticommensal Activity

The inventors detected hits from normalized AUC measurements using a statistical method that controls for multiple hypothesis testing and varying data quality. The inventors fitted heavy-tailed distributions (scaled Student's t-distribution) to the wells containing reference compounds for each replicate and, separately, to each individual plate. These distributions captured the range of AUCs expected for compounds that did not reduce growth, and represented the null hypothesis that a given drug did not cause a growth defect in the given replicate or plate. The inventors calculated one-sided p-values from the cumulative distribution function of the fitted distribution. Within a replicate, each compound was associated with two p-values: one from the plate on which it was measured, and one for the whole replicate. Of those two, the highest p-value was chosen (conservative estimate) to control for plates with little or high noise, and varying levels of noise within the same replicate. The resulting p-values were well-calibrated (i.e. the distribution of p-values is close to uniform with the exception of a peak at low p-values) and captured the distribution of controls, which were not used for fitting the distribution and kept for validation. The inventors then combined p-values for a given drug and strain across replicates using Fisher's method. Lastly, the inventors calculated the False Discovery Rate (FDR) using the Benjamini-Hochberg method over the complete matrix of p-values (1197 compounds by 40 strains). After inspecting representative AUCs for compound—strain pairs at different FDR levels, the inventors chose a conservative FDR cut-off of 0.01.

Drug Indications, Dose, and Administration

The inventors annotated drugs by their primary target organism on the basis of their WHO Anatomical Therapeutic Chemical (ATC) classification, or, if there were uncertainties, based on manual annotation. Compounds were classified as: antibacterial drugs (antibiotics, antiseptics), anti-infective drugs (acting against protozoa, fungi, parasites or viruses), human-targeted drugs (i.e. drugs whose mechanism of action affects human cells), veterinary drugs (used exclusively in animals), and finally non-drugs (which can be drug metabolites, drugs used only in research, or endogenous substances). If a human-use drug belonged to several classes, the drug class was picked according to this order of priority (from high to low): antibacterial, anti-infective, and human-targeted drug. This ensured that drugs used also as antibacterials were not classified in other two categories.

Drugs from the Prestwick Chemical Library were matched against STITCH 4 identifiers using CART. Identifiers that could not be mapped were annotated manually. Information about drug indications, dose and administration was extracted from the ATC classification system and Defined Daily Dose (DDD) database. Dose and administration data were also extracted from the Drugs@FDA resource. Doses that were given in grams were converted to mol using the molecular weight stated in the Prestwick library information files. When the dose guidelines mentioned salt forms, the inventors manually substituted the molecular weight. Dose data from Drugs@FDA stated the amount of drug for a single dose (e.g. a single tablet). Analyzing the intersection between Drugs@FDA and DDD, the inventors found that the median ratio between the single and daily doses is two. To combine the two datasets, the inventors therefore estimated the single dose as half of the daily dose.

In general, it is difficult to estimate intestinal drug concentrations, since those depend on the dose, the speed of dissolution, uptake and metabolization by human cells and by bacteria, binding to proteins, and excretion mechanisms into the gut. To estimate gut concentrations of drugs based on their dose, the inventors relied on a known in situ study. When 40 mg (57 µmol) of posaconazole are delivered to the stomach in either an acidic or neutral solution, the maximum concentration in the duodenum reaches 26.3±10.3 and 13.6±5.8 µM, respectively. The ratio between the dose and the duodenal concentration corresponds to a volume estimate of roughly three liters.

$IC_{25}$ Determination/Screen Validation

To validate the inventors' screen, the inventors selected 25 drugs including human-targeted drugs (19), anitprotozoals (3), one antiparasitc, one antiviral and one 'no-drug' compound. The human targeted drugs spanned 5 therapeutic classes (ATC codes A, G, L, M, N). The inventors' selection comprised mostly drugs with broad-spectrum activity in the inventors' screen (19 drug hits>10 strains). This bias was for ensuring that the inventors can also evaluate false positives. The inventors chose 15 strains to test $IC_{25}$s, spanning different phyla (5) and including both sensitive (*E. rectale, R. intestinalis*) and resistant species (*E. coli* ED1a). Compounds of interest were purchased from independent sources and dissolved at 100×starting concentration in DMSO. 2-fold serial dilutions were prepared in 96-well U-bottom plates (same as screen). Each row contained a different drug at eleven 2-fold dilutions and a control DMSO well in the middle of the row (in total 8 drugs per plate). These master plates were diluted to 2× assay concentration and 2% DMSO in mGAM medium (50 µl) and stored at −30° C. (<1 month). For the assay, plates were pre-reduced overnight in the anaerobic chamber, and mixed with equal volume (50 µl) of appropriately diluted overnight culture (prepared as described for screening section) to reach a starting OD578 of 0.01 and a DMSO concentration of 1% across all wells. OD578 was measured hourly for 24 hrs after 1 min of shaking. Experiments were performed in two biological replicates.

Growth curves were converted to AUCs as described above, using in-plate control wells (no drug) to define normal growth. For each concentration, the inventors calculated the mean across the two replicates. The inventors further enforced monotonicity to conservatively remove noise effects: if the AUC decreased for lower concentrations, it was set to the highest AUC measured at higher concentrations. The IC25 was defined as the lowest concentration for which a mean AUC of below 0.75 was measured. Additionally, MIC was defined as the lowest concentration for which the AUC dropped below 0.1. In the large-scale screen, the inventors detected significant growth reductions, which do not necessarily correspond to complete growth inhibition. To ensure comparability between the results of the validation procedure and the screen, the inventors used the IC25 metric for benchmarking.

Analysis of Side Effects

Side effects (SEs) of drugs were extracted from the SIDER 4.1 database using the mapping between Prestwick compounds and STITCH 4 identifiers described above. In SIDER, SEs are encoded using the MedDRA terminology, which contains lower-level terms and preferred terms. Of these, the inventors used the preferred terms, which are more general. The inventors excluded rare SEs that occurred for less than five drugs from the analysis. Drugs with less than seven associated SEs were discarded. In a first pass, the inventors identified SEs associated with antibiotics in SIDER, by calculating for each SEs its enrichment for systemic antibiotics (ATC code J01) versus all other drugs using Fisher's exact test (p-value cut-off: 0.05, correcting for multiple hypothesis testing using the Benjamini-Hochberg method). Antibiotics are typically administered in relatively high doses, and some of the enriched SEs might therefore be caused by a dose-dependent effect (e.g. kidney toxicity). The inventors therefore used an ANOVA (Type II) to test if the presence of SEs for a drug is more strongly associated with it being an antibiotic or with its (log-transformed) dose. SEs that were more strongly associated with the dose were excluded from the list of antibiotics-related SEs.

Data on the incidence rates of SEs in patients was also extracted from SIDER 4.1. As different clinical trials can report different incidence rates, the inventors computed the median incidence rate per drug-SE pair. As SIDER also contains data on the incidence of SE upon placebo treatment, the inventors were able to ensure the absence of systematic biases.

Experimental Validation of Side Effect-Based Predictions

Selected candidate and control compounds belonged to multiple therapeutic classes (ATC codes A, B, C, G, H, L, M, N, S for candidate compounds and A, C, D, G, H, M N, R, S, V for control compounds). Compounds of interest were purchased from independent sources and if possible, dissolved at 5 mM concentration in mGAM. Lower concentrations were used when solubility limit was reached. Solutions were sterile filtered, and three 4-fold serial dilutions were arranged in 96 well plates, aiming at covering a broad range of drug concentrations. Inoculation and growth curve acquisition was performed as described for the MIC determination experiments.

Conjugation of the TransBac Overexpression Plasmid Library into *E. Coli* ΔtolC

The TransBac library, a new *E. coli* overexpression library based on a single-copy vector (H. Dose & H. Mori—unpublished resource) was conjugated in the BW25113 ΔtolC::Kan strain. The receiver strain (BW25113 ΔtolC:: kan) was grown to stationary phase in LB medium, diluted to an OD of 1, and 200 µl were spread on a LB plate supplemented with 0.3 mM diaminopimelic acid (DAP). Plates were dried for 1 hour at 37° C. and then a 1536 colony array of the library carried within a donor strain (BW38029 Hfr (CIP8 oriT::cat) dap-75) was pinned on top of the lawn. Conjugation was carried out at 37° C. for ~6 hours, and the first selection was done by pinning on LB plates supplemented with tetracycline only (10 µg/ml) and growing overnight. Two more rounds of selection followed on LB plates containing tetracycline (10 µg/ml) and kanamycin (30 µg/ml) to ensure killing of parental strains and select only for to/C mutants carrying the different plasmids.

Chemical Genomics Screen

The screen was carried out under aerobic conditions on solid LB Lennox medium (Difco), supplemented with 30

μg/ml kanamycin, 10 μg/ml tetracycline, the appropriate drug, and 0 or 100 μM IPTG. Drugs were used at the following sub-inhibitory concentrations for the tolC mutant: diacerein 20 μM, ethopropazine hydrochloride 160 μM, tamoxifen citrate 20 μM, niclosamide 1.25 μM, thioridazine hydrochloride 40 μM, methotrexate 320 μM, or for the wildtype: metformin 100 mM. The 1536 colony array of BW25113 ΔtolC::kan mutant carrying the TransBac collection was pinned on the drug-containing plates, and plates were incubated for 16-38 hours at 37° C. In the case of metformin the inventors used the version of the TransBac library, in which each plasmid complements its corresponding barcoded single-gene deletion mutant, since the inventors did not need to use the ΔtolC background for sensitizing the cell. Growth of this library was determined at 0 and 100 mM metformin (both in the presence of 0, 50 and 100 μM IPTG). All plates were imaged using an 18 megapixel Canon Rebel T3i (Canon inc USA) and images were processed using the Iris software.

Data Analysis

The inventors used colony size to measure the fitness of the mutants on the plate. For standardization of colony sizes, the inventors subtracted the median colony size and then divided by a robust estimate of the standard deviation (removing outliers below the 1st and above the 99th percentile). The inventors found edge effects affecting up to five rows and columns around the perimeter of the plate. The inventors therefore first standardized colony sizes across the whole plate using only colony sizes from the inner part of the plate as reference. To remove the edge effects, the inventors subtracted from each column its median colony size, and then from each row its median colony size. Finally, the inventors standardized the adjusted colony sizes using the whole plate as reference. The distribution of adjusted colony sizes was right-skewed (i.e. more outlier colonies with larger size), suggesting a log-normal distribution. At the same time, the presence of outliers suggested that a logarithmic equivalent of the Student's t-distribution with variable degree of freedom would be more suitable. The inventors fitted such a distribution for each plate and calculated p-values for both tails of the distribution. This approach assumes that the overexpression of most genes does not affect growth in response to drug treatment. p-values were combined using Fisher's method across replicates and IPTG concentrations (since the inventors noticed that different IPTG concentrations resulted to largely the same results—i.e. plasmids are leaky). The inventors corrected for multiple hypothesis testing for each drug individually using the Benjamini-Hochberg method. Analysis of common resistance mechanisms: To determine a relationship between the number of human-targeted drugs (h) and the number of antibacterial drugs (a) that affect each strain, the inventors determined the odds ratio (OR):

$$OR = \frac{\frac{h}{H-h}}{\frac{a}{A-a}}$$

Where H=204 and A=122 are the numbers of human-targeted and antibacterial drugs that show activity, respectively. The inventors computed the nonlinear least-squares estimate for OR based on the following equation:

$$\frac{h}{H-h} = OR \cdot \frac{a}{A-a}$$

Results

A High-Throughput Drug Screen on Human Gut Bacterial Species

To systematically map interactions between drugs and human gut microbes, the inventors monitored the growth of 40 representative isolates upon treatment with 1197 compounds in modified Gifu Anaerobic Medium broth (mGAM), which partially recapitulates species abundances in the gut, under anaerobic atmosphere, at 37° C. The inventors used the Prestwick Chemical Library, consisting mostly of off-patent FDA-approved compounds and spanning a wide range of chemical and pharmacological diversity. Most compounds are administered to humans (1079), covering all main therapeutic classes. Three quarters (835) are human-targeted drugs (i.e. have molecular targets in human cells), whereas the rest are anti-infectives: 156 with antibacterial activity (144 antibiotics and 12 antiseptics) and 88 mainly effective against fungi, viruses, and protozoan or metazoan parasites (FIG. 1a). All compounds were screened at a concentration of 20 μM, which is within the range of what is commonly used in high-throughput drug screens and on average, slightly below doses administered to patients (FIG. 2a).

To be representative of the gut microbiome of healthy individuals, the inventors profiled a diverse set of ubiquitous gut bacterial species. Prevalence and abundance in the human gut, and phylogenetic diversity were the inventors' main selection criteria. In a few cases the selection was constrained due to strain unavailability or irreproducible growth in mGAM. In total, the inventors included 40 human gut isolates from 38 bacterial species and 21 genera (with *E. coli* and *B. fragilis* being represented by two different strains), accounting together for 78% of the assignable median relative abundance of the human gut microbiome at genus level (60% at species level). Most of these strains are commensals, and represent 31 out of the 60 species with available reference genome sequences detected at a relative abundance of ≥1% and prevalence of ≥50% in a large collection of fecal samples of asymptomatic humans from three continents. In addition, the set includes a few pathobionts (*Clostridium difficile, Clostridium perfringens, Fusobacterium nucleatum* and an enterotoxigenic strain of *Bacteroides fragilis*), a probiotic (*Lactobacillus paracasei*) and two further commensal *Clostridia* (*C. ramosum* and *C. saccharolyticum*), all human isolates. All bacteria probed were part of a larger resource representing the core of the healthy human gut microbiome.

The experimental setup included screening all compounds, arrayed in 96- or 384-well plates, in at least three biological replicates for each strain. The inventors measured optical density over time as growth readout, quantifying the area under the growth curve (AUC) up to the transition to stationary phase (estimated on controls with unperturbed growth). Correlation between replicates was very good (median 0.89). The inventors then tested for significant deviations from the normalized AUC distribution of samples with unperturbed growth, combining p-values across replicates and correcting for multiple hypothesis testing on the complete matrix of compounds and strains. If a drug significantly reduced growth of at least one tested strain (FDR<0.01), and thus has potential to modulate the human gut microbiota, the inventors classified it as a hit with anticommensal activity.

Of the 156 antibacterials present in the inventors' screen, 78% were active against at least one gut commensal species, typically with broad activity spectrum (FIGS. 1a-b). Inactive antibiotics mainly belong to the classes of sulfonamides (active at higher concentrations), aminoglycosides (mostly inactive in anaerobes and/or under anaerobic conditions due to limited drug uptake) and rather specific antimycobacterial drugs. Thus, although antibiotics are used to inhibit pathogens, they also target gut commensals. This is presumably due to their broad spectrum activity. Although the medical importance of this collateral damage of antibiotics to the resident microbiome is becoming increasingly clear, their specific activities against diverse microbiome species had not been mapped at this scale before.

Interestingly, 27% of the non-antibiotic drugs (i.e. other anti-infectives and human targeted drugs) were also active in the inventors' screen. More than half of the anti-infectives against viruses or eukaryotes exhibited anticommensal activity (47 drugs ~53%; FIGS. 1a-b). Antibacterial activity has been previously reported for many of them, including the antifungal imidazoles (10 in the inventors' screen), but for particular others (for example the antivirals efavirenz and trifluridine) such activity is new. More noteworthy and novel is the anticommensal activity observed for human-targeted drugs (24%). In contrast to anti-infectives, most human-targeted drugs were effective against a small subset of strains with a number of notable exceptions: 36 drugs affected >10 strains, with 11 having no previously reported antibacterial activity. From the known ones, auranofin was recently reported to have broad-spectrum bactericidal activity and even target multi-drug resistant isolates. Another compound, the ovulation stimulant clomiphene, targets a widespread and conserved bacterial enzyme in undecaprenyl phosphate synthesis, which is an essential precursor for cell wall carbohydrate polymers. The scaffolds of such non-antibiotic drugs with antimicrobial activity can be used as starting points for repurposing towards broad spectrum antibiotics. On the other hand, the microbial specificity of most human-targeted drugs suggests that their scaffolds could be used in the future for developing narrow-spectrum antibacterials and/or modulators of the microbiome composition.

When considering the total number of drugs inhibiting each bacterial isolate, it is apparent that some species are influenced more than others, with the abundant *Roseburia intestinalis*, *Eubacterium rectale* and *Bacteroides vulgatus*, being the most susceptible, and γ-proteobacteria representatives being the most resistant (FIG. 1a). Overall, species with higher relative abundance across healthy individuals were significantly more susceptible to human-targeted drugs in the inventors' screen (FIG. 1c). This suggests that human-targeted drugs have an even larger overall impact to the gut microbiome with key species related to its healthy status, such as major butyrate—(*E. rectale*, *R. intestinalis*, *Coprococcus comes*) and propionate-producers (*B. vulgatus*, *Prevotella copri*, *Blautia obeum*), and enterotype drivers being impacted the most.

Many More Human-Targeted Drugs are Likely to Inhibit Gut Bacteria

The notion that the impact of human-targeted drugs on the gut microbiome may be even broader than the inventors' screen revealed is supported by several lines of evidence. First, the drug concentration used in this screen (20 μM), is below the median estimated gut concentration of the drugs that the inventors tested (FIG. 2a). Since the effective concentration of a drug in the gut is rarely measured, the inventors relied on available data on recommended administration doses for 653 human-targeted drugs, and used detailed measurements of intestinal concentrations for the case of posaconazole to covert administration doses to estimates of gut concentrations for the other drugs. Interestingly, the human targeted drugs with anticommensal activity in the inventors' screen have lower estimated intestinal concentrations than ones without (FIG. 2a; p=0.001, Wilcoxon rank sum test), suggesting that more human-targeted drugs would inhibit bacterial growth if probed at higher doses, closer to recommended administration levels. A case in point is the antidiabetic drug metformin, which was recently identified as the key contributor to changes in the human gut microbiome composition of type-II diabetes (T2D) patients, but did not show anticommensal activity in the inventors' screen. Metformin reaches up to ~10 mM plasma concentration in treated T2D patients, and its small intestine concentration is calculated to be 30-300 fold higher, which are both much higher than the screen concentration (20 μM). Similarly, the inventors' estimated gut concentration for metformin is at 5 mM (FIG. 2a). When the inventors probed for higher concentrations of metformin, 5/22 strains had a Minimal Inhibitory Concentration (MIC) <10 mM, and further strains had a MIC an order of magnitude higher, which is still within physiological levels of metformin in the gut.

Second, benchmarking the inventors' screen with an independent set of targeted validation experiments (MIC testing for 22 selected drugs in a subset of 15 strains; see Methods), revealed excellent precision (96%), but slightly lower recall (85%) due to more false negatives (FNs), i.e. drugs with anticommensal that the inventors missed in the inventors' screen (FIG. 2b). Many FNs were due to screen biases, as they mostly came from a few sensitive chemicals that probably lost activity during the screening process (for example, see loperamide or acarbose) and the inventors' stringent FDR cutoff for calling hits. Indeed, increasing the FDR threshold to 0.1 would almost double the fraction of drugs impacting human gut commensals. Along these lines, the validation experiments revealed that more species were inhibited at higher concentrations, confirming the idea more human-targeted drugs would have had anticommensal activity, if the inventors had screened higher concentrations within the recommended administration doses.

Third, the human gut microbiome harbors hundreds of species and an even larger diversity of strains, whereas the inventors only screened a small representative subset. Rarefaction analysis indicates that if more gut species were tested, the fraction of human-targeted drugs with impact on commensals would increase (FIG. 2c). In contrast, the number of antibacterial drug hits saturates early within the strains tested, indicating that screening more species would not substantially increase the fraction of antibiotic hits in the screen. Taken together, these results suggest that a considerably higher proportion of human targeted drugs than the 24% the inventors' screen reports is likely to inhibit the growth of human gut microbes.

Side Effects of Human-Targeted Drugs Validate their Systemic Impact

Although the inventors demonstrated that human-targeted drugs commonly inhibit gut microbes in vitro, evidence that such effects also manifest in vivo in the human gut currently exists only for a handful of cases. To bridge this gap and address the physiological relevance of the inventors' screen, the inventors looked into the registered effects that these drugs have in humans. The rationale of the inventors was that if human-targeted drugs target the gut microbiome, some of the consequences should be apparent from their side effects, which should exhibit some similarity to those of antibiotics.

The inventors first identified side effects enriched in antibiotics for systemic use compared to those found in all other drugs in the SIDER database version 4.1 25. The inventors identified 69 side effects that were enriched in antibiotics, excluding side effects that are likely caused by high-dose-related host toxicity. The inventors then tested whether antibiotic related side effects occurred with higher frequency in clinical trials for human-targeted drugs with anticommensal activity compared to inactive compounds in the inventors' screen, which turned out to be true (p=0.002, Wilcoxon rank sum test, FIG. 3a). No significant difference was observed for patients receiving a placebo, suggesting the absence of biases (FIG. 3a).

The analysis above suggests that the collateral damage of human-targeted drugs on gut microbes can be detected by the higher occurrence of antibiotic-like side effects in patients. The inventors thus wondered whether this side effect signature could be used to predict anticommensal activity of other human-targeted drugs, which the inventors may have missed due to the low drug concentration used in the inventors' screen (FIG. 2a). To test this hypothesis, the inventors screened 26 candidate compounds with high enrichment of antibiotic-related side effects and 16 without (control compounds) in 18 strains (FIG. 3b), in concentrations up to 2500 μM. Of the 42 compounds in total, 28 inhibited the growth of at least one strain (FIG. 3b). For both candidate and control compounds, the fraction of growth-inhibiting compounds was close to two thirds, and there was no significant difference in the number of affected strains. However, when the inventors normalized the measured MICs by the recommended drug doses to make amounts comparable between drugs, a significant difference was evident. Drugs predicted to be active had a median MIC across all drug-strain pairs that corresponded to 4.3 drug doses, compared to 12 for control drugs (p=2e-6, one-sided Wilcoxon rank sum test; FIG. 3c). For drugs predicted to have anticommensal activity, 34% of the MICs correspond to less than two drug doses, compared with just 8% for control drugs. Interestingly, all seven NSAIDs among the inventors' predictions showed anticommensal activity at higher concentrations, affecting 6 to 18 strains, and 44% of these MICs corresponded to less than two drug doses. This is consistent with recent metagenomics studies associating NSAID use with microbiome changes.

In summary, side effect patterns in humans can differentiate human-targeted drugs with anticommensal activity from those without, confirming the physiological relevance of the inventors' in vitro screen. The inventors thus explored next the chemical and biological properties of the interacting drugs and bacteria, respectively.

Therapeutic Indication Areas and Chemical Properties of Human-Targeted Drugs with Anticommensal Activity Drugs from all major indication areas according to the Anatomical Therapeutic Chemical classification (ATC) inhibited growth of at least one gut microbe, with drugs applied topically (classes S and D) exhibiting the lowest hit rate (FIG. 4a). At the other side of the spectrum, antineoplastics, hormones and compounds targeting our nervous system inhibited gut microbes more than other medications (FIG. 4a). Within the ATC classification, three subclasses were significantly enriched in hits: antimetabolites, antipsychotics and calcium channel blockers (FIG. 4a). Antimetabolites are used as chemotherapeutic and immunosuppressant agents with their incorporation into RNA/DNA or their interaction with RNA/DNA synthesis enzymes having cytotoxic effects to human cells. Their molecular targets and cytotoxicity are often conserved in bacteria, explaining the observed effects. In addition, the inventors' results imply that antimetabolites could play a more direct role in mucositis development during chemotherapy.

The enrichment in antipsychotics is less straightforward, given that these target dopamine and serotonin receptors in the brain, which are absent in bacteria. Although phenothiazines are known to have antibacterial effects, the inventors observed anticommensal activity for nearly all subclasses of the chemically diverse antipsychotics in the inventors' screen, and the pattern of species inhibited was similar even for chemically distinct sub-classes (FIG. 4b). In general, antipsychotics targeted more similar sets of species than expected, based on their chemical similarity (FIG. 4c). This raises the possibility that direct bacterial inhibition may not only manifest as side effects for antipsychotics but also be part of their MoA.

Many therapeutic sub-classes do not have enough representatives in the inventors' screen to yield a statistically significant enrichment for anticommensal activity. Among them, all three PPIs that are part of the Prestwick Chemical Library exhibited broad anticommensal activity. When comparing the inhibited species in the inventors' study to the microbiome changes in patients using PPIs, the inventors found high concordance. Taxa with reduced abundance in patients included drug—strain pairs in this screen with reduced growth, while enriched taxa were rarely inhibited by PPIs in the inventors' study. This suggests that PPI could also influence directly the gut microbiome composition, in addition to changing the stomach pH and thereby the microbes that can reach our gut.

As indication areas often contain chemically similar drugs, the inventors explored whether certain chemical properties of drugs can influence their anticommensal activity. To some degree, human-targeted drugs with higher chemical similarity had more similar effects in the screen. The inventors also tested a number of compound properties including complexity, molecular weight, topological polar surface area (TPSA), volume, and XLogP as a measure of hydrophobicity. Complex, heavier and larger compounds preferentially target Gram-positive bacteria, whereas Gram-negative bacteria are protected against such bulkier drugs. This is in accordance with the selective outer membrane barrier of Gram-negative bacteria, which confers protection against bulky and/or hydrophobic drugs. Due to the very large number of chemical moieties present in drugs with anticommensal activity, the inventors did not attempt an exhaustive enrichment analysis. Nevertheless, the inventors did observe reactive nitro-groups to be significantly enriched in drugs with anticommensal activity (p=6.4 e-06), indicating that local chemical properties may confer antibacterial activity. Thus, despite the wide range of indication areas and chemical diversity of anticommensals, some chemical properties of human-targeted drugs associate with their antibacterial spectrum.

Human-Targeted Drug Consumption May Promote Antibiotic Resistance

The inventors next investigated whether resistance mechanisms influenced the spectrum of effects observed for gut microbes. Intriguingly, the inventors noticed a strong correlation between resistance to antibacterials and human-targeted drugs (FIG. 5a). This suggested that susceptibility towards xenobiotics in general is determined by intrinsic properties of the individual bacterial strains. These properties go beyond general cell envelope composition, as there is no clear division between Gram-positive and Gram-negative bacteria in the inventors' data (FIG. 5a). The inventors reasoned that more specific, yet common mechanisms could confer resistance against both antibiotics and human-targeted drugs. To test this hypothesis for one of the most common resistance mechanisms against antibiotics, that of efflux pumps, the inventors selected a prominent member, TolC, known to confer resistance to several antibiotics in *E. coli* and many other bacteria. The inventors profiled an *E. coli* ΔtolC mutant strain and its parental wildtype (BW25113) against all the compounds of the Prestwick Chemical Library. *E. coli* lacking TolC did not only become more sensitive to antibacterials (22 hits more than wildtype), but also became equally more sensitive to human-targeted drugs (19 additional hits; FIG. 5a). This confirms the existence of cross-resistance mechanisms between antibiotic and non antibiotic drugs.

To more systematically elucidate mechanisms conferring resistance against human-targeted drugs, the inventors employed a chemical genomics approach and screened a genome-wide overexpression library in *E. coli* against seven non-antibiotic drugs (six human-targeted drugs and niclosamide, an antiparasitic) with broad impact on gut microbes in the inventors' screen. Since wildtype *E. coli* was one of the most resistant species in the inventors' screen (FIG. 5a), the inventors decided to use the to/C mutant that is sensitive to many of these drugs, allowing the inventors to probe further resistance mechanisms. For all tested drugs except metformin, overexpression of to/C rescued *E. coli* growth, as expected. Furthermore, the inventors identified a number of diverse transporter families contributing to specific resistance against these drugs (FIG. 5b). Many of them have been linked to antibiotic resistance in the past. Resistance was also acquired by overexpression of transcription factors (e.g. rob, which is known to control efflux pump expression), the ribosome maturation factor rrmA, which plays a role in resistance to the antibiotic viomycin, and detoxification mechanisms (nitroreductases are known to modify nitro-containing antibiotics). Interestingly, for the case of methotrexate, the inventors' chemical genomics screen identified the already known primary target in bacteria (*E. coli* dihydrofolate reductase), illustrating the potential of this approach to identify bacterial MoA of human targeted drugs. All these results support the concept of an overlap between resistance mechanisms against antibiotics and human-targeted drugs. This implies a hitherto unnoticed risk of acquiring antibiotic resistance by consumption of non-antibiotic drugs.

Table 1 shows isolated strains of the human microbiota used in this study.

| Database (NT) | Phylum | Class | Order | Family | Genus |
|---|---|---|---|---|---|
| 5001 | Bacteroidetes | Bacteroidia | Bacteroidales | Bacteroidaceae | *Bacteroides* |
| 5002 | Bacteroidetes | Bacteroidia | Bacteroidales | Bacteroidaceae | *Bacteroides* |
| 5003 | Bacteroidetes | Bacteroidia | Bacteroidales | Bacteroidaceae | *Bacteroides* |
| 5004 | Bacteroidetes | Bacteroidia | Bacteroidales | Bacteroidaceae | *Bacteroides* |
| 5006 | Firmicutes | Clostridia | Clostridiales | Clostridiaceae | *Clostridium* |
| 5009 | Firmicutes | Clostridia | Clostridiales | Eubacteriaceae | *Eubacterium* |
| 5011 | Firmicutes | Clostridia | Clostridiales | Lachnospiraceae | *Roseburia* |
| 5017 | Firmicutes | Negativicutes | Selenomondales | Veillonellaceae | *Veillonella* |
| 5019 | Bacteroidetes | Bacteroidia | Bacteroidales | Prevotellaceae | *Prevotella* |
| 5021 | Verrucomicrobia | Verrucomicrobiae | Verrucomicrobiales | Verrucomicrobiaea | *Akkermansia* |
| 5022 | Actinobacteria | Actinobacteria | Bifidobacteriales | Bifidobacteriaceae | *Bifidobacterium* |
| 5024 | Actinobacteria | Actinobacteria | Coriobacteriales | Coriobacteriaceae | *Eggerthella* |
| 5025 | Fusobacteria | Fusobacteria | Fusobacteriales | Fusobacteriaceae | *Fusobacterium* |
| 5026 | Firmicutes | Clostridia | Clostridiales | Clostridiaceae | *Clostridium* |
| 5028 | Actinobacteria | Actinobacteria | Bifidobacteriales | Bifidobacteriaceae | *Bifidobacterium* |
| 5032 | Firmicutes | Clostridia | Clostridiales | Clostridiaceae | *Clostridium* |
| 5033 | Bacteroidetes | Bacteroidia | Bacteroidales | Bacteroidaceae | *Bacteroides* |
| 5036 | Proteobacteria | Deltaproteobacteria | Desulfovibrionales | Desulfovibrionaceae | *Bilophila* |
| 5037 | Firmicutes | Clostridia | Clostridiales | Clostridiaceae | *Clostridium* |
| 5038 | Firmicutes | Bacilli | Lactobacillales | Streptococcaceae | *Streptococcus* |
| 5042 | Firmicutes | Bacilli | Lactobacillales | Lactobacillaceae | *Lactobacillus* |
| 5045 | Firmicutes | Clostridia | Clostridiales | Ruminococcaceae | *Ruminococcus* |
| 5046 | Firmicutes | Clostridia | Clostridiales | Lachnospiraceae | *Blautia* |
| 5047 | Firmicutes | Clostridia | Clostridiales | Lachnospiraceae | *Blautia* |
| 5048 | Firmicutes | Clostridia | Clostridiales | Lachnospiraceae | *Coprococcus* |
| 5050 | Bacteroidetes | Bacteroidia | Bacteroidales | Bacteroidaceae | *Bacteroides* |
| 5054 | Bacteroidetes | Bacteroidia | Bacteroidales | Bacteroidaceae | *Bacteroides* |
| 5064 | Bacteroidetes | Bacteroidia | Bacteroidales | Bacteroidaceae | *Bacteroides* |
| 5069 | Firmicutes | Clostridia | Clostridiales | Lachnospiraceae | *Blautia* |
| 5071 | Bacteroidetes | Bacteroidia | Bacteroidales | Porphyromonadaceae | *Parabacteroides* |
| 5072 | Firmicutes | Bacilli | Lactobacillales | Streptococcaceae | *Streptococcus* |
| 5073 | Actinobacteria | Actinobacteria | Coriobacteriales | Coriobacteriaceae | *Collinsella* |
| 5074 | Bacteroidetes | Bacteroidia | Bacteroidales | Porphyromonadaceae | *Parabacteroides* |
| 5075 | Firmicutes | Clostridia | Clostridiales | Eubacteriaceae | *Eubacterium* |
| 5076 | Firmicutes | Clostridia | Clostridiales | Lachnospiraceae | *Dorea* |
| 5077 | Proteobacteria | Gammaproteobacteria | Enterobacteriales | Enterobacteriaceae | *Escherichia* |

-continued

| | | | | | |
|---|---|---|---|---|---|
| 5078 | Proteobacteria | Gammaproteobacteria | Enterobacteriales | Enterobacteriaceae | *Escherichia* |
| 5079 | Firmicutes | Clostridia | Clostridiales | Lachnospiraceae | *Roseburia* |
| 5081 | Bacteroidetes | Bacteroidia | Bacteroidales | Porphyromonadaceae | *Odoribacter* |
| 5083 | Firmicutes | Clostridia | Clostridiales | Clostridiaceae | *Peptoclostridium* |

| Database (NT) | Species | Strain | Source | Medium preference |
|---|---|---|---|---|
| 5001 | *Bacteroides vulgatus* | type strain | DSM 1447 | mGAM |
| 5002 | *Bacteroides uniformis* | VPI 0061 | DSM 6597 | mGAM |
| 5003 | *Bacteroides fragilis nontoxigenic* | EN-2, VPI 2553 | DSM 2151 | mGAM |
| 5004 | *Bacteroides thetaiotaomicron* | E50(VPI 5482) | DSM 2079 | mGAM |
| 5006 | *Clostridium ramosum* | type strain, 113-I, VPI 0427 | DSM 1402 | mGAM |
| 5009 | *Eubacterium rectale* | A1-86 | DSM 17629 | mGAM |
| 5011 | *Roseburia intestinalis* | L1-82 | DSM 14610 | mGAM |
| 5017 | *Veillonella parvula* | type strain, Te3 | DSM 2008 | Todd-Hewitt + 0.6 % sodium lactate |
| 5019 | *Prevotella copri* | type strain, CB7 | DSM 18205 | mGAM |
| 5021 | *Akkermansia muciniphila* | type strain, Muc | DSM 22959 | mGAM |
| 5022 | *Bifidobacterium adolescentis* | type strainE194 a (Variant a) | DSM 20083 | mGAM |
| 5024 | *Eggerthella lenta* | type strain, 1899 B, VPI 0255 | DSM 2243 | mGAM |
| 5025 | *Fusobacterium nucleatum* subsp. *Nucleatum* | type strain, 1612A, VPI 4355 | DSM 15643 | mGAM |
| 5026 | *Clostridium bolteae* | type strain, WAL 16351 | DSM 15670 | mGAM |
| 5028 | *Bifidobacterium longum* subsp. *Longum* | type strain, E194b (Variant a) | DSM 20219 | mGAM |
| 5032 | *Clostridium perfringens* | C36 | DSM 11782 | mGAM |
| 5033 | *Bacteroides fragilis enterotoxigenic (ET)* | 20656-2-1 | ATCC 43860 | mGAM |
| 5036 | *Bilophila wadsworthia* | type strain, WAL 7959 [Lab 88-130H] | ATCC 49260 | mGAM supplemented with 60 mM sodium formiate and 10 mM taurine |
| 5037 | *Clostridium saccharolyticum* | type strain, WM1 | DSM 2544 | mGAM |
| 5038 | *Streptococcus salivarius* | type strain, 275 | DSM 20560 | mGAM |
| 5042 | *Lactobacillus paracasei* | LPC-37, ATCC SD5275 | Dupont Health and Nutrition | mGAM |
| 5045 | *Ruminococcus bromii* | type strain, VPI 6883 | ATCC 27255 | mGAM |
| 5046 | *Ruminococcus gnavus* | type strain, VPI C7-9 | ATCC 29149 | mGAM |
| 5047 | *Ruminococcus torques* | type strain, VPI B2-51 | ATCC 27756 | mGAM |
| 5048 | *Coprococcus comes* | type strain, VPI CI-38 | ATCC 27758 | mGAM |
| 5050 | *Bacteroides caccae* | Type strain, CCUG 38735, CIP 104201, JCM 9498, NCTC 13051, VPI 3452A | DSM 19024/ ATCC 43185 | mGAM |

-continued

| | | | | |
|---|---|---|---|---|
| 5054 | *Bacteroides ovatus* | NCTC 11153, Type strain | ATCC 8483 | mGAM |
| 5064 | *Bacteroides xylan-isolvens* | Strain CL03T12C04, HM-722 | BEI Resources | mGAM |
| 5069 | *Blautia obeum* | type strain | DSM 26238 | mGAM |
| 5071 | *Parabacteroides merdae* | VPI T4-1 [CIP 104202T, JCM 9497] | DSM 19495 | mGAM |
| 5072 | *Streptococcus parasanguinis* | type strain | DSM 6778 | mGAM |
| 5073 | *Collinsella aerofaciens* | ATCC 25986, type strain VPI 1003 | DSM 3979 | mGAM |
| 5074 | *Parabacteroides distasonis* | ATCC 8503, CCUG 4941, JCM 5825, NCTC 11152 | DSM 20701 | mGAM |
| 5075 | *Eubacterium eligens* | C15-B4, type strain | DSM 3376 | mGAM |
| 5076 | *Dorea formicigenerans* | VPI C8-13 | DSM 3992 | mGAM |
| 5077 | *Escherichia coli* IAI1 | IAI1 | Denamur Lab (INSERM) | mGAM |
| 5078 | *Escherichia coli* ED1a | ED1a | Denamur Lab (INSERM) | mGAM |
| 5079 | *Roseburia hominis* | A2-183, type strain | DSM 16839 | GMM + mGAM |
| 5081 | *Odoribacter splanchnicus* | 1651/6, type strain | DSM 20712 | mGAM |
| 5083 | *Clostridium difficile* | 630 | DSM 27543 | mGAM |

Table 2 shows additional *bacteroides* used in this study

| | | | | | | | | | | |
|---|---|---|---|---|---|---|---|---|---|---|
| 5057 | Bacteroidetes | Bacteroidia | Bacteroidales | Bacteroidaceae | *Bacteroides* | *Bacteroides fragilis* | HM-20, Strain 3_1_12 | BEI Resources | mGAM |
| 5065 | Bacteroidetes | Bacteroidia | Bacteroidales | Bacteroidaceae | *Bacteroides* | *Bacteroides uniformis* | HM-715, Strain CL03T00C23 | BEI Resources | mGAM |

Table 3 shows laboratory *E. coli* strains used in this study

| data base | Phylum | Class | Source | Medium preference |
|---|---|---|---|---|
| NT5084 | BW25113 | BW25113 WT | PMID: 10829079 | mGAM |
| NT5085 | BW25113 | BW25113 ΔtolC::kan | from Keio collection JW5503-1 (PMID: 16738554) | mGAM |

Table 4 shows narrow-spectrum compounds effective against *C. difficile*. Shown are the adjusted p-values of the compound-induced inhibition on the growth of 40 different bacterial species as indicated. Note: A compound is defined as "narrow-spectrum" if it inhibits the growth of less than 9 species of 40 different bacterial species tested.

| prestwick_ID | Telmisartan | Azathioprine | Mercaptopurine | Mifepristone | Montelukast | Cilnidipine | Fentiazac | Lacidipine | Meclozine dihydrochloride | Carbenoxolone disodium salt | Tribenoside | Gliquidone | Fendiline hydrochloride | Amlodipine |
|---|---|---|---|---|---|---|---|---|---|---|---|---|---|---|
| n_hit | 1350 4 | 94 7 | 1469 4 | 299 3 | 1189 8 | 1376 5 | 1254 1 | 1297 6 | 457 8 | 837 2 | 1019 1 | 991 1 | 270 8 | 1219 2 |
| *Akkermansia muciniphila* (NT5021) | 1.000 | 0.413 | 0.222 | 1.000 | 1.000 | 1.000 | 1.000 | 1.000 | 0.733 | 0.852 | 1.000 | 1.000 | 1.000 | 1.000 |
| *Bacteroides caccae* (NT5050) | 0.868 | 0.175 | 1.000 | 0.024 | 1.000 | 0.926 | 1.000 | 1.000 | 0.029 | 0.429 | 0.058 | 0.886 | 0.994 | 1.000 |
| *Bacteroides fragilis* (ET) (NT5033) | 0.018 | 1.000 | 1.000 | 0.022 | 0.340 | 0.010 | 0.684 | 0.154 | 0.086 | 0.936 | 0.068 | 0.815 | 0.490 | 0.780 |
| *Bacteroides fragilis* (NT) (NT5003) | 0.242 | 0.917 | 0.907 | 0.010 | 0.253 | 0.340 | 0.619 | 1.000 | 0.059 | 1.000 | 0.254 | 1.000 | 0.016 | 0.783 |
| *Bacteroides ovatus* (NT5054) | 1.000 | 0.220 | 1.000 | 0.114 | 1.000 | 1.000 | 1.000 | 0.835 | 0.021 | 0.344 | 0.044 | 1.000 | 0.952 | 0.838 |
| *Bacteroides thetaiotaomicron* (NT5004) | 0.224 | 0.517 | 0.450 | 0.079 | 0.961 | 0.859 | 1.000 | 0.579 | 0.015 | 0.943 | 0.801 | 0.773 | 0.293 | 1.000 |
| *Bacteroides uniformis* (NT5002) | 0.316 | 0.510 | 1.000 | 0.003 | 0.937 | 0.507 | 0.336 | 1.000 | 0.016 | 0.999 | 0.833 | 1.000 | <0.001 | 0.637 |
| *Bacteroides vulgatus* (NT5001) | 0.118 | 0.927 | 1.000 | 0.021 | 0.799 | 0.880 | 1.000 | 0.774 | 0.001 | 1.000 | 0.230 | 1.000 | <0.001 | 0.579 |
| *Bacteroides xylanisolvens* (NT5064) | 0.783 | 0.105 | 1.000 | 0.131 | 1.000 | 1.000 | 1.000 | 0.782 | 1.000 | 0.356 | 0.188 | 1.000 | 1.000 | 1.000 |
| *Bifidobacterium adolescentis* (NT5022) | 1.000 | 0.714 | 0.851 | 0.724 | 1.000 | NA | 1.000 | 0.002 | 0.037 | 0.132 | 0.733 | 0.913 | 1.000 | 1.000 |
| *Bifidobacterium longum* (NT5028) | 1.000 | 0.141 | 0.605 | 0.853 | 1.000 | 0.938 | 1.000 | 0.015 | 0.092 | 0.150 | 0.601 | 1.000 | 0.689 | 0.895 |
| *Bilophila wadsworthia* (NT5036) | 0.519 | 1.000 | 1.000 | 1.000 | 0.055 | 0.730 | 0.878 | 0.632 | 1.000 | 0.861 | 0.944 | 1.000 | 0.626 | 0.853 |
| *Blautia obeum* (NT5069) | 0.358 | <0.001 | 0.014 | 1.000 | 0.091 | 0.018 | 1.000 | 0.070 | <0.001 | 0.030 | 0.315 | 1.000 | 0.337 | 1.000 |
| *Clostridium bolteae* (NT5026) | 0.907 | 0.024 | 1.000 | 0.886 | 0.139 | NA | 1.000 | 0.839 | 0.016 | 0.580 | 0.415 | 1.000 | 0.521 | 0.828 |
| *Clostridium difficile* (NT5083) | <0.001 | <0.001 | <0.001 | <0.001 | 0.001 | 0.001 | 0.001 | 0.001 | 0.001 | 0.003 | 0.005 | 0.006 | 0.006 | 0.009 |
| *Clostridium perfringens* (NT5032) | 0.007 | 0.884 | 1.000 | 0.358 | <0.001 | 0.152 | 1.000 | 0.004 | 0.026 | <0.001 | 0.283 | 0.809 | 0.350 | 1.000 |

-continued

| | Telmisartan | Azathioprine | Mercaptopurine | Mifepristone | Montelukast | Clinidipine | Fentiazac | Lacidipine | Meclozine dihydrochloride | Carbenoxolone disodium salt | Tribenoside | Gliquidone | Fendiline hydrochloride | Amlodipine |
|---|---|---|---|---|---|---|---|---|---|---|---|---|---|---|
| *Clostridium ramosum* (NT5006) | 0.262 | 0.943 | 0.591 | 0.581 | 1.000 | 0.860 | 1.000 | 0.431 | 0.031 | 0.035 | 0.565 | 0.678 | 0.741 | 1.000 |
| *Clostridium saccharolyticum* (NT5037) | 0.693 | 0.094 | 0.148 | 0.561 | 1.000 | 0.892 | 1.000 | 1.000 | 0.037 | 0.712 | 0.147 | 0.394 | 0.435 | 1.000 |
| *Collinsella aerofaciens* (NT5073) | 1.000 | 0.003 | 0.002 | 0.820 | 1.000 | 1.000 | 1.000 | 0.819 | <0.001 | 0.087 | 0.203 | 1.000 | 0.230 | 1.000 |
| *Coprococcus comes* (NT5048) | 0.027 | 0.001 | <0.001 | 0.882 | <0.001 | NA | 1.000 | 0.009 | 0.050 | 0.471 | 0.411 | 1.000 | 0.004 | 0.145 |
| *Dorea formicigenerans* (NT5076) | 1.000 | 0.629 | 0.688 | 0.907 | 0.350 | 0.779 | 1.000 | 1.000 | 0.018 | 0.222 | 0.098 | 1.000 | 0.211 | 0.996 |
| *Eggerthella lenta* (NT5024) | 0.503 | 0.008 | 0.027 | 1.000 | 1.000 | 0.565 | 0.992 | 1.000 | 0.768 | 0.249 | 0.815 | 1.000 | 1.000 | 1.000 |
| *Escherichia coli* ED1a (NT5078) | 0.452 | 1.000 | 1.000 | 0.410 | 1.000 | 0.809 | 0.895 | 0.781 | 0.392 | 0.862 | 0.750 | 1.000 | 0.228 | 0.806 |
| *Escherichia coli* IAI1 (NT5077) | 0.400 | 1.000 | 1.000 | 0.459 | 1.000 | 0.463 | 1.000 | 1.000 | 0.046 | 0.712 | 0.767 | 1.000 | 0.784 | 0.636 |
| *Eubacterium eligens* (NT5075) | 1.000 | 0.888 | 1.000 | 1.000 | 0.845 | 0.137 | 1.000 | 1.000 | 0.001 | 0.694 | 1.000 | 1.000 | 0.009 | 0.011 |
| *Eubacterium rectale* (NT5009) | 0.131 | 0.025 | 0.092 | 0.165 | 0.007 | NA | 1.000 | 0.093 | 0.009 | 0.923 | 0.046 | 1.000 | 0.005 | 0.188 |
| *Fusobacterium nucleatum* (NT5025) | 0.589 | 0.153 | 0.189 | 0.167 | 1.000 | 1.000 | 0.638 | 1.000 | 0.569 | 1.000 | 0.013 | 1.000 | 1.000 | 1.000 |
| *Lactobacillus paracasei* (NT5042) | 1.000 | 0.951 | 1.000 | 0.182 | 0.783 | 0.945 | 0.979 | 0.653 | 0.158 | 0.953 | 1.000 | 1.000 | 0.309 | 1.000 |
| *Odoribacter splanchnicus* (NT5081) | 1.000 | 0.369 | 0.607 | 0.970 | 1.000 | 1.000 | 1.000 | 1.000 | 0.110 | 0.391 | 0.564 | 1.000 | 0.831 | 0.985 |
| *Parabacteroides distasonis* (NT5074) | 0.004 | 1.000 | 1.000 | 0.019 | <0.001 | 0.003 | 0.667 | 0.560 | 0.161 | 0.943 | 0.109 | 0.018 | 0.534 | 0.833 |
| *Parabacteroides merdae* (NT5071) | 0.116 | 0.462 | 0.925 | <0.001 | 0.054 | 0.010 | 0.205 | 1.000 | 0.068 | 1.000 | 0.032 | 0.990 | 0.032 | 1.000 |

-continued

| | Telmisartan | Azathioprine | Mercaptopurine | Mifepristone | Montelukast | Cilnidipine | Fentiazac | Lacidipine | Meclozine dihydrochloride | Carbenoxolone disodium salt | Tribenoside | Gliquidone | Fendiline hydrochloride | Amlodipine |
|---|---|---|---|---|---|---|---|---|---|---|---|---|---|---|
| *Prevotella copri* (NT5019) | 0.245 | <0.001 | <0.001 | 0.309 | 0.061 | NA | 0.720 | 0.185 | 0.272 | 0.729 | 0.527 | 0.368 | 0.009 | 0.174 |
| *Roseburia hominis* (NT5079) | 1.000 | 1.000 | 1.000 | 0.378 | 1.000 | 1.000 | 1.000 | 0.609 | 1.000 | 0.637 | 0.822 | 1.000 | 1.000 | 0.001 |
| *Roseburia intestinalis* (NT5011) | 0.012 | 0.559 | 0.952 | 0.212 | 0.001 | NA | 1.000 | 0.007 | 0.001 | 1.000 | 0.391 | 1.000 | 0.003 | 1.000 |
| *Ruminococcus bromii* (NT5045) | 1.000 | 0.638 | 1.000 | 0.923 | 0.380 | 0.643 | 0.964 | 0.017 | 0.934 | 0.199 | 0.258 | 0.903 | 1.000 | 0.261 |
| *Ruminococcus gnavus* (NT5046) | 0.718 | 0.669 | 0.770 | 0.331 | 0.001 | 0.083 | 0.949 | 0.414 | 0.021 | 0.498 | 0.082 | 1.000 | 0.024 | 1.000 |
| *Ruminococcus torques* (NT5047) | 0.322 | 0.266 | 0.632 | 0.114 | 0.833 | 0.049 | 1.000 | 0.875 | 0.087 | 1.000 | 0.078 | 1.000 | 0.519 | 1.000 |
| *Streptococcus parasanguinis* (NT5072) | 0.042 | 1.000 | 0.706 | 0.098 | 0.083 | 0.009 | 0.448 | 0.035 | 0.033 | 1.000 | 0.024 | 1.000 | 0.181 | 1.000 |
| *Streptococcus salivarius* (NT5038) | 0.007 | 0.986 | 0.769 | 1.000 | <0.001 | 0.353 | 0.192 | 0.008 | 0.002 | 0.041 | 0.427 | 0.388 | 0.416 | 1.000 |
| *Veillonella parvula* (NT5017) | 1.000 | 0.003 | 1.000 | 0.867 | 1.000 | 1.000 | 1.000 | 0.947 | 0.526 | 0.106 | 0.766 | 1.000 | 1.000 | 0.925 |

Table 5 shows narrow-spectrum compounds effective against bacterial species but *Clostridium difficile* and an enterotoxigenic strain of *Bacteroides fragilis*. Shown are the adjusted p-values of the compound-induced inhibition on the growth of 40 different bacterial species as indicated. Note: A compound is defined as "narrow-spectrum" if it inhibits the growth of less than 9 species of 40 different bacterial species tested.

| | Alfacalcidol | Acarbose | Ethacrynic acid | Chlorpromazine hydrochloride | Cyclosporin A | Flufenamic acid | Aripiprazole | Idebenone | Thioguanosine |
|---|---|---|---|---|---|---|---|---|---|
| prestwick_ID | 1211 | 1174 | 259 | 64 | 435 | 203 | 1229 | 1288 | 347 |
| n_hit | 7 | 6 | 6 | 6 | 5 | 4 | 3 | 3 | 3 |
| *Akkermansia muciniphila* (NT5021) | 0.280 | 0.967 | 1.000 | <0.001 | 0.835 | 0.758 | 0.924 | 1.000 | 0.885 |
| *Bacteroides caccae* (NT5050) | 0.568 | 1.000 | 1.000 | 0.619 | 1.000 | 0.194 | 1.000 | 1.000 | 0.373 |
| *Bacteroides fragilis* (ET) (NT5033) | 0.784 | <0.001 | 0.001 | 0.026 | 0.913 | 0.027 | 0.147 | 0.540 | 1.000 |
| *Bacteroides fragilis* (NT) (NT5003) | 0.287 | 0.018 | 0.001 | 0.036 | 1.000 | 0.094 | 0.389 | 0.384 | 0.310 |
| *Bacteroides ovatus* (NT5054) | 0.983 | 0.792 | 0.349 | 0.124 | 0.362 | 0.001 | 1.000 | 0.923 | 0.712 |
| *Bacteroides thetaiotaomicron* (NT5004) | 1.000 | 0.020 | 0.063 | 0.013 | 1.000 | 0.073 | 0.934 | 1.000 | 0.312 |
| *Bacteroides uniformis* (NT5002) | 0.590 | 0.001 | <0.001 | 0.003 | 1.000 | 0.247 | 0.913 | 0.596 | 0.924 |
| *Bacteroides vulgatus* (NT5001) | 0.183 | 0.001 | <0.001 | <0.001 | 0.848 | 0.527 | 0.612 | 0.782 | 1.000 |
| *Bacteroides xylanisolvens* (NT5064) | 1.000 | <0.001 | 0.617 | 1.000 | 0.341 | 0.611 | 1.000 | 1.000 | 0.836 |
| *Bifidobacterium adolescentis* (NT5022) | 0.010 | 1.000 | 1.000 | 1.000 | 0.143 | 0.298 | 1.000 | 1.000 | 0.234 |
| *Bifidobacterium longum* (NT5028) | 0.008 | 1.000 | 1.000 | 0.713 | 0.004 | 0.377 | 1.000 | 1.000 | 0.324 |
| *Bilophila wadsworthia* (NT5036) | 0.242 | 0.713 | 0.887 | 0.919 | 1.000 | 1.000 | 1.000 | 1.000 | 0.815 |
| *Blautia obeum* (NT5069) | 0.408 | 1.000 | 0.792 | 0.759 | 0.004 | 0.056 | 1.000 | 1.000 | 0.519 |
| *Clostridium bolteae* (NT5026) | 0.653 | 1.000 | 0.006 | 0.864 | 1.000 | 0.501 | 0.003 | 0.394 | 0.549 |
| *Clostridium difficile* (NT5083) | 0.382 | 1.000 | 1.000 | 0.362 | 0.611 | 0.078 | 0.799 | 1.000 | 0.628 |
| *Clostridium perfringens* (NT5032) | <0.001 | <0.001 | 0.002 | 0.001 | <0.001 | 0.678 | 1.000 | 0.005 | <0.001 |
| *Clostridium ramosum* (NT5006) | 0.027 | 1.000 | 0.032 | 0.957 | 1.000 | 0.433 | 1.000 | 0.001 | 0.527 |
| *Closthridiulm saccharolyticum* (NT5037) | 0.680 | 1.000 | 0.040 | 0.202 | 1.000 | 0.089 | 0.997 | 1.000 | 0.853 |
| *Collinsella aerofaciens* (NT5073) | 0.312 | 1.000 | 1.000 | 0.810 | 0.049 | 0.705 | 1.000 | 1.000 | 0.249 |
| *Coprococcus comes* (NT5048) | 0.001 | 0.431 | 0.025 | 0.753 | 0.430 | 0.854 | 0.052 | 0.145 | 1.000 |
| *Dorea formicigenerans* (NT5076) | 0.011 | 1.000 | 0.197 | 1.000 | 0.104 | 1.000 | 0.139 | 1.000 | 0.264 |
| *Eggerthella lenta* (NT5024) | 0.659 | 1.000 | 1.000 | 0.360 | 1.000 | 0.389 | 1.000 | 1.000 | 0.887 |
| *Escherichia coli* ED1a (NT5078) | 1.000 | 1.000 | 0.826 | 1.000 | 1.000 | 0.734 | 1.000 | 1.000 | <0.001 |

-continued

| | | | | | | | | | |
|---|---|---|---|---|---|---|---|---|---|
| *Escherichia coli* IAI1 (NT5077) | 1.000 | 0.652 | 0.847 | 1.000 | 0.613 | 1.000 | 1.000 | 1.000 | <0.001 |
| *Eubacterium eligens* (NT5075) | 0.942 | 1.000 | 0.998 | 0.028 | 1.000 | 0.031 | 1.000 | 0.666 | 0.804 |
| *Eubacterium rectale* (NT5009) | 0.003 | <0.001 | 0.589 | 0.051 | 0.024 | 1.000 | 0.072 | 1.000 | 0.931 |
| *Fusobacterium nucleatum* (NT5025) | 1.000 | 0.633 | 0.016 | 0.721 | 1.000 | 0.239 | 1.000 | 1.000 | 0.910 |
| *Lactobacillus paracasei* (NT5042) | 0.939 | 1.000 | 1.000 | 1.000 | 0.353 | 0.692 | 0.913 | 0.331 | 1.000 |
| *Odoribacter splanchnicus* (NT5081) | 0.556 | 1.000 | 0.525 | 0.062 | 0.355 | 0.005 | 0.182 | 1.000 | 0.518 |
| *Parabacteroides distasonis* (NT5074) | 0.575 | 1.000 | 0.054 | 0.003 | 0.496 | 0.001 | <0.001 | 0.004 | 0.983 |
| *Parabacteroides merdae* (NT5071) | 0.441 | 0.984 | 0.024 | 0.004 | 1.000 | 0.009 | 0.137 | 0.156 | 1.000 |
| *Prevotella copri* (NT5019) | 0.250 | 0.956 | 0.827 | 0.032 | 0.404 | 0.264 | 0.008 | 1.000 | 1.000 |
| *Roseburia hominis* (NT5079) | 0.427 | 0.375 | 1.000 | 0.061 | <0.001 | 0.806 | 1.000 | 1.000 | 0.382 |
| *Roseburia intestinalis* (NT5011) | 0.001 | 0.021 | 0.904 | 1.000 | 0.016 | 1.000 | 0.021 | 0.477 | 1.000 |
| *Ruminococcus bromii* (NT5045) | 1.000 | 0.683 | 0.248 | 1.000 | 1.000 | 0.838 | 1.000 | 0.020 | 0.730 |
| *Ruminococcus gnavus* (NT5046) | 0.029 | 0.157 | 0.281 | 0.973 | 1.000 | 0.570 | 0.966 | 1.000 | 0.422 |
| *Ruminococcus torques* (NT5047) | 0.092 | 1.000 | 0.027 | 1.000 | 0.878 | 1.000 | 1.000 | 1.000 | 0.877 |
| *Streptococcus parasanguinis* (NT5072) | 0.006 | 1.000 | 0.623 | 1.000 | 0.792 | 0.628 | 1.000 | 0.076 | 0.837 |
| *Streptococcus salivarius* (NT5038) | <0.001 | 0.610 | 0.553 | 0.834 | 0.317 | 0.765 | 1.000 | 0.423 | 1.000 |
| *Veillonella parvula* (NT5017) | 0.698 | 1.000 | 0.837 | 0.628 | 0.003 | 0.022 | 1.000 | 1.000 | 0.447 |

| | Thyroxine (L) | Gemcitabine | Folic acid | Etretinate | Paclitaxel | Phenindione | Mometasone furoate | Azacytidine-5 | Luteolin |
|---|---|---|---|---|---|---|---|---|---|
| prestwick_ID | 403 | 1266 | 627 | 1409 | 155 | 538 | 572 | 866 | 870 |
| n_hit | 3 | 2 | 2 | 1 | 1 | 1 | 1 | 1 | 1 |
| *Akkermansia muciniphila* (NT5021) | 1.000 | 1.000 | 0.801 | 1.000 | 1.000 | 0.692 | 1.000 | 1.000 | 0.149 |
| *Bacteroides caccae* (NT5050) | 1.000 | 1.000 | 1.000 | 0.975 | 1.000 | 0.910 | 1.000 | 1.000 | 0.538 |
| *Bacteroides fragilis* (ET) (NT5033) | 1.000 | 1.000 | 0.952 | 1.000 | 0.924 | 0.826 | 1.000 | 0.795 | 0.443 |
| *Bacteroides fragilis* (NT) (NT5003) | 1.000 | 1.000 | 0.892 | 0.978 | 0.528 | 0.353 | 1.000 | 0.800 | 0.448 |
| *Bacteroides ovatus* (NT5054) | 1.000 | 1.000 | 1.000 | 1.000 | 1.000 | 0.973 | 1.000 | 1.000 | 1.000 |
| *Bacteroides thetaiotaomicron* (NT5004) | 1.000 | 1.000 | 1.000 | 1.000 | 1.000 | 0.783 | 1.000 | 1.000 | 1.000 |
| *Bacteroides uniformis* (NT5002) | 0.806 | 1.000 | 1.000 | 0.657 | 0.793 | 0.938 | 1.000 | 1.000 | 0.266 |

-continued

| | | | | | | | | | |
|---|---|---|---|---|---|---|---|---|---|
| *Bacteroides vulgatus* (NT5001) | 1.000 | 1.000 | 1.000 | 0.886 | 0.699 | 0.908 | 1.000 | 0.998 | 1.000 |
| *Bacteroides xylanisolvens* (NT5064) | 1.000 | 1.000 | 0.939 | 1.000 | 1.000 | 0.211 | 1.000 | 1.000 | 1.000 |
| *Bifidobacterium adolescentis* (NT5022) | 1.000 | 1.000 | 0.674 | 0.875 | 1.000 | 0.354 | 1.000 | 1.000 | 0.886 |
| *Bifidobacterium longum* (NT5028) | 1.000 | 1.000 | 0.990 | 1.000 | 1.000 | 0.583 | 1.000 | 1.000 | 1.000 |
| *Bilophila wadsworthia* (NT5036) | 0.905 | 1.000 | 1.000 | 1.000 | 1.000 | 1.000 | 1.000 | 0.746 | 0.383 |
| *Blautia obeum* (NT5069) | 1.000 | 1.000 | 1.000 | 1.000 | 1.000 | 0.400 | 1.000 | 1.000 | 1.000 |
| *Clostridium bolteae* (NT5026) | NA | 1.000 | 1.000 | 1.000 | 0.900 | 0.943 | 1.000 | 1.000 | 0.176 |
| *Clostridium difficile* (NT5083) | 0.064 | 1.000 | 1.000 | 0.249 | 0.668 | 0.526 | 1.000 | 1.000 | 0.023 |
| *Clostridium perfringens* (NT5032) | 1.000 | <0.001 | 0.989 | <0.001 | <0.001 | 0.009 | 0.958 | <0.001 | 0.018 |
| *Clostridium ramosum* (NT5006) | 1.000 | 1.000 | <0.001 | 1.000 | 0.897 | 0.725 | 0.991 | 0.525 | 0.586 |
| *Closthridiulm saccharolyticum* (NT5037) | 0.001 | 1.000 | 0.158 | 1.000 | 0.894 | 0.801 | 1.000 | 0.991 | 0.025 |
| *Collinsella aerofaciens* (NT5073) | 1.000 | 1.000 | 1.000 | 1.000 | 1.000 | 0.051 | 0.108 | 1.000 | 1.000 |
| *Coprococcus comes* (NT5048) | 0.064 | 0.645 | 1.000 | 0.922 | 1.000 | 0.967 | 0.903 | 1.000 | NA |
| *Dorea formicigenerans* (NT5076) | 1.000 | 1.000 | 0.882 | 1.000 | 1.000 | 0.838 | 1.000 | 1.000 | 0.311 |
| *Eggerthella lenta* (NT5024) | 1.000 | 1.000 | 1.000 | 1.000 | 1.000 | 1.000 | 1.000 | 1.000 | 1.000 |
| *Escherichia coli* ED1a (NT5078) | 1.000 | 1.000 | 1.000 | 1.000 | 1.000 | 0.763 | 1.000 | 0.180 | 1.000 |
| *Escherichia coli* IAI1 (NT5077) | 0.997 | 1.000 | 0.733 | 0.810 | 0.968 | 0.581 | 1.000 | 0.384 | 0.515 |
| *Eubacterium eligens* (NT5075) | 0.002 | 1.000 | 1.000 | 0.454 | 1.000 | 0.935 | 1.000 | 1.000 | 1.000 |
| *Eubacterium rectale* (NT5009) | 0.043 | 1.000 | 0.001 | 0.225 | 0.851 | 1.000 | 1.000 | 1.000 | 0.340 |
| *Fusobacterium nucleatum* (NT5025) | 1.000 | 1.000 | 0.684 | 1.000 | 1.000 | 0.971 | 1.000 | 0.778 | 0.001 |
| *Lactobacillus paracasei* (NT5042) | 0.009 | 1.000 | 1.000 | 1.000 | 0.934 | 0.995 | 1.000 | 1.000 | 1.000 |
| *Odoribacter splanchnicus* (NT5081) | 1.000 | 1.000 | 1.000 | 1.000 | 1.000 | 0.665 | 1.000 | 0.657 | 0.612 |
| *Parabacteroides distasonis* (NT5074) | 1.000 | 0.296 | 0.824 | 1.000 | 0.909 | 1.000 | 0.380 | 1.000 | 1.000 |
| *Parabacteroides merdae* (NT5071) | 1.000 | 1.000 | 1.000 | 0.721 | 0.220 | 0.826 | 0.689 | 1.000 | 0.330 |
| *Prevotella copri* (NT5019) | 1.000 | <0.001 | 1.000 | 0.293 | 0.950 | 1.000 | 1.000 | 0.042 | 0.562 |
| *Roseburia hominis* (NT5079) | 0.262 | 1.000 | 1.000 | 0.998 | 1.000 | 0.490 | 1.000 | 1.000 | 1.000 |

-continued

| | | | | | | | | | |
|---|---|---|---|---|---|---|---|---|---|
| Roseburia intestinalis (NT5011) | 0.183 | 1.000 | 1.000 | 0.226 | 0.622 | 0.902 | 1.000 | 0.514 | 0.430 |
| Ruminococcus bromii (NT5045) | 1.000 | 1.000 | 1.000 | 1.000 | 1.000 | 1.000 | 0.379 | 1.000 | 1.000 |
| Ruminococcus gnavus (NT5046) | 1.000 | 0.046 | 0.424 | 0.923 | 0.955 | 0.918 | 1.000 | 0.713 | 0.033 |
| Ruminococcus torques (NT5047) | 1.000 | 1.000 | 0.823 | 0.263 | 1.000 | 0.995 | 1.000 | 1.000 | 0.061 |
| Streptococcus parasanguinis (NT5072) | 1.000 | 0.896 | 1.000 | 0.921 | 0.872 | 0.691 | 1.000 | 0.870 | 0.077 |
| Streptococcus salivarius (NT5038) | 1.000 | 1.000 | 0.981 | 1.000 | 0.754 | 1.000 | 0.734 | 0.988 | 0.388 |
| Veillonella parvula (NT5017) | 1.000 | 1.000 | 0.880 | 1.000 | 1.000 | 0.061 | <0.001 | 1.000 | 1.000 |

Table 6 shows narrow-spectrum compounds effective against an enterotoxigenic strain of *Bacteroides fragilis*. Shown are the adjusted p-values of the compound-induced inhibition on the growth of 40 different bacterial species as indicated. Note: A compound is defined as "narrow-spectrum" if it inhibits the growth of less than 9 species of 40 different bacterial species tested.

| | Metixene hydrochloride | Protriptyline hydrochloride | Toltrazuril | Acarbose | Ethacrynic acid | Tolnaftate | Meclofenamic acid | Prenylamine lactate |
|---|---|---|---|---|---|---|---|---|
| prestwick_ID | 491 | 930 | 1195 | 1174 | 259 | 70 | 206 | 560 |
| n_hit | 9 | 8 | 7 | 6 | 6 | 5 | 5 | 5 |
| Akkermansia muciniphila (NT5021) | 0.197 | 0.039 | 1.000 | <0.001 | 1.000 | 0.832 | 1.000 | 1.000 |
| Bacteroides caccae (NT5050) | 0.006 | 0.005 | 0.293 | 1.000 | 1.000 | 0.678 | 0.113 | 1.000 |
| Bacteroides fragilis (ET) (NT5033) | 0.007 | 0.009 | 0.002 | <0.001 | 0.001 | 0.009 | 0.001 | 0.001 |
| Bacteroides fragilis (NT) (NT5003) | 0.028 | 0.003 | 0.074 | 0.018 | 0.001 | 0.040 | 0.009 | 0.253 |
| Bacteroides ovatus (N15054) | <0.001 | <0.001 | 0.076 | 0.792 | 0.349 | 0.095 | 0.006 | 1.000 |
| Bacteroides thetaiotaomicron (NT5004) | <0.001 | 0.001 | 0.435 | 0.020 | 0.063 | 0.036 | 0.010 | 0.090 |
| Bacteroides uniformis (NT5002) | <0.001 | <0.001 | 0.295 | 0.001 | <0.001 | 0.024 | 0.016 | 0.027 |
| Bacteroides vulgatus (NT5001) | <0.001 | <0.001 | 0.033 | 0.001 | <0.001 | 0.034 | 0.072 | <0.001 |
| Bacteroides xylanisolvens (NT5064) | 0.200 | 0.796 | 1.000 | <0.001 | 0.617 | 1.000 | 0.357 | 1.000 |
| Bifidobacterium adolescentis (NT5022) | 1.000 | 0.928 | 1.000 | 1.000 | 1.000 | 0.854 | 0.659 | 1.000 |
| Bifidobacterium longum (NT5028) | 1.000 | 1.000 | 1.000 | 1.000 | 1.000 | 0.883 | 0.995 | 1.000 |
| Bilophila wadsworthia (NT5036) | 1.000 | 0.832 | 0.812 | 0.713 | 0.887 | 0.638 | 0.951 | 0.251 |
| Blautia obeum (NT5069) | 0.792 | 1.000 | 0.342 | 1.000 | 0.792 | 0.501 | 0.955 | 0.860 |
| Clostridium bolteae (NT5026) | 0.569 | 1.000 | 0.910 | 1.000 | 0.006 | 0.897 | 1.000 | 0.442 |
| Clostridium difficile (NT5083) | 1.000 | 0.757 | 1.000 | 1.000 | 1.000 | 1.000 | 0.111 | 0.773 |

| | Metixene hydrochloride | Protriptyline hydrochloride | Toltrazuril | Acarbose | Ethacrynic acid | Tolnaftate | Meclofenamic acid | Prenylamine lactate |
|---|---|---|---|---|---|---|---|---|
| *Clostridium perfringens* (NT5032) | 0.337 | 1.000 | 0.007 | <0.001 | 0.002 | 0.007 | 0.266 | 0.796 |
| *Clostridium ramosum* (NT5006) | 1.000 | 1.000 | 1.000 | 1.000 | 0.032 | 1.000 | 0.653 | 1.000 |
| *Clostridium saccharolyticum* (NT5037) | 1.000 | 1.000 | 1.000 | 1.000 | 0.040 | 0.072 | 0.201 | 0.651 |
| *Collinsella aerofaciens* (NT5073) | 1.000 | 0.745 | 1.000 | 1.000 | 1.000 | 0.451 | 1.000 | 1.000 |
| *Coprococcus comes* (NT5048) | 0.084 | 0.964 | 0.040 | 0.431 | 0.025 | 0.464 | 0.394 | 0.124 |
| *Dorea formicigenerans* (NT5076) | 1.000 | 0.664 | 0.792 | 1.000 | 0.197 | 0.161 | 0.963 | 0.736 |
| *Eggerthella lenta* (NT5024) | 0.931 | 0.564 | 1.000 | 1.000 | 1.000 | 1.000 | 1.000 | 1.000 |
| *Escherichia coli* ED1a (NT5078) | 1.000 | 0.302 | 1.000 | 1.000 | 0.826 | 1.000 | 0.398 | 0.438 |
| *Escherichia coli* IAI1 (NT5077) | 1.000 | 0.725 | 0.502 | 0.652 | 0.847 | 0.558 | 0.394 | 0.126 |
| *Eubacterium eligens* (NT5075) | 0.023 | 0.477 | 1.000 | 1.000 | 0.998 | 1.000 | 1.000 | 0.001 |
| *Eubacterium rectale* (NT5009) | 0.047 | 0.148 | 0.030 | <0.001 | 0.589 | 0.173 | 1.000 | 0.006 |
| *Fusobacterium nucleatum* (NT5025) | 1.000 | 1.000 | 1.000 | 0.633 | 0.016 | 0.393 | 0.015 | 0.550 |
| *Lactobacillus paracasei* (NT5042) | 1.000 | 1.000 | 0.075 | 1.000 | 1.000 | 0.003 | 0.638 | 0.034 |
| *Odoribacter splanchnicus* (NT5081) | 0.001 | 0.231 | 0.004 | 1.000 | 0.525 | 0.934 | 0.020 | 1.000 |
| *Parabacteroides distasonis* (NT5074) | <0.001 | 0.166 | <0.001 | 1.000 | 0.054 | 0.102 | 0.003 | 0.014 |
| *Parabacteroides merdae* (NT5071) | <0.001 | 0.007 | <0.001 | 0.984 | 0.024 | 0.013 | 0.001 | 0.011 |
| *Prevotella copri* (NT5019) | 0.018 | 0.285 | 0.001 | 0.956 | 0.827 | 0.831 | 0.316 | 0.055 |
| *Roseburia hominis* (NT5079) | 1.000 | 1.000 | 1.000 | 0.375 | 1.000 | 0.976 | 1.000 | 0.768 |
| *Roseburia intestinalis* (NT5011) | 0.899 | 1.000 | 0.007 | 0.021 | 0.904 | 0.008 | 1.000 | 0.005 |
| *Ruminococcus bromii* (NT5045) | 0.675 | 1.000 | 0.126 | 0.683 | 0.248 | 0.531 | 0.682 | 1.000 |
| *Ruminococcus gnavus* (NT5046) | 0.526 | 0.971 | 0.031 | 0.157 | 0.281 | 0.665 | 0.256 | 0.029 |
| *Ruminococcus torques* (NT5047) | 1.000 | 1.000 | 0.182 | 1.000 | 0.027 | <0.001 | 0.971 | 0.699 |
| *Streptococcus parasanguinis* (NT5072) | 1.000 | 0.995 | 0.438 | 1.000 | 0.623 | 0.236 | 0.043 | 0.075 |
| *Streptococcus salivarius* (NT5038) | 1.000 | 0.450 | 0.781 | 0.610 | 0.553 | 0.711 | 0.337 | 0.299 |
| *Veillonella parvula* (NT5017) | 1.000 | 0.925 | 1.000 | 1.000 | 0.837 | 0.914 | 1.000 | 1.000 |

Table 7 shows compounds effective against a broad spectrum of bacteria. Shown are the adjusted p-values of the compound-induced inhibition on the growth of 40 different bacterial species as indicated. Note: A compound is defined as "broad-spectrum" compound if it inhibits the growth of ≥10 species of 40 different bacterial species tested.

| prestwick_ID | Diacerein | Tiratricol | Troglitazone | Dicumarol | Anthralin | Astemizole | Loratadine | Estradiol Valerate | Aprepitant | Clemizole hydrochloride | Bepridil hydrochloride | Methiothepin maleate | Amiodarone hydrochloride | Ethopropazine hydrochloride |
|---|---|---|---|---|---|---|---|---|---|---|---|---|---|---|
| n_hit | 1167 33 | 202 14 | 1467 13 | 785 10 | 1224 11 | 136 10 | 1432 15 | 1473 11 | 1600 10 | 227 15 | 368 14 | 375 10 | 409 10 | 840 11 |
| *Akkermansia muciniphila* (NT5021) | 0.108 | 1.000 | 1.000 | 0.895 | 0.944 | 0.001 | 1.000 | 1.000 | 0.518 | 0.019 | 0.538 | 0.064 | 1.000 | 0.049 |
| *Bacteroides caccae* (NT5050) | <0.001 | 0.118 | 0.020 | 0.043 | 1.000 | 1.000 | 0.026 | 0.004 | 0.004 | 0.634 | 0.145 | 0.097 | 0.371 | <0.001 |
| *Bacteroides fragilis* (ET) (NT5033) | <0.001 | 0.015 | 0.231 | 0.013 | 0.051 | 0.565 | 0.002 | 0.007 | <0.001 | 0.437 | 0.078 | 0.053 | 0.348 | <0.001 |
| *Bacteroides fragilis* (NT) (NT5003) | <0.001 | 0.108 | 0.004 | 0.002 | 0.002 | 0.504 | 0.110 | <0.001 | <0.001 | 0.612 | 0.294 | 0.091 | 0.044 | <0.001 |
| *Bacteroides ovatus* (NT5054) | <0.001 | 0.003 | 0.263 | 0.002 | 1.000 | 1.000 | 0.001 | 1.000 | 0.144 | 0.855 | 0.128 | 0.167 | 1.000 | <0.001 |
| *Bacteroides thetaiotaomicron* (NT5004) | <0.001 | 0.017 | 0.107 | 0.042 | 0.567 | 0.649 | 0.025 | 0.445 | 0.464 | 0.363 | 0.007 | 0.024 | 0.322 | <0.001 |
| *Bacteroides uniformis* (NT5002) | <0.001 | 0.507 | 0.266 | 0.002 | 0.238 | 0.214 | 0.151 | 0.032 | 0.024 | 0.171 | 0.081 | 0.282 | 0.717 | <0.001 |
| *Bacteroides vulgatus* (NT5001) | <0.001 | 0.526 | 0.025 | 0.137 | 0.006 | 0.323 | 0.012 | <0.001 | <0.001 | 0.012 | 0.008 | 0.084 | 0.003 | <0.001 |
| *Bacteroides xylanisolvens* (NT5064) | <0.001 | 1.000 | 0.044 | 0.025 | 1.000 | 1.000 | 0.030 | 0.290 | 0.046 | 1.000 | 1.000 | 1.000 | 1.000 | <0.001 |
| *Bifidobacterium adolescentis* (NT5022) | 1.000 | <0.001 | 0.881 | 1.000 | 1.000 | 1.000 | 0.001 | 0.308 | 0.319 | 0.010 | 0.098 | 0.582 | 0.151 | 1.000 |
| *Bifidobacterium longum* (NT5028) | 0.898 | 0.197 | 0.274 | 0.969 | 1.000 | 0.993 | 0.001 | 0.024 | 0.008 | 0.059 | 0.051 | 0.001 | <0.001 | 1.000 |
| *Bilophila wadsworthia* (NT5036) | 0.478 | 0.921 | 1.000 | 1.000 | 1.000 | 1.000 | <0.001 | 0.369 | 0.511 | 0.266 | 0.981 | 0.895 | 0.068 | 0.559 |
| *Blautia obeum* (NT5069) | <0.001 | <0.001 | <0.001 | 0.832 | <0.001 | <0.001 | 0.157 | 0.692 | 0.001 | <0.001 | <0.001 | <0.001 | <0.001 | 0.646 |
| *Clostridium bolteae* (NT5026) | <0.001 | 0.049 | 0.334 | 0.007 | 0.007 | 0.980 | 0.020 | 0.661 | 0.167 | 0.050 | 0.001 | 0.103 | 0.258 | 0.768 |
| *Clostridium difficile* (NT5083) | <0.001 | <0.001 | <0.001 | 1.000 | 0.010 | 1.000 | <0.001 | 0.071 | 0.109 | 0.189 | 0.022 | 0.073 | 0.189 | 0.441 |
| *Clostridium perfringens* (NT5032) | <0.001 | <0.001 | <0.001 | 0.010 | 0.001 | 0.010 | <0.001 | 0.001 | 0.263 | <0.001 | 0.005 | 0.101 | 0.095 | 1.000 |

-continued

| | Diacerein | Tiratricol | Troglitazone | Dicumarol | Anthralin | Astemizole | Loratadine | Estradiol Valerate | Aprepitant | Clemizole hydrochloride | Bepridil hydrochloride | Methiothepin maleate | Amiodarone hydrochloride | Ethopropazine hydrochloride |
|---|---|---|---|---|---|---|---|---|---|---|---|---|---|---|
| *Clostridium ramosum* (NT5006) | <0.001 | 0.001 | <0.001 | 0.175 | 0.121 | 0.896 | 0.463 | 1.000 | 0.883 | <0.001 | 0.236 | 0.354 | 0.930 | 0.949 |
| *Clostridium saccharolyticum* (NT5037) | <0.001 | <0.001 | 0.061 | 0.026 | 0.507 | 0.148 | 0.311 | 1.000 | 0.974 | <0.001 | 0.334 | 0.211 | 1.000 | 1.000 |
| *Collinsella aerofaciens* (NT5073) | <0.001 | 0.020 | 0.543 | 0.808 | 0.152 | 0.608 | <0.001 | 0.963 | 0.097 | <0.001 | 0.001 | 0.003 | 0.001 | 0.449 |
| *Coprococcus comes* (NT5048) | <0.001 | 0.009 | 0.004 | 1.000 | <0.001 | 0.005 | <0.001 | <0.001 | 0.018 | <0.001 | 0.089 | 0.138 | <0.001 | 0.091 |
| *Dorea formicigenerans* (NT5076) | <0.001 | 0.046 | 0.814 | 0.813 | 1.000 | <0.001 | <0.001 | 0.403 | 0.040 | 0.001 | 0.009 | 0.037 | 0.047 | 1.000 |
| *Eggerthella lenta* (NT5024) | <0.001 | 0.006 | 0.153 | 0.934 | <0.001 | 0.127 | 1.000 | 1.000 | 1.000 | 0.796 | 0.459 | 0.738 | 0.871 | 0.506 |
| *Escherichia coli* ED1a (NT5078) | 0.497 | 1.000 | 1.000 | 0.697 | 1.000 | 1.000 | 0.414 | 0.668 | 0.799 | 0.564 | 0.967 | 1.000 | 1.000 | 0.963 |
| *Escherichia coli* IAI1 (NT5077) | 1.000 | 1.000 | 1.000 | 0.871 | 1.000 | 1.000 | 0.740 | 0.719 | 0.749 | 0.215 | 0.117 | 1.000 | 0.996 | 0.883 |
| *Eubacterium eligens* (NT5075) | <0.001 | 0.292 | 0.265 | 1.000 | 0.060 | 0.002 | <0.001 | 1.000 | 1.000 | <0.001 | <0.001 | 0.001 | <0.001 | 0.874 |
| *Eubacterium rectale* (NT5009) | <0.001 | 1.000 | 0.003 | 1.000 | 0.241 | 0.001 | 0.001 | 0.002 | 0.558 | <0.001 | 0.002 | 0.002 | 0.001 | 0.051 |
| *Fusobacterium nucleatum* (NT5025) | <0.001 | 0.342 | 1.000 | 0.019 | 1.000 | 1.000 | 1.000 | 0.849 | 1.000 | 0.015 | 0.527 | 1.000 | 1.000 | 1.000 |
| *Lactobacillus paracasei* (NT5042) | 0.829 | 0.595 | 0.992 | 1.000 | 0.483 | 0.858 | 0.009 | 0.013 | 0.659 | 0.002 | 0.019 | 0.796 | 0.078 | 1.000 |

-continued

| | Diacerein | Tiratricol | Troglitazone | Dicumarol | Anthralin | Astemizole | Loratadine | Estradiol Valerate | Aprepitant | Clemizole hydrochloride | Bepridil hydrochloride | Methiothepin maleate | Amiodarone hydrochloride | Ethopropazine hydrochloride |
|---|---|---|---|---|---|---|---|---|---|---|---|---|---|---|
| *Odoribacter splanchnicus* (NT5081) | <0.001 | 0.002 | 0.069 | 0.001 | <0.001 | 0.878 | 0.167 | 0.659 | 0.018 | 0.557 | 0.015 | 0.004 | 1.000 | <0.001 |
| *Parabacteroides distasonis* (NT5074) | <0.001 | 0.001 | 0.012 | <0.001 | 0.879 | 0.107 | 0.016 | 0.255 | 0.002 | 0.104 | 0.002 | 0.004 | 0.013 | <0.001 |
| *Parabacteroides merdae* (NT5071) | <0.001 | 0.003 | 0.812 | 0.007 | <0.001 | 0.635 | 0.013 | 0.001 | 0.251 | 0.441 | 0.007 | 0.472 | 0.013 | <0.001 |
| *Prevotella copri* (NT5019) | <0.001 | 0.132 | 0.006 | 0.020 | 0.053 | 0.008 | 0.121 | 0.007 | 0.016 | 0.143 | 0.033 | <0.001 | 0.009 | 0.024 |
| *Roseburia hominis* (NT5079) | <0.001 | 1.000 | 1.000 | 1.000 | 1.000 | 0.010 | 0.492 | 1.000 | 0.001 | <0.001 | 0.118 | <0.001 | <0.001 | 1.000 |
| *Roseburia intestinalis* (NT5011) | <0.001 | 0.008 | 0.001 | 1.000 | 1.000 | 0.001 | <0.001 | 0.011 | <0.001 | <0.001 | 0.002 | 0.001 | <0.001 | 0.776 |
| *Ruminococcus bromii* (NT5045) | <0.001 | 0.031 | 0.002 | 0.146 | 0.354 | 1.000 | <0.001 | <0.001 | 0.210 | <0.001 | 0.821 | 0.163 | 0.072 | 0.823 |
| *Ruminococcus gnavus* (NT5046) | <0.001 | 0.036 | 0.004 | 0.017 | 0.050 | 0.001 | 0.029 | 0.028 | 0.236 | <0.001 | 0.005 | 0.247 | 0.029 | 0.547 |
| *Ruminococcus torques* (NT5047) | <0.001 | 1.000 | 0.001 | 1.000 | 1.000 | 0.001 | 0.001 | 0.001 | 0.130 | <0.001 | 0.012 | 1.000 | 0.117 | 1.000 |
| *Streptococcus parasanguinis* (NT5072) | <0.001 | 0.012 | 0.119 | <0.001 | 1.000 | 0.913 | 0.055 | 1.000 | 0.776 | 0.757 | 0.050 | 1.000 | 0.326 | 0.741 |
| *Streptococcus salivarius* (NT5038) | <0.001 | <0.001 | <0.001 | <0.001 | 1.000 | 1.000 | 0.363 | 0.067 | 1.000 | 0.123 | 0.009 | 0.188 | 0.880 | 0.460 |
| *Veillonella parvula* (NT5017) | <0.001 | 0.826 | 1.000 | 0.968 | <0.001 | 1.000 | 0.477 | 1.000 | 0.009 | 0.677 | 0.345 | 0.223 | 1.000 | 0.920 |

The invention claimed is:

1. A method for reducing growth of bacterial cells, wherein said method comprises contacting bacterial cells with a compound that is a Ca-channel inhibitor, and wherein said bacteria are *Clostridia* selected from the group consisting of *C. difficile, C. butyricum, C. perfringens, C. novyi, C. septicum, C. botulinum, C. tetani, C. haemolyticum, C. carnis, C. histolyticum, C. sordellii, C. septicum, C. tertium, C. sporogenes, C. ramosum, C. inocuum, C. paraputrificum, C. cadaveris, C. bifermentans, C. fallax*, and *C. clostridioforme*, and combinations thereof.

2. The method according to claim 1, wherein a therapeutically effective amount of said compound is administered to a subject, thereby reducing the growth of bacterial cells in said subject, wherein said reducing results in the prevention and/or treatment of a disease caused by said bacterial growth in said subject and/or in the modification of the composition of the microbiome of said subject.

3. The method according to claim 2, wherein said disease is selected from an infectious disease, a gastrointestinal disorder, an inflammatory disease, a proliferative disease, a metabolic disorder, a cardiovascular disease, and an immunological disease.

4. The method according to claim 1, wherein said compound is in the form of a tablet, coated tablet, effervescent tablet, capsule, powder, granulate, sugar-coated tablet, lozenge, pill, ampoule, drop, suppository, emulsion, ointment, gel, tincture, paste, cream, moist compress, gargling solution, plant juice, nasal agent, inhalation mixture, aerosol, mouthwash, mouth spray, nose spray or room spray.

5. The method according to claim 2, wherein said compound is administered to said subject by oral, intranasal, topical, rectal, bronchial, vaginal, or parenteral administration.

6. The method according to claim 1, wherein said Ca-channel inhibitor is selected from a dihydropyridine, Fendiline hydrochloride, pharmaceutically acceptable salts thereof, and derivatives thereof.

7. The method according to claim 6, said dihydropyridine is selected from Lacidipine, Cilnidipine, Amlodipine, and pharmaceutically acceptable salts thereof.

* * * * *

UNITED STATES PATENT AND TRADEMARK OFFICE
CERTIFICATE OF CORRECTION

PATENT NO. : 11,766,427 B2
APPLICATION NO. : 16/966307
DATED : September 26, 2023
INVENTOR(S) : Mihaela Pruteanu et al.

Page 1 of 1

It is certified that error appears in the above-identified patent and that said Letters Patent is hereby corrected as shown below:

In the Specification

Column 13,
Line 11, "and 1025" should read --and IC25--
Line 12, "an 1025" should read --an IC25--

Signed and Sealed this
Tenth Day of December, 2024

Katherine Kelly Vidal
*Director of the United States Patent and Trademark Office*